(12) United States Patent
Egawa et al.

(10) Patent No.: US 7,612,204 B2
(45) Date of Patent: Nov. 3, 2009

(54) QUINOXALINE DERIVATIVE, AND LIGHT-EMITTING ELEMENT AND LIGHT-EMITTING DEVICE USING QUINOXALINE DERIVATIVE

(75) Inventors: Masakazu Egawa, Tochigi (JP); Atsushi Tokuda, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 11/866,179

(22) Filed: Oct. 2, 2007

(65) Prior Publication Data

US 2008/0091012 A1 Apr. 17, 2008

(30) Foreign Application Priority Data

Oct. 6, 2006 (JP) ............................. 2006-275716

(51) Int. Cl.
*C07D 241/36* (2006.01)
(52) U.S. Cl. ...................................................... 544/353
(58) Field of Classification Search .................. 544/353
See application file for complete search history.

(56) References Cited

U.S. PATENT DOCUMENTS

| 5,077,142 | A | * | 12/1991 | Sakon et al. ................. 428/690 |
| 7,227,313 | B2 | * | 6/2007 | Huiberts et al. ............ 315/169.3 |
| 2005/0118454 | A1 | | 6/2005 | Nakaya et al. |
| 2005/0186446 | A1 | | 8/2005 | Shitagaki et al. |

FOREIGN PATENT DOCUMENTS

| EP | 1 475 380 A1 | | 11/2004 |
| EP | 1 616 864 A1 | | 1/2006 |
| JP | 2003-040873 | * | 2/2003 |
| JP | 2003-40873 | | 2/2003 |
| JP | 2003-203780 | | 7/2003 |
| JP | 2006-16384 | | 1/2006 |
| JP | 2006-89728 | | 4/2006 |
| WO | WO 2004/094389 A1 | | 11/2004 |
| WO | WO 2006/022193 A1 | | 3/2006 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

OTHER PUBLICATIONS

Thomas, K.R.J. et al, "Quinoxalines Incorporating Triarylamines: Potential Electroluminescent Materials with Tunable Emission Characteristics," Chemistry of Materials, vol. 14, No. 6, Jun. 2002, pp. 2796-2802.

(Continued)

*Primary Examiner*—James O Wilson
*Assistant Examiner*—Douglas M Willis
(74) *Attorney, Agent, or Firm*—Cook Alex Ltd.

(57) ABSTRACT

An object is to provide a novel organic compound capable of visible light emission. In particular, an object is to provide a novel organic compound that exhibits a broad emission spectrum when it is used for a light-emitting element. In addition, an object is to provide a light-emitting element and a light-emitting device that gives white light emission with an excellent color rendering property. The quinoxaline derivative represented by General Formula (1) is provided. Since the quinoxaline derivative represented by General Formula (1) is capable of emitting visible light, it can be favorably used for a light-emitting element. In particular, since the quinoxaline derivative represented by General Formula (1) exhibits a broad emission spectrum when it is used for a light-emitting element, by using it for a light-emitting element a light-emitting element that gives white light emission with an excellent color rendering property can be obtained.

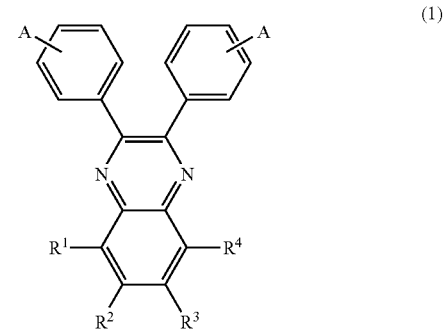

(1)

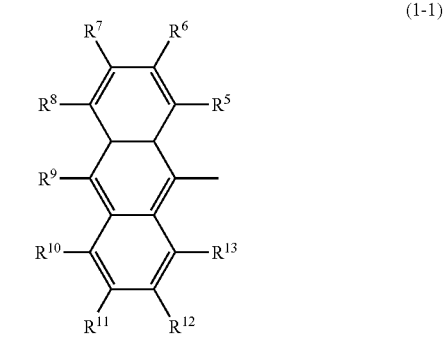

(1-1)

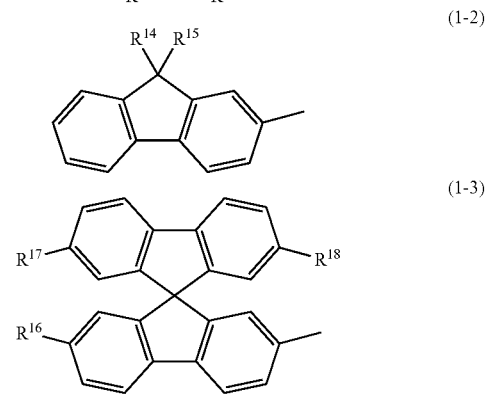

(1-2)

(1-3)

5 Claims, 33 Drawing Sheets

OTHER PUBLICATIONS

Thomas, K.R.J. et al, "Chromophore-Labeled Quinoxaline Derivatives as Efficient Electroluminescent Materials," Chemistry of Materials, vol. 17, No. 7, Apr. 5, 2005, pp. 1860-1866.

Chen, S. et al, "New Organic Light-Emitting Materials: Synthesis, Thermal, Photophysical, Electrochemical and Electroluminescent Properties," Database Caplus on STN, AN 2006:1296274, DN 146:260905, Journal of Physical Chemistry, vol. 111, No. 2, 2007, pp. 1029-1034.

Xiao, L. et al, "Highly Efficient Electron-Transporting Phenanthroline Derivatives for Electroluminescent Devices," Chemistry Letters, vol. 36, No. 6, 2007, pp. 802-803.

International Search Report re application No. PCT/JP2007/069151, dated Oct. 23, 2007.

Written Opinion re application no. PCT/JP2007/069151, dated Oct. 23, 2007.

* cited by examiner

QUINOXALINE DERIVATIVE, AND LIGHT-EMITTING ELEMENT AND LIGHT-EMITTING DEVICE USING QUINOXALINE DERIVATIVE

BACKGROUND OF THE INVENTION

1. Field of the Invention

The present invention relates to a quinoxaline derivative, and a light-emitting element and light-emitting device using the quinoxaline derivative.

2. Description of Related Art

In recent years, research and development have been extensively conducted on light-emitting elements using electroluminescence. As a basic structure of these light-emitting elements, a structure where a substance having a light-emitting property is interposed between a pair of electrodes is used. By application of a voltage to this element, light emission from a substance having a light-emitting property can be obtained.

Since such a light-emitting element is a self-luminous element, there are advantages that visibility of a pixel is better than visibility of a liquid crystal display, that a backlight is not necessary, and the like. Accordingly, such a light-emitting element is considered suitable as a flat panel display element. In addition, such a light-emitting element can be manufactured to be thin and light, which is a great advantage. Moreover, the light-emitting element has a feature that response speed is extremely fast.

Furthermore, since such a light-emitting element can be formed into a film form, planar light emission can be easily obtained by formation of a large-area element. This characteristic is difficult to be obtained by a point light source typified by an incandescent lamp or an LED, or a line light source typified by a fluorescent lamp. Therefore, the light-emitting element has a high utility value as a plane light source that can be applied to lighting or the like.

The light-emitting elements using electroluminescence are classified roughly in accordance with whether they use an organic compound or an inorganic compound as a substance having a light-emitting property.

In a case where a substance having a light-emitting property is an organic compound, by application of a voltage to the light-emitting element electrons and holes are injected from the pair of electrodes into the layer including an organic compound having a light-emitting property to cause current flow. Then, by recombination of these carriers (electrons and holes), the organic compound having a light-emitting property gets in an excited state, and light is emitted when the excited state returns to a ground state. Because of such a mechanism, this kind of light-emitting element is referred to as a light-emitting element of a current excitation type.

It is to be noted that an excited state formed by an organic compound can be a singlet-excited state or a triplet-excited state. Light emission from the singlet-excited state is referred to as fluorescence, and light emission from the triplet excited state is referred to as phosphorescence.

In order to overcome many problems derived from materials of such a light-emitting element and to improve its element characteristics, improvement in an element structure, material development, and so on are carried out.

For example, when the light-emitting element is used for a lighting system, the color rendering property of light emission of the light-emitting element becomes a concern. When a white light-emitting element is manufactured using a plurality of light-emitting materials, the color rendering property becomes low if the emission spectrum of each light-emitting material is sharp. On the other hand, if the emission spectrum is broad, the color rendering property becomes high because light emission occurs in the entire visible light region; accordingly, light emission that is close to that of natural light can be obtained.

However, with the light-emitting element using a plurality of light-emitting materials, it is difficult to adjust the balance of light emitted from the light-emitting materials. In addition, since the light-emitting materials differ in how easily they become degraded, even if the light-emitting element provides target white light emission when it is first manufactured, the luminance balance of the light-emitting materials changes due to the degradation, and there is a problem that the light emission color of the light-emitting element changes.

In Patent Document 1: Japanese Published Patent Application No. 2003-203780, a white light-emitting compound including a quinacridone skeleton and a carbazole skeleton is disclosed. However, there are still not very many compounds capable of white light emission, and the development of a novel white light-emitting compound is demanded.

BRIEF SUMMARY OF THE INVENTION

In view of the foregoing problem, an object is to provide a novel organic compound capable of visible light emission. In particular, an object is to provide a novel organic compound that exhibits a broad emission spectrum when it is used for a light-emitting element.

In addition, an object is to provide a light-emitting element and a light-emitting device that gives white light emission with an excellent color rendering property.

One feature of the present invention is a quinoxaline derivative represented by General Formula (1).

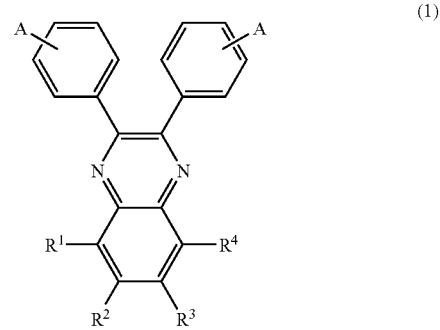

(1)

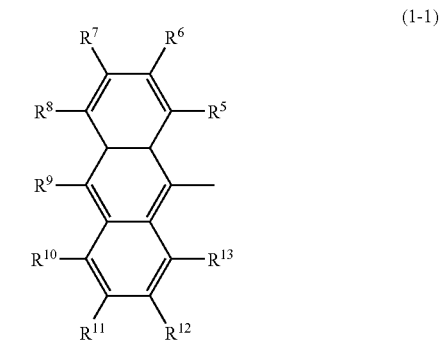

(1-1)

-continued

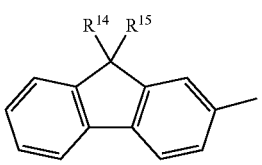
(1-2)

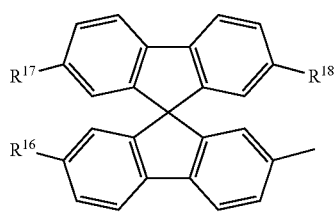
(1-3)

(In the formula, $R^1$ to $R^4$ may be the same or different from each other, and each represent any of a hydrogen atom, an alkyl group with 1 to 4 carbon atoms, or an aryl group with 6 to 25 carbon atoms. In addition, $R^1$ and $R^2$ may be bonded to form a condensed ring, as well as $R^2$ and $R^3$, and $R^3$ and $R^4$. A represents any of substituent groups represented by General Formulas (1-1) to (1-3). In General Formulas (1-1) to (1-3), each of $R^5$ to $R^8$ and $R^{10}$ to $R^{13}$ represents a hydrogen atom or an alkyl group with 1 to 4 carbon atoms; $R^9$ represents any of a hydrogen atom, an alkyl group with 1 to 4 carbon atoms, or an aryl group with 6 to 14 carbon atoms; each of $R^{14}$ and $R^{15}$ represents a hydrogen atom, an alkyl group with 1 to 4 carbon atoms, or a phenyl group; and each of $R^{16}$ to $R^{18}$ represents a hydrogen atom or an alkyl group with 1 to 4 carbon atoms.

Another feature of the present invention is a quinoxaline derivative represented by General Formula (2).

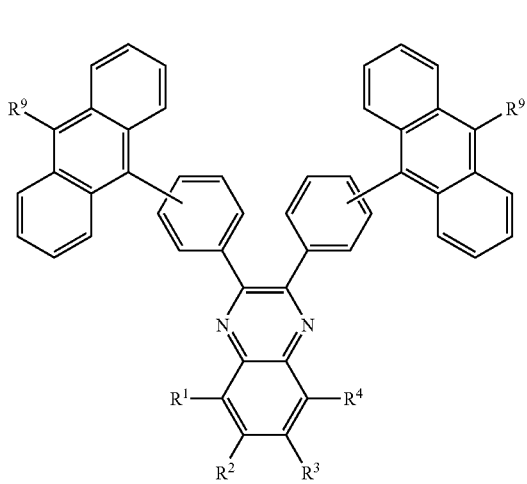
(2)

(In the formula, $R^1$ to $R^4$ may be the same or different from each other, and each represent any of a hydrogen atom, an alkyl group with 1 to 4 carbon atoms, or an aryl group with 6 to 25 carbon atoms. In addition, $R^1$ and $R^2$ may be bonded to form a condensed ring, as well as $R^2$ and $R^3$, and $R^3$ and $R^4$. $R^9$ represents any of a hydrogen atom, an alkyl group with 1 to 4 carbon atoms, or an aryl group with 6 to 14 carbon atoms.)

In the above structure, the quinoxaline derivative represented by General Formula (3) is preferable.

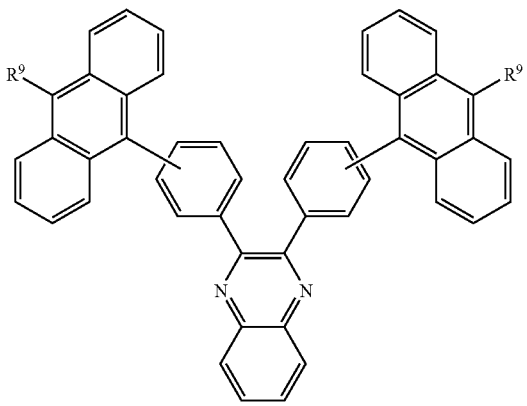
(3)

(In the formula, $R^9$ represents any of a hydrogen atom, an alkyl group with 1 to 4 carbon atoms, or an aryl group with 6 to 14 carbon atoms.)

In particular, the quinoxaline derivative represented by General Formula (4) is preferable.

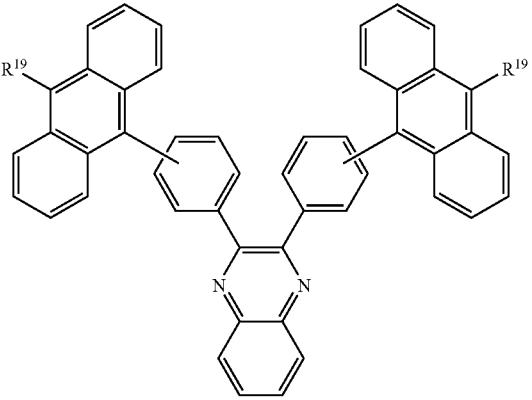
(4)

(In the formula, $R^{19}$ represents a hydrogen atom or a phenyl group.)

The quinoxaline derivative represented by Structural Formula (101) is even more preferable.

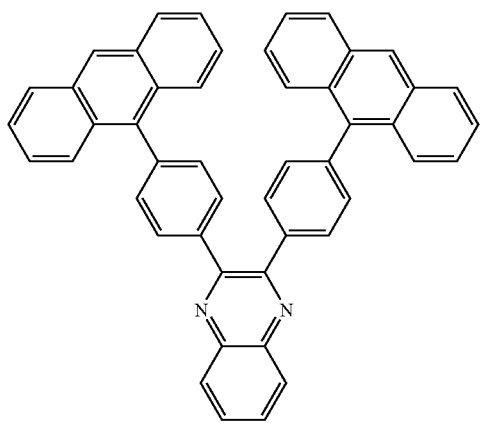

(101)

Also, the quinoxaline derivative represented by Structural Formula (118) is preferable.

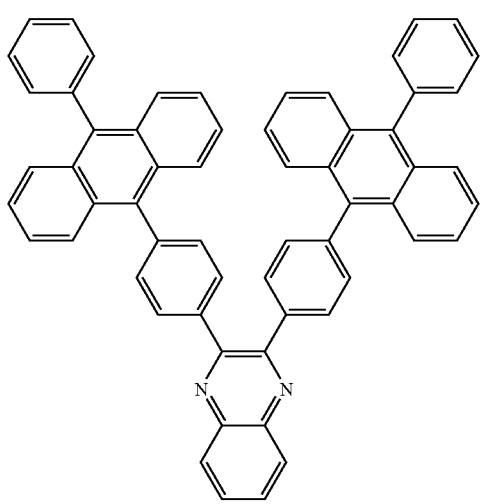

(118)

Further, another feature of the present invention is the quinoxaline derivative represented by General Formula (5).

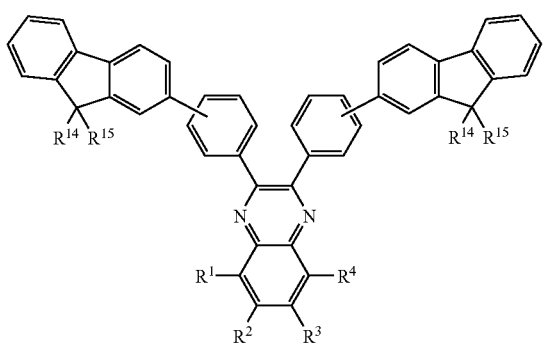

(5)

(In the formula, $R^1$ to $R^4$ may be the same or different from each other, and each represent any of a hydrogen atom, an alkyl group with 1 to 4 carbon atoms or an aryl group with 6 to 25 carbon atoms. In addition, $R^1$ and $R^2$ may be bonded to form a condensed ring, as well as $R^2$ and $R^3$, and $R^3$ and $R^4$. $R^{14}$ and $R^{15}$ may be the same or different from each other, and each represent any of a hydrogen atom, an alkyl group with 1 to 4 carbon atoms, or a phenyl group.)

In the above structure, the quinoxaline derivative represented by General Formula (6) is preferable.

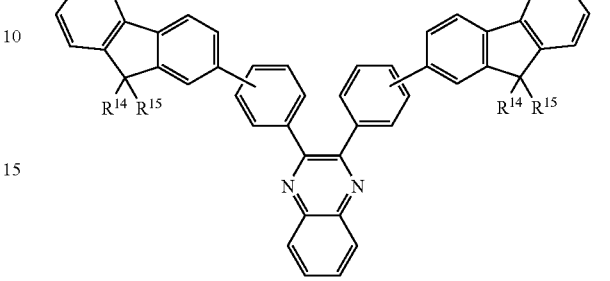

(6)

(In the formula, $R^{14}$ and $R^{15}$ may be the same or different from each other, and each represent a hydrogen atom, an alkyl group with 1 to 4 carbon atoms, or a phenyl group.)

In particular, the quinoxaline derivative represented by General Formula (7) is preferable.

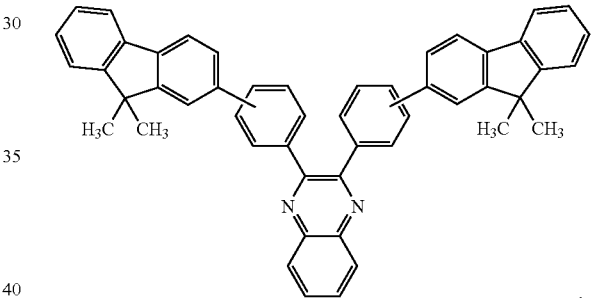

(7)

The quinoxaline derivative represented by Structural Formula (126) is even more preferable.

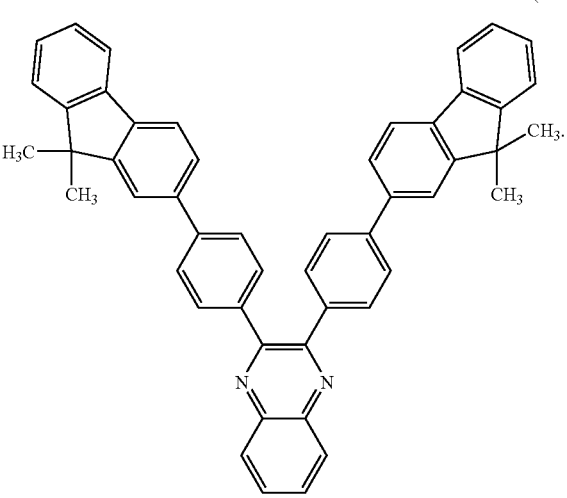

(126)

Another feature of the present invention is the quinoxaline derivative represented by General Formula (8).

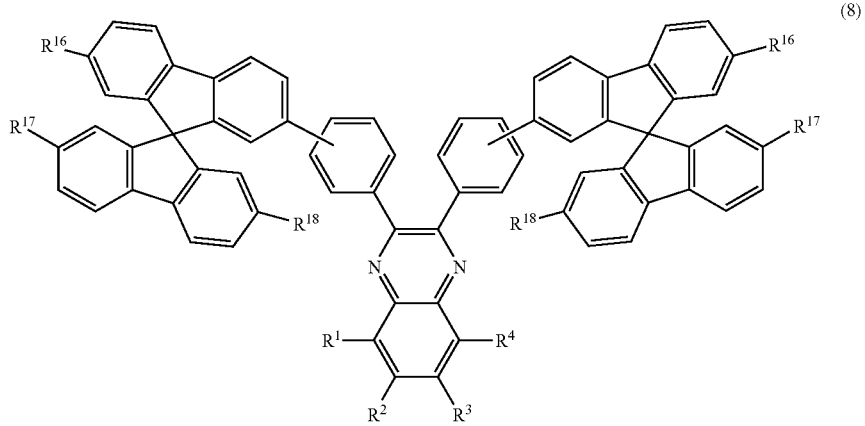

(8)

(In the formula, $R^1$ to $R^4$ may be the same or different from each other, and each represent a hydrogen atom, an alkyl group with 1 to 4 carbon atoms, or an aryl group with 6 to 25 carbon atoms. In addition, $R^1$ and $R^2$ may be bonded to form a condensed ring, as well as $R^2$ and $R^3$, and $R^3$ and $R^4$. $R^{16}$ to $R^{18}$ may be the same or different from each other, and each represent a hydrogen atom or an alkyl group with 1 to 4 carbon atoms.)

In the above structure, the quinoxaline derivative represented by General Formula (9) is preferable.

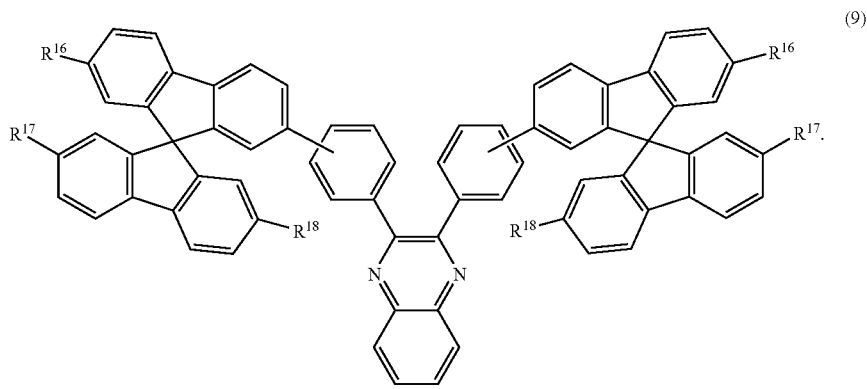

(9)

(In the formula, $R^{16}$ to $R^{18}$ may be the same or different from each other, and each represent a hydrogen atom or an alkyl group with 1 to 4 carbon atoms.)

In particular, the quinoxaline derivative represented by General Formula (10) is preferable.

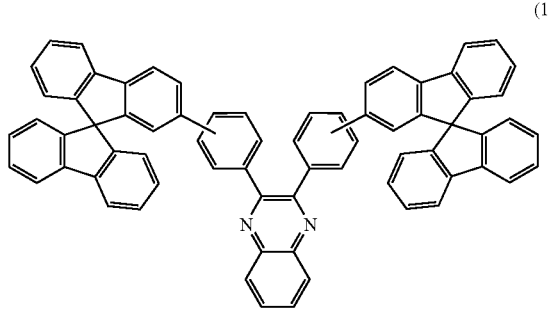

(10)

The quinoxaline derivative represented by Structural Formula (144) is even more preferable.

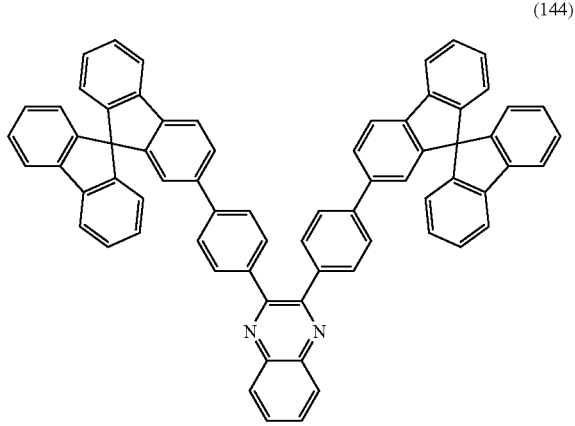

(144)

Also, one feature of the present invention is a light-emitting element using the foregoing quinoxaline derivative. Specifically, the light-emitting element includes the foregoing quinoxaline derivative between a pair of electrodes.

Another feature of the present invention is a light-emitting element including the foregoing quinoxaline derivative between a pair of electrodes, and the quinoxaline derivative emits light when voltage is applied between the pair of electrodes.

Another feature of the present invention is a light-emitting element including a light-emitting layer between a pair of electrodes, and the light-emitting layer includes the foregoing quinoxaline derivative.

Yet another feature of the present invention is a light-emitting element including a light-emitting layer between a pair of electrodes, and the light-emitting layer includes the foregoing quinoxaline derivative and a fluorescence emitting substance.

Still another feature of the present invention is a light-emitting element including a light-emitting layer between a pair of electrodes, and the light-emitting layer includes the foregoing quinoxaline derivative and a phosphorescence emitting substance.

Further, a light-emitting device of the present invention has a light-emitting element including the above quinoxaline derivative between a pair of electrodes and a controller for controlling light emission of the light-emitting element. The light-emitting device in this specification includes an image display device, a light-emitting device, and a light source (including a lighting system). Further, the light-emitting device also includes a module in which a connector such as an FPC (Flexible Printed Circuit), a TAB (Tape Automated Bonding) tape, or a TCP (Tape Carrier Package) is attached to a panel, a module in which a printed wiring board is provided at an end of a TAB tape or a TCP, and a module in which an IC (Integrated Circuit) is directly mounted on the light-emitting device by a COG (Chip On Glass) method.

The quinoxaline derivative of the present invention is an organic compound capable of emitting visible light.

Also, since the quinoxaline derivative of the present invention is capable of emitting visible light, it can be favorably used for a light-emitting element. In particular, since the quinoxaline derivative of the present invention exhibits a broad emission spectrum when it is used for a light-emitting element, by using it for a light-emitting element, a light-emitting element that gives white light emission with an excellent color rendering property can be obtained.

In addition, by using the light-emitting element of the present invention, a light-emitting device with an excellent color rendering property can be obtained.

BRIEF DESCRIPTION OF DRAWINGS

In the following drawings.

DETAILED DESCRIPTION OF THE INVENTION

Embodiment Mode

Figure 1A:
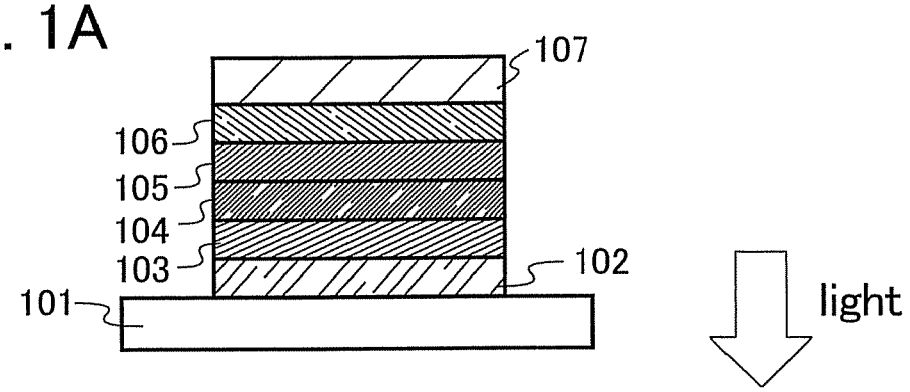
FIGS. 1A to 1C are views explaining a light-emitting element of the present invention.

Hereinafter, embodiment modes of the present invention will be described in detail with reference to the accompanying drawings. However, the present invention is not limited to the following description, and it is easily understood by those skilled in the art that various changes and modifications are possible, unless such changes and modifications depart from the content and the scope of the invention. Therefore, the present invention is not construed as being limited to the description of the following Embodiment Modes.

Embodiment Mode 1

A quinoxaline derivative of the present invention is represented by General Formula (I) below.

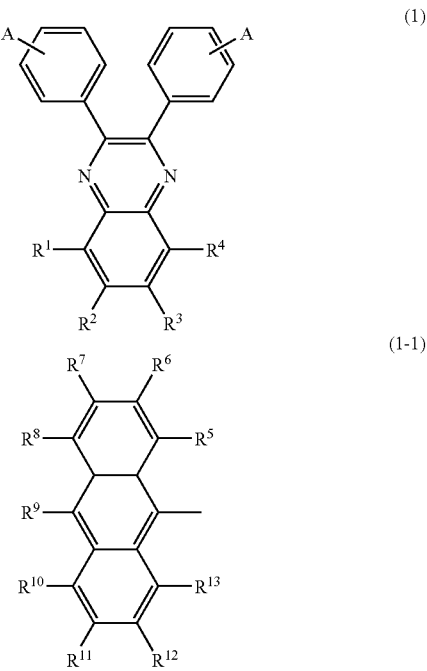

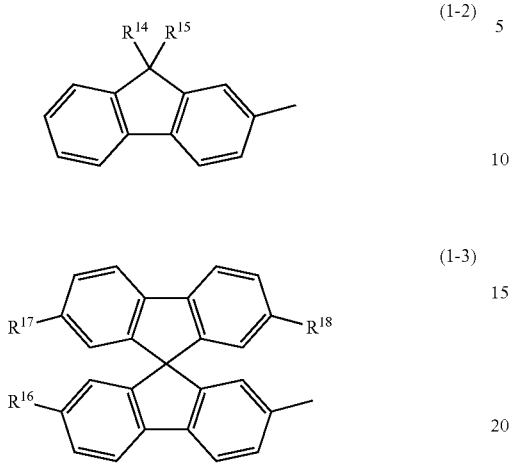

(1-2)

(1-3)

(In the formula, $R^1$ to $R^4$ may be the same or different from each other, and each represent any of a hydrogen atom, an alkyl group with 1 to 4 carbon atoms, or an aryl group with 6 to 25 carbon atoms. In addition, $R^1$ and $R^2$ may be bonded to form a condensed ring, as well as $R^2$ and $R^3$, and $R^3$ and $R^4$. A represents any of substituent groups represented by General Formulas (1-1) to (1-3). In General Formulas (1-1) to (1-3), each of $R^5$ to $R^8$ and $R^{10}$ to $R^{13}$ represents a hydrogen atom or an alkyl group with 1 to 4 carbon atoms; $R^9$ represents any of a hydrogen atom, an alkyl group with 1 to 4 carbon atoms, or an aryl group with 6 to 14 carbon atoms; each of $R^{14}$ and $R^{15}$ represents a hydrogen atom, an alkyl group with 1 to 4 carbon atoms, or a phenyl group; and each of $R^{16}$ to $R^{18}$ represents a hydrogen atom or an alkyl group with 1 to 4 carbon atoms.)

In General Formula (1) above, A, which is bonded to a phenyl group, may be bonded in any position of an ortho-position, a meta-position, or a para-position with respect to a quinoxaline skeleton.

In General Formula (1) above, as an alkyl group with 1 to 4 carbon atoms, a methyl group, an ethyl group, an isopropyl group, a tert-butyl group, and the like are given.

In addition, in General Formula (1) above, as an aryl group with 6 to 25 carbon atoms, substituent groups represented by Structural Formulas (11-1) to (11-9) are given.

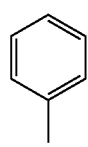

(11-1)

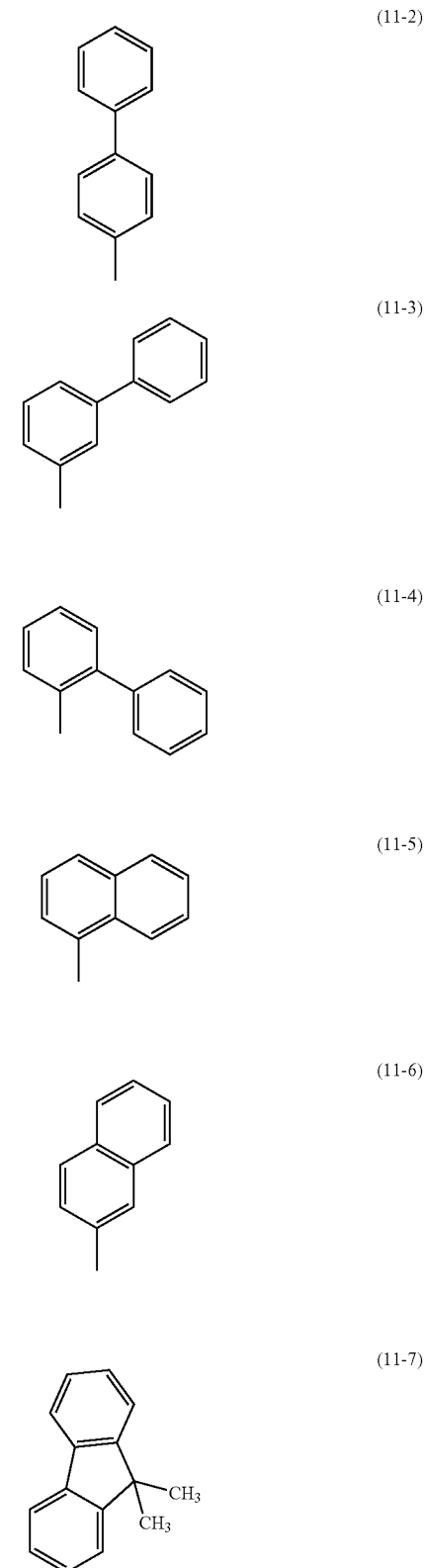

-continued

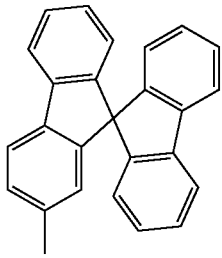
(11-8)

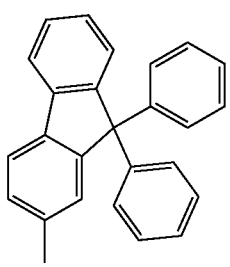
(11-9)

In the quinoxaline derivative represented by General Formula (1), the quinoxaline derivative represented by General Formula (2) below is preferable.

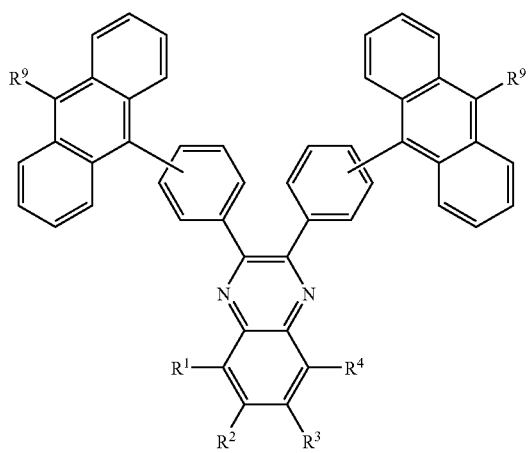
(2)

(In the formula, $R^1$ to $R^4$ may be the same or different from each other, and each represent any of a hydrogen atom, an alkyl group with 1 to 4 carbon atoms, or an aryl group with 6 to 25 carbon atoms. In addition, $R^1$ and $R^2$ may be bonded to form a condensed ring, as well as $R^2$ and $R^3$, and $R^3$ and $R^4$. $R^9$ represents any of a hydrogen atom, an alkyl group with 1 to 4 carbon atoms, or an aryl group with 6 to 14 carbon atoms.)

In the quinoxaline derivative represented by General Formula (2), the quinoxaline derivative represented by General Formula (3) below is preferable.

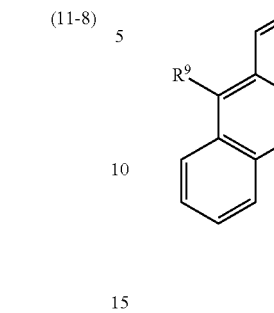
(3)

(In the formula, $R^9$ represents any of a hydrogen atom, an alkyl group with 1 to 4 carbons, or an aryl group with 6 to 14 carbon atoms.)

In particular, the quinoxaline derivative represented by General Formula (4) is preferable.

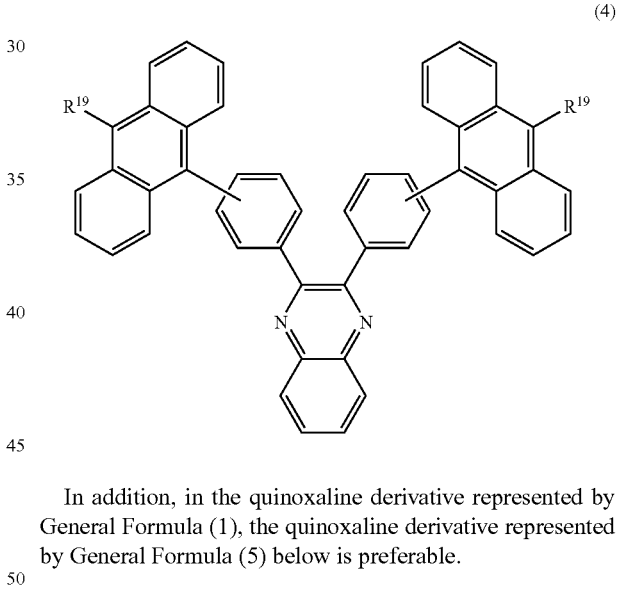
(4)

In addition, in the quinoxaline derivative represented by General Formula (1), the quinoxaline derivative represented by General Formula (5) below is preferable.

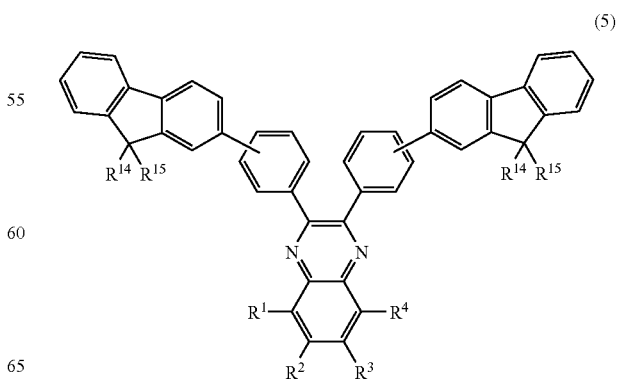
(5)

(In the formula, $R^1$ to $R^4$ may be the same or different from each other, and each represent any of a hydrogen atom, an alkyl group with 1 to 4 carbon atoms, or an aryl group with 6 to 25 carbon atoms. In addition, $R^1$ and $R^2$ may be bonded to form a condensed ring, as well as $R^2$ and $R^3$, and $R^3$ and $R^4$. $R^{14}$ to $R^{15}$ may be the same or different from each other, and each represent any of a hydrogen atom, an alkyl group with 1 to 4 carbon atoms, or a phenyl group.)

In the quinoxaline derivative represented by General Formula (5), the quinoxaline derivative represented by General Formula (6) is preferable.

(In the formula, $R^{14}$ to $R^{15}$ may be the same or different from each other, and each represent any of a hydrogen atom, an alkyl group with 1 to 4 carbon atoms, or a phenyl group.)

In particular, the quinoxaline derivative represented by General formula (7) is preferable.

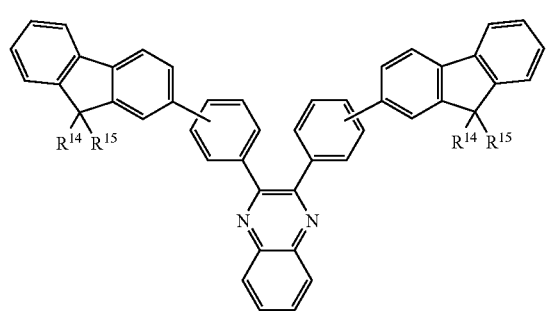

(6)

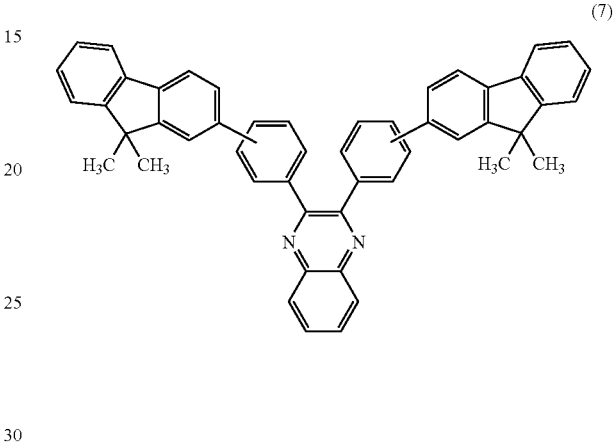

(7)

In addition, in the quinoxaline derivative represented by General Formula (1), the quinoxaline derivative represented by General Formula (8) below is preferable.

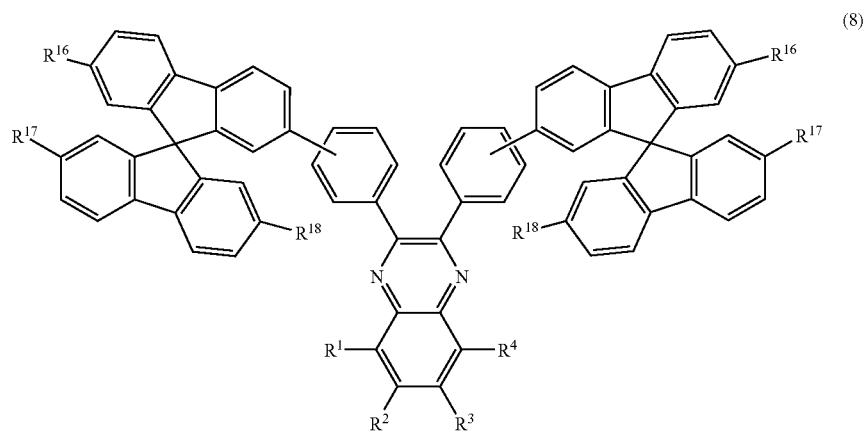

(8)

(In the formula, $R^1$ to $R^4$ may be the same or different from each other, and each represent any of a hydrogen atom, an alkyl group with 1 to 4 carbon atoms, or an aryl group with 6 to 25 carbon atoms. In addition, $R^1$ and $R^2$, $R^2$ and $R^3$, and $R^3$ and $R^4$ may be bonded so that each pair forms a condensed ring. $R^{16}$ to $R^{18}$ may be the same or different from each other, and each represent any of a hydrogen atom, or an alkyl group with 1 to 4 carbon atoms.)

In the quinoxaline derivative represented by General Formula (8), the quinoxaline derivative represented by General Formula (9) is preferable.

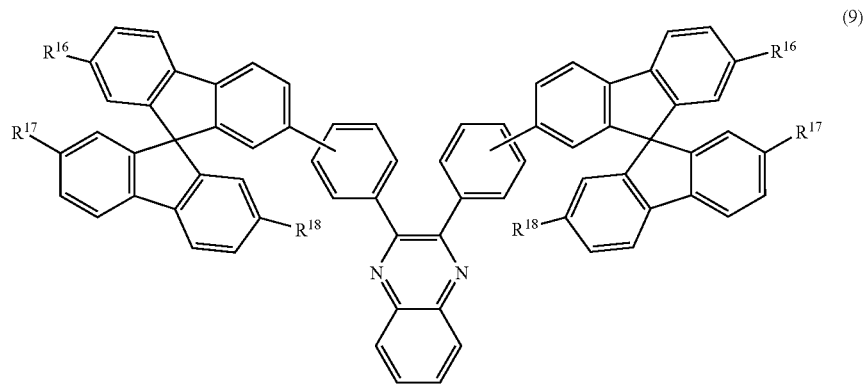

(9)

(In the formula, $R^{16}$ to $R^{18}$ may be the same or different from each other, and each represent a hydrogen atom or an alkyl group with 1 to 4 carbon atoms.)

In particular, the quinoxaline derivative represented by General Formula (10) is preferable.

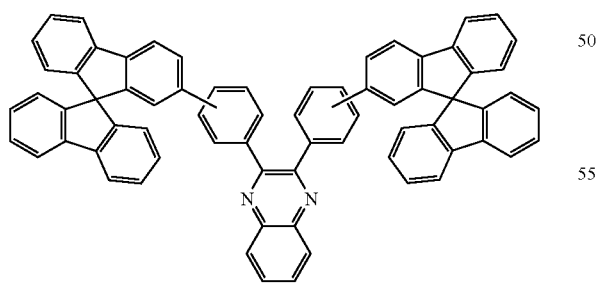

(10)

In addition, as specific examples of a quinoxaline derivative of the present invention, the quinoxaline derivatives shown by Structural Formulas (101) to (160) are given. However, the present invention is not limited thereto.

(101)
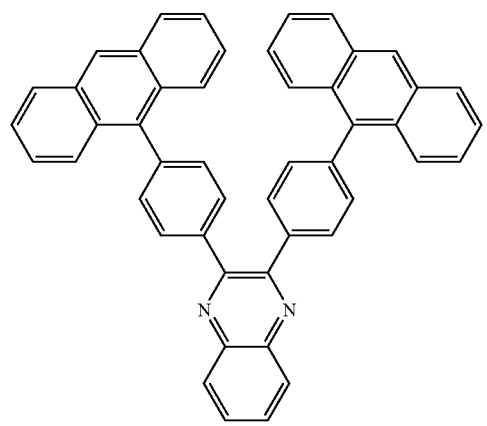
(102)
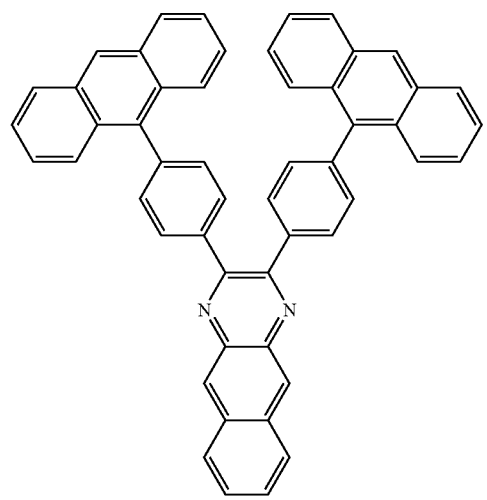
(103)
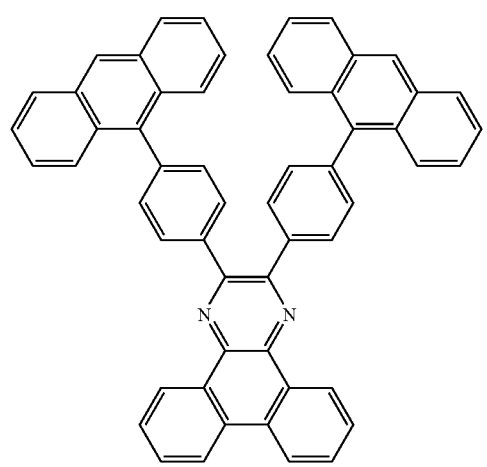
(104)
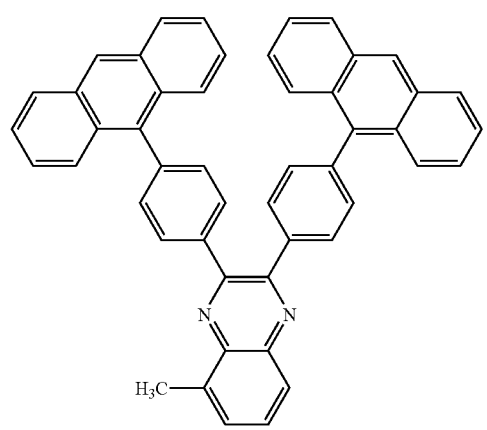
(102)
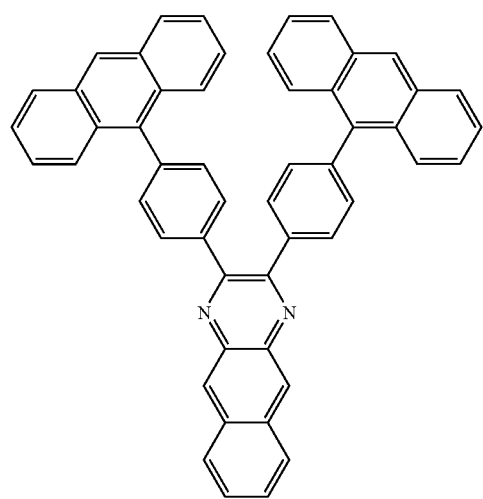
(103)
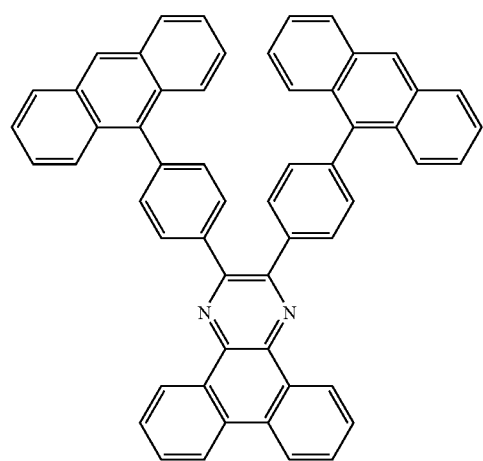

-continued
(104)
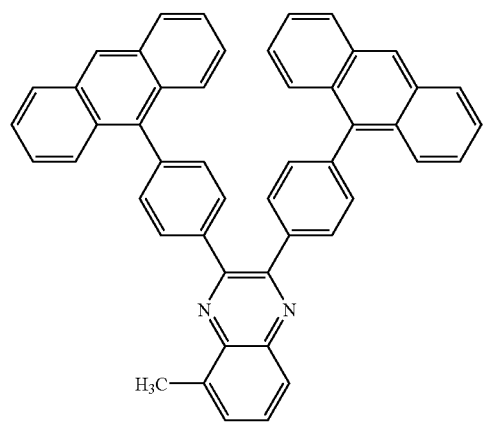
(105)
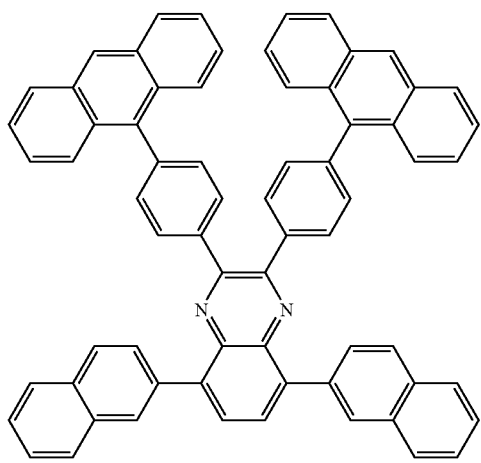
(109)
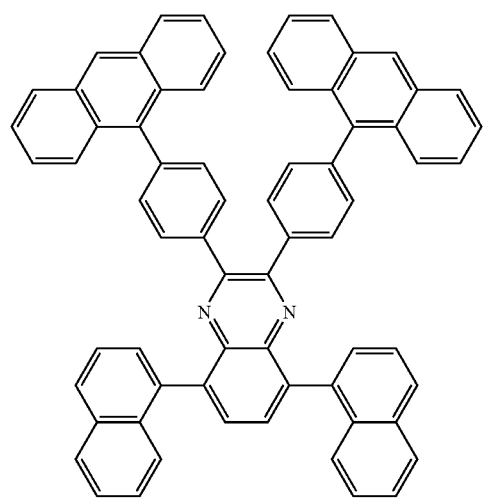
(110)
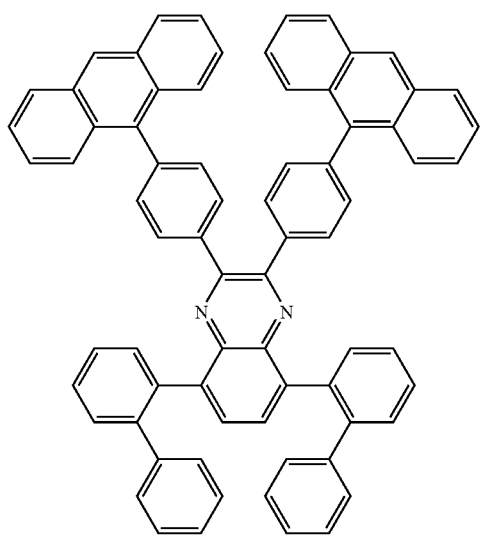
(111)
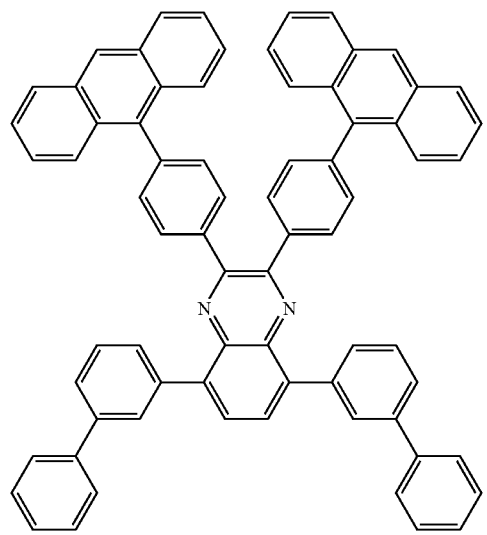
(112)
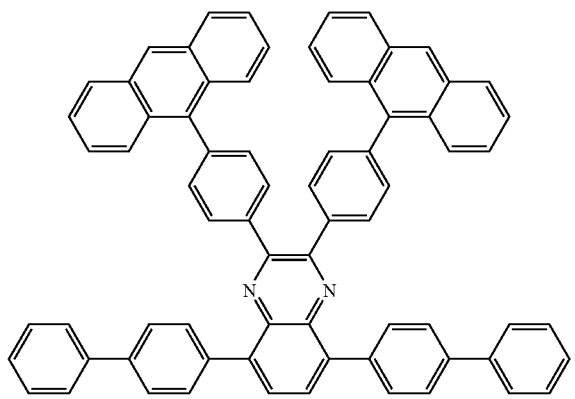

-continued
(113)
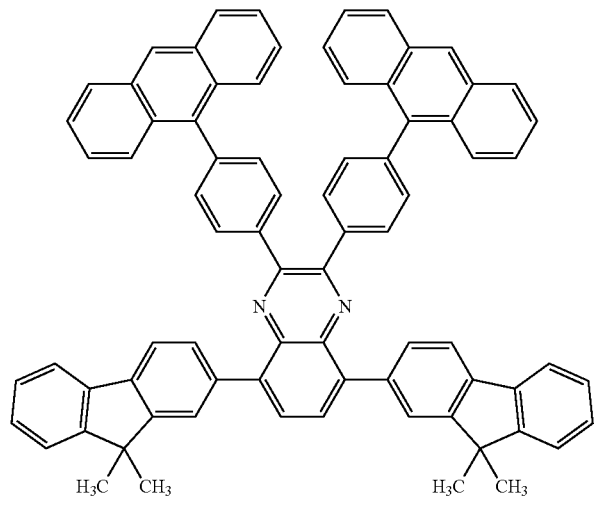
(114)
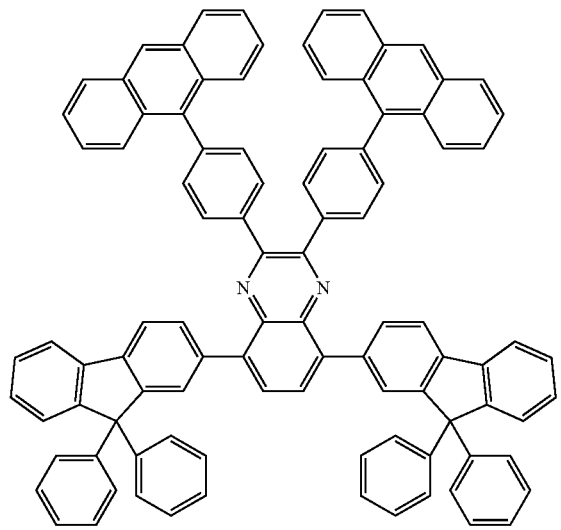
(115)
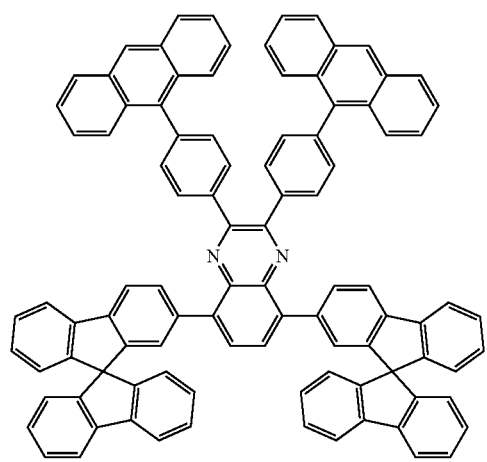
(116)
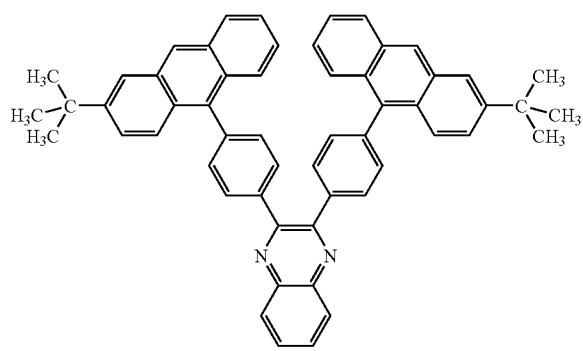
(117)
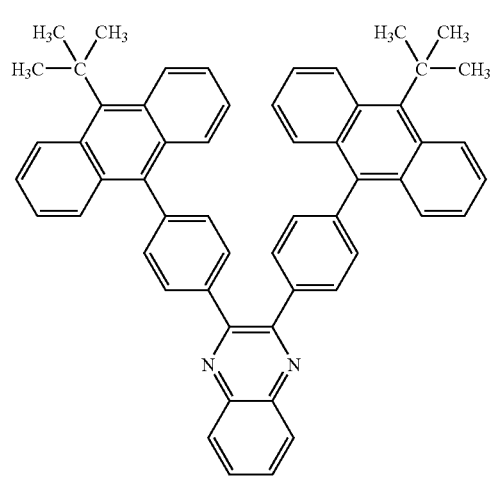
(118)
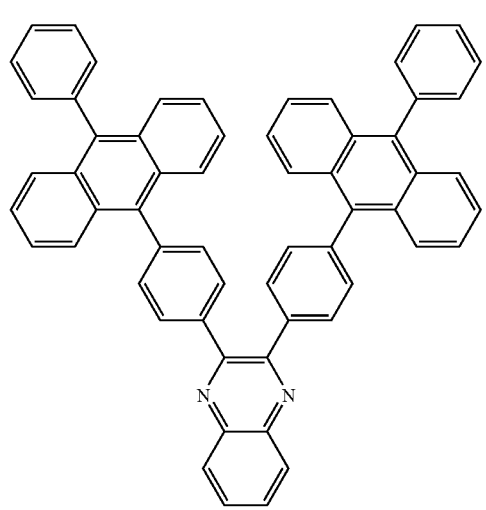

-continued
(119)
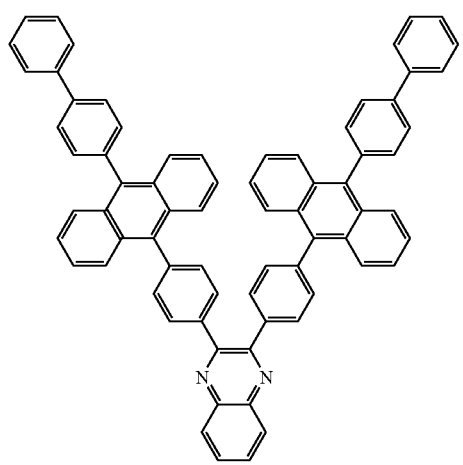
(120)
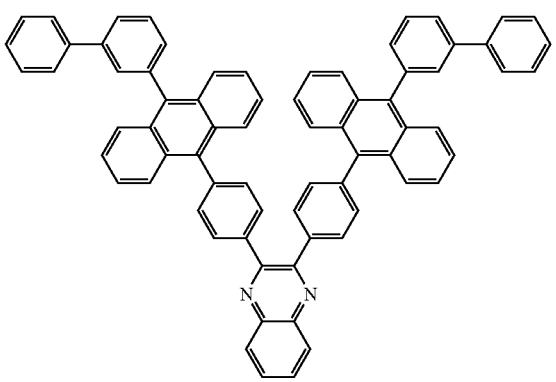
(121)
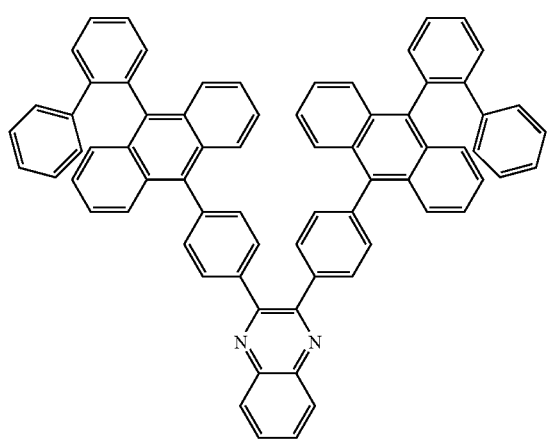
(122)
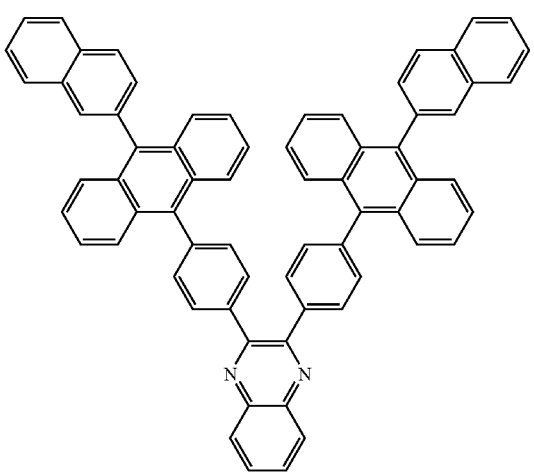
(123)
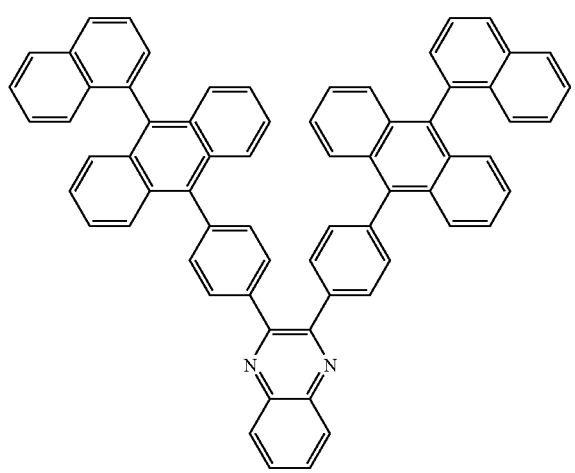
(124)
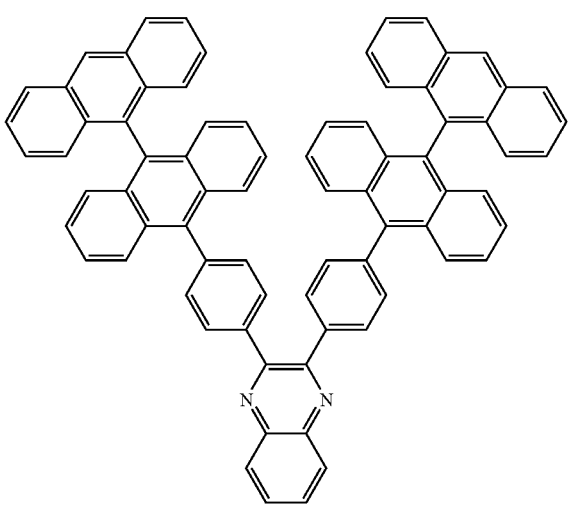

-continued
(125)
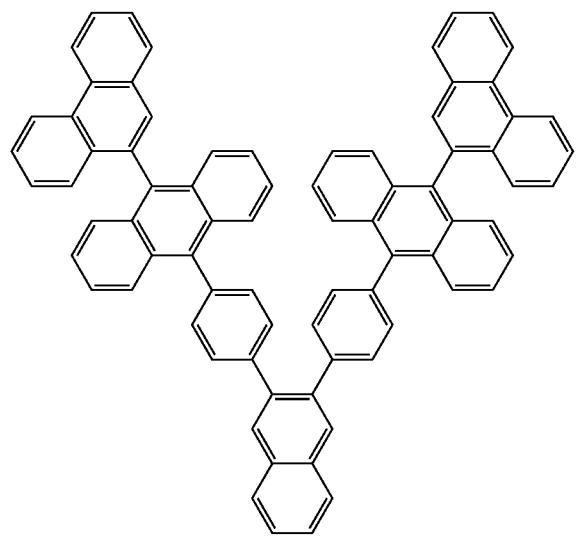
(126)
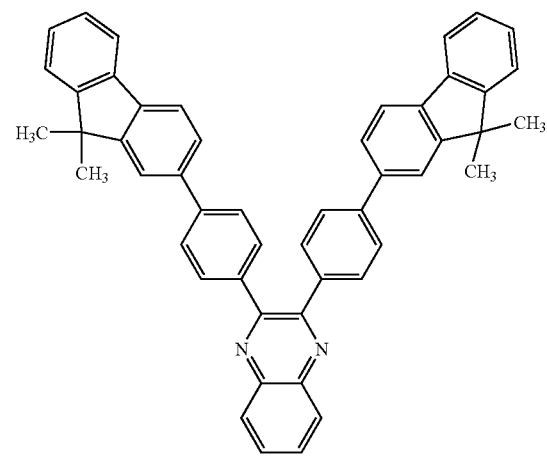
(127)
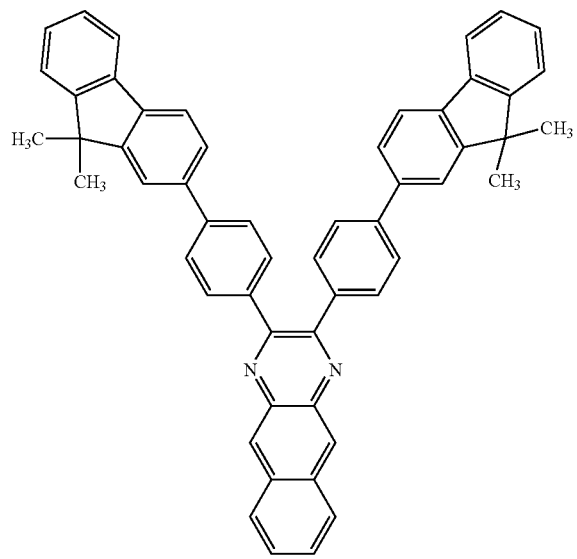
(128)
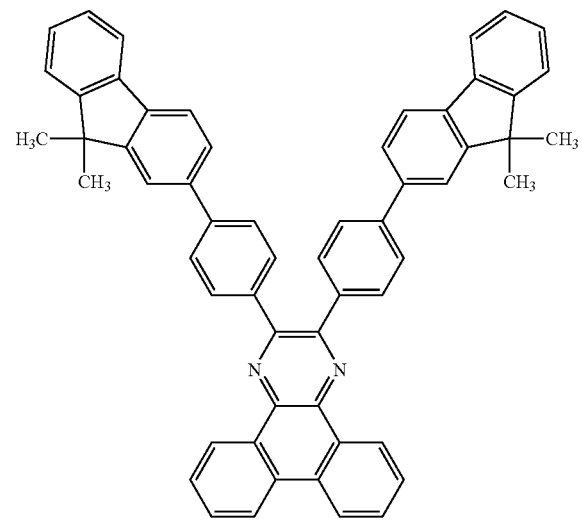
(129)
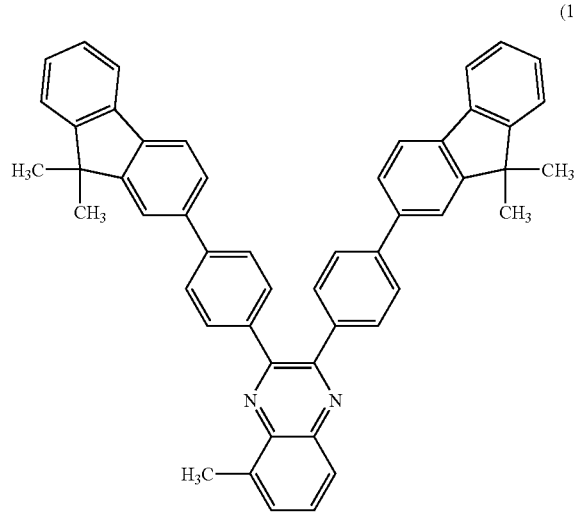
(130)
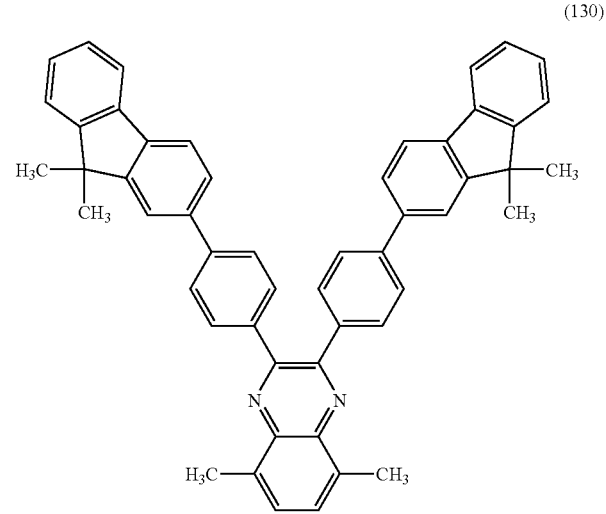

(131)
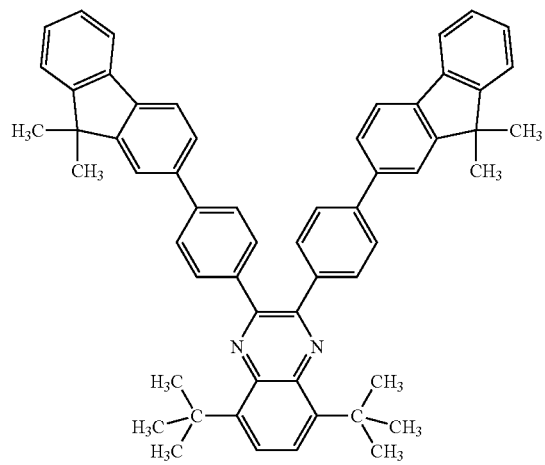
(132)
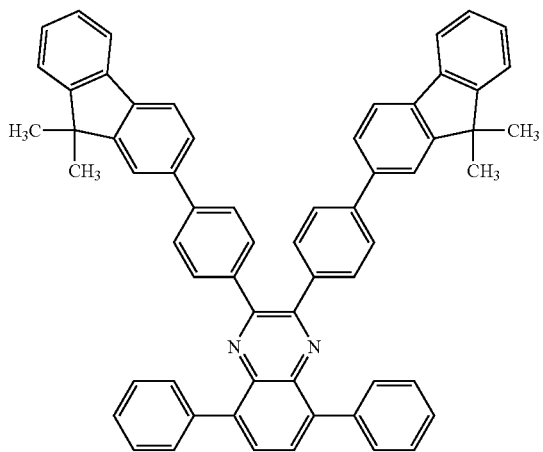
(133)
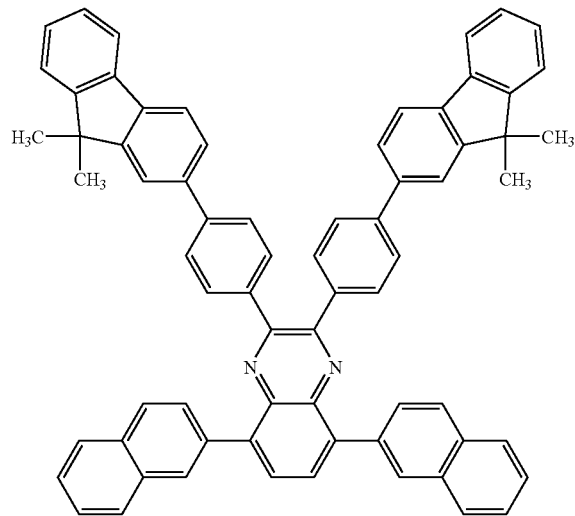
(134)
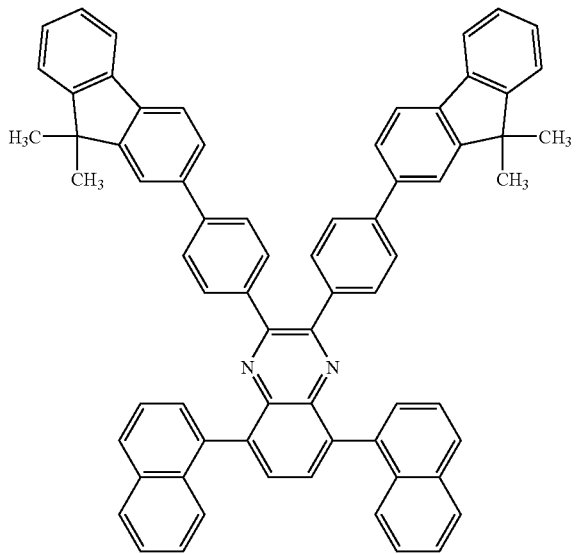

(135)
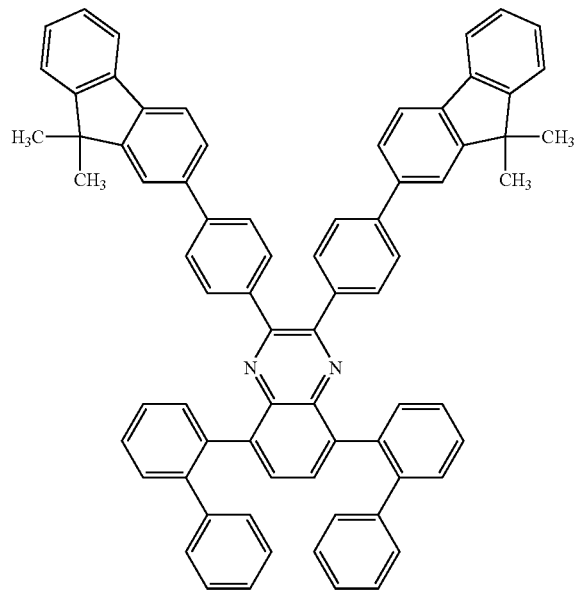
(136)
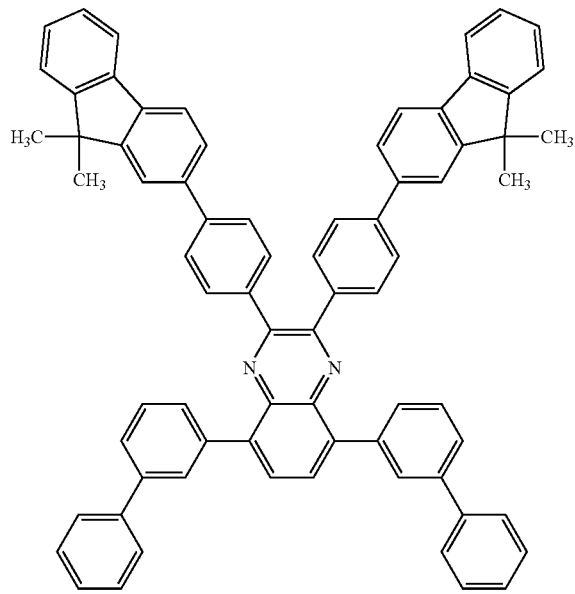
(137)
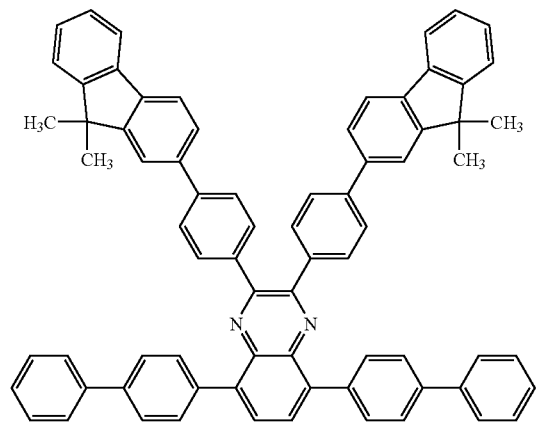
(138)
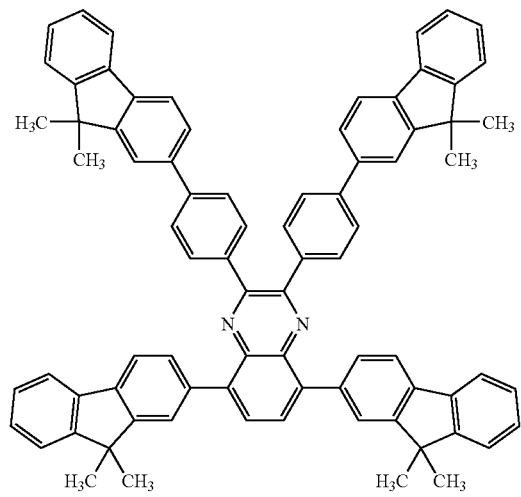

-continued
(139)
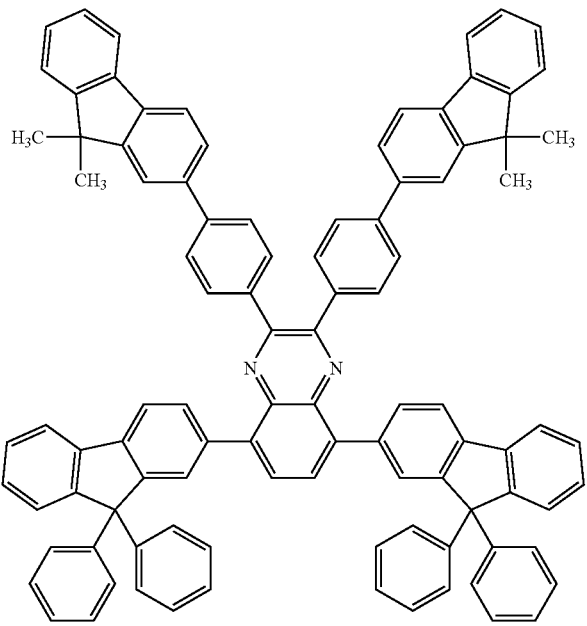
(140)
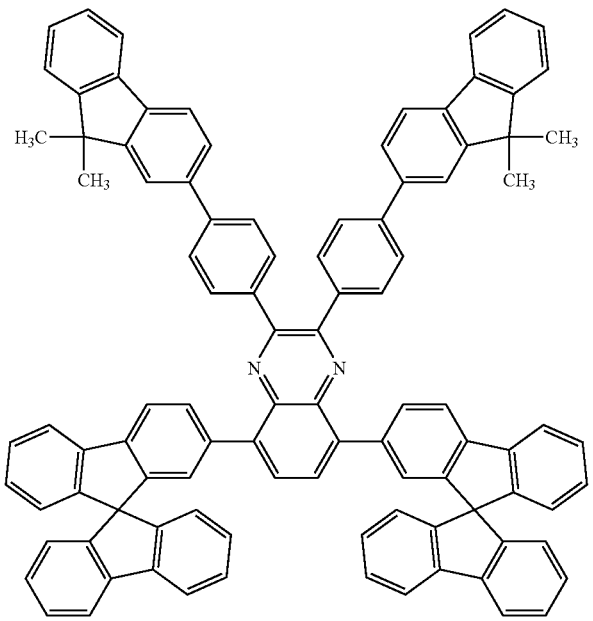
(141)
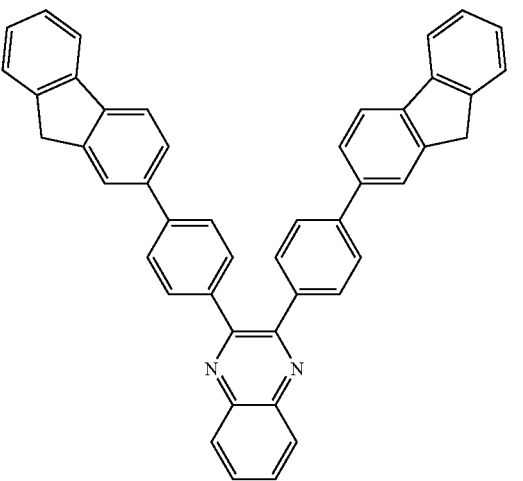
(142)
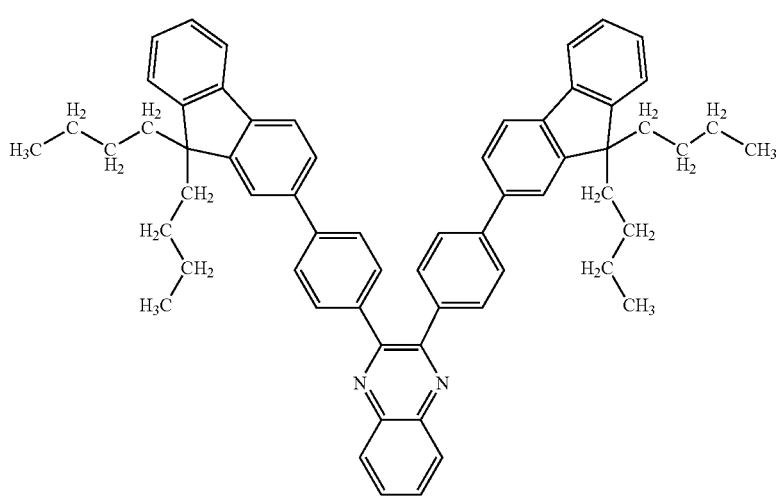

-continued
(143)
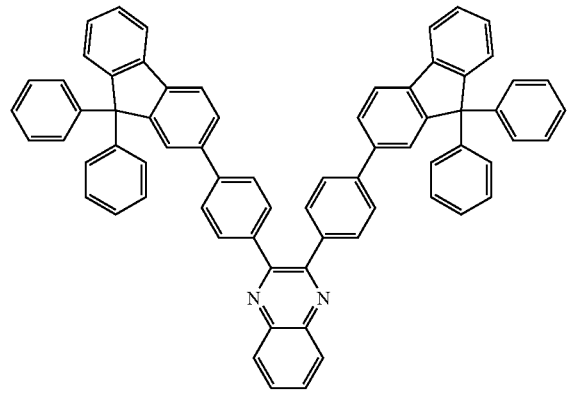
(144)
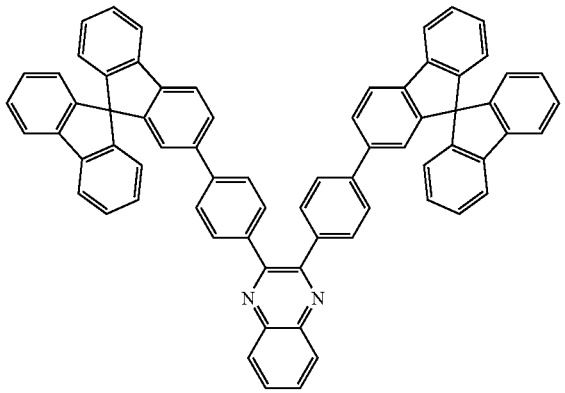
(145)
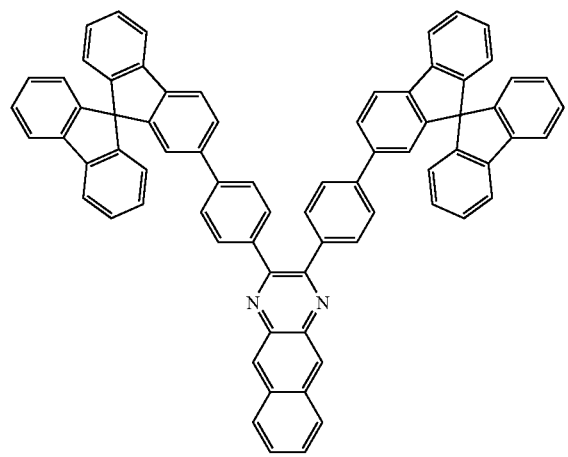
(146)
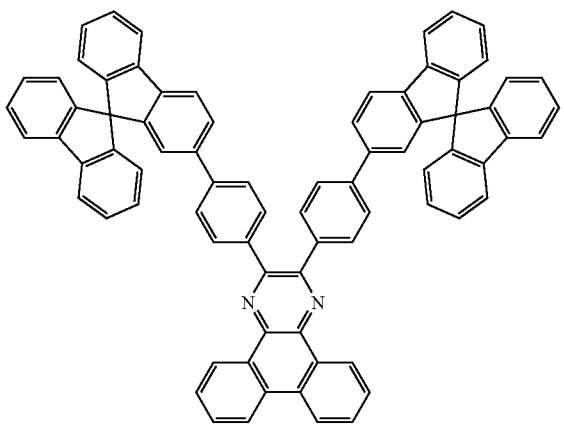
(147)
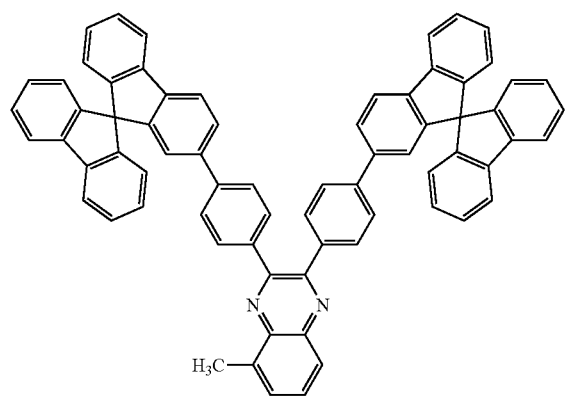
(148)
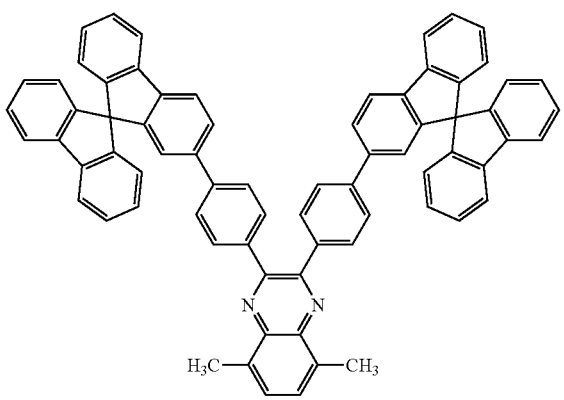

-continued
(149)
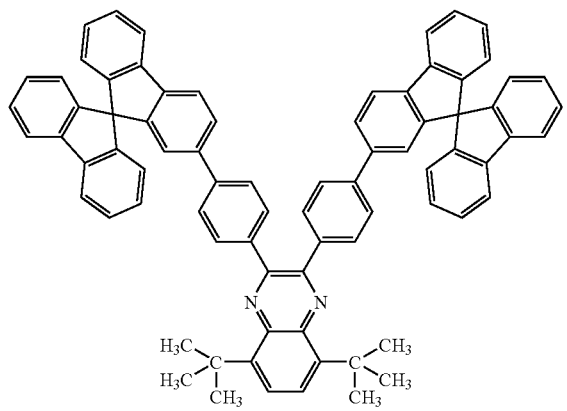
(150)
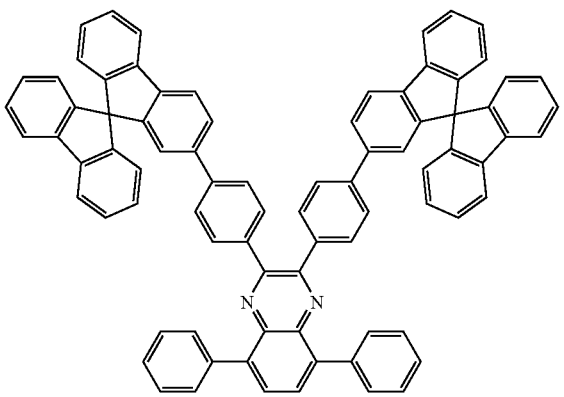
(151)
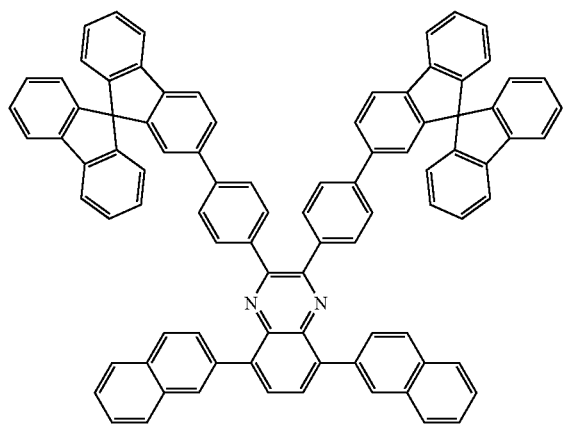
(152)
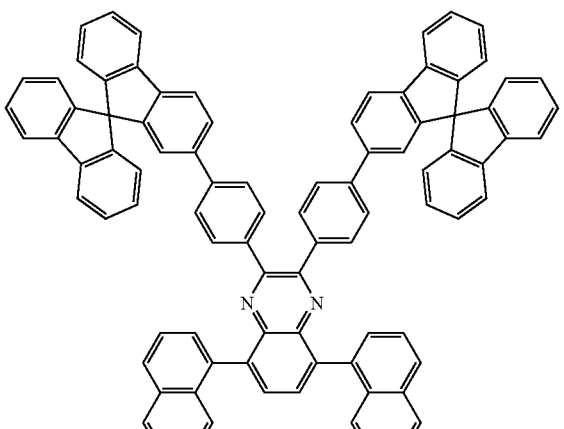
(153)
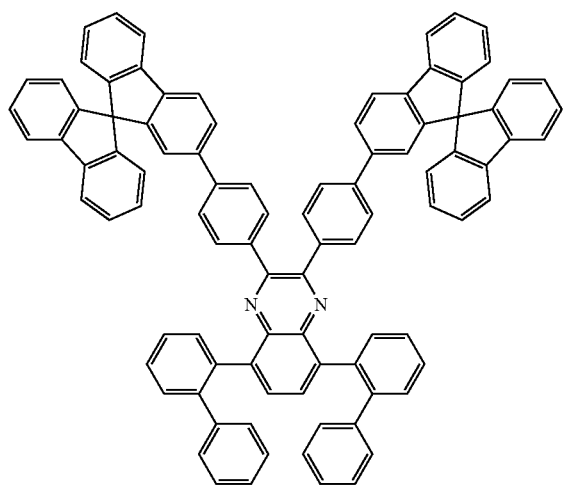
(154)
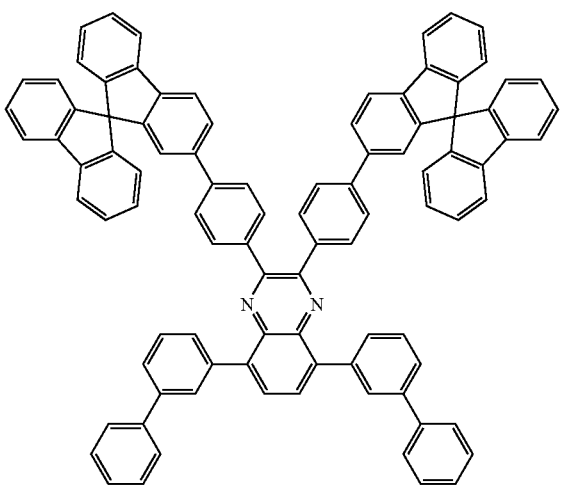

-continued
(155)
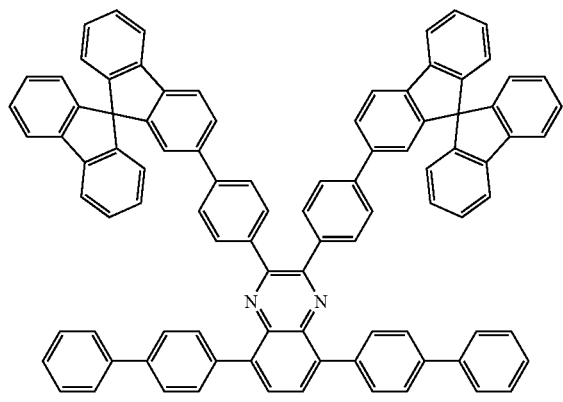
(156)
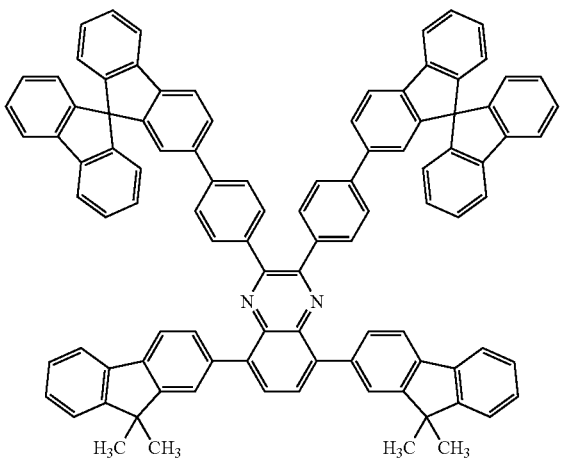
(157)
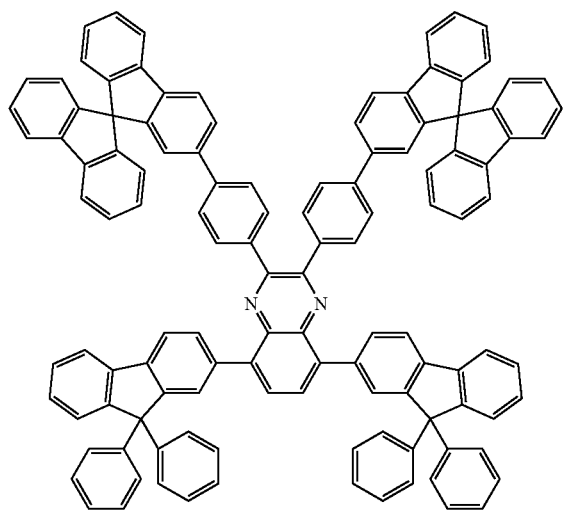
(158)
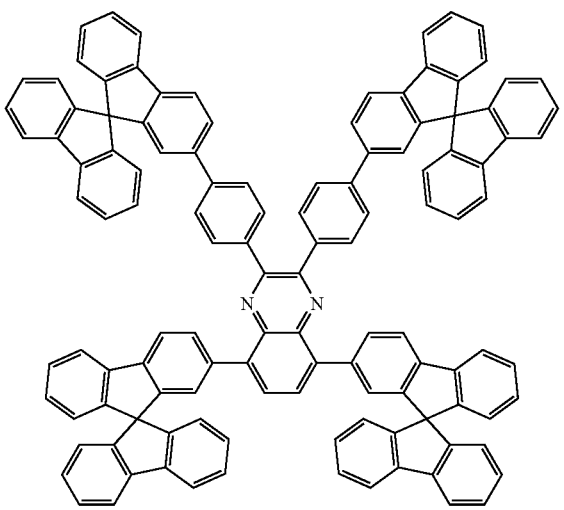
(159)
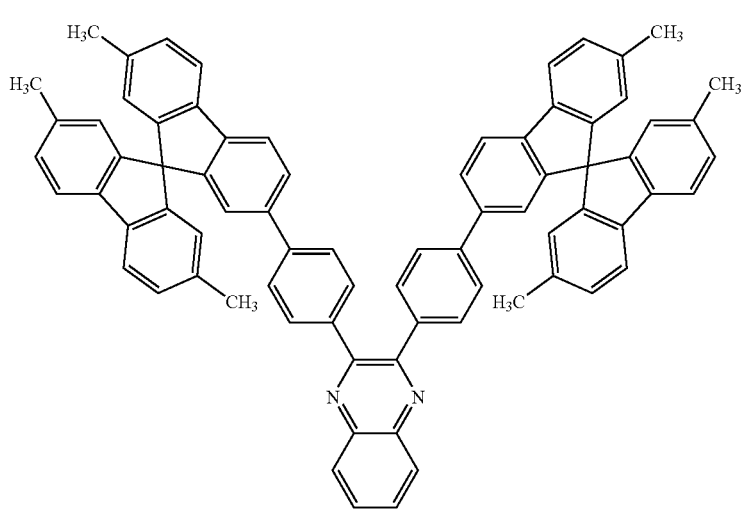

(160)

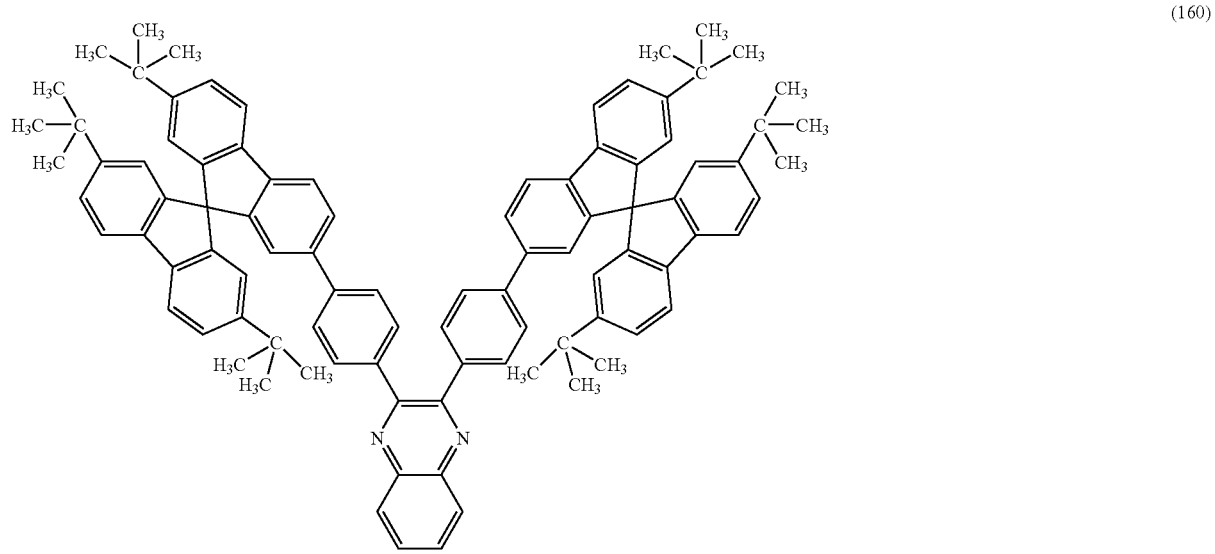

As a synthesis method of a quinoxaline derivative of the present invention, various reactions can be applied. For example, the quinoxaline derivative can be manufactured by performing a synthesis reaction shown in Synthesis Schemes (A-1) to (A-4) below.

First, as shown in Synthesis Scheme (A-1), a quinoxaline skeleton is formed by a condensation reaction between benzyl that is substituted with halogen atoms $X^1$ and $X^2$ (compound B), and 1,2-diaminobenzene derivative (compound A). As the halogen atom, bromine, iodine, and chlorine are given. Bromine or iodine is preferable when easiness of handling and appropriate reactivity are taken into consideration.

(A-1)

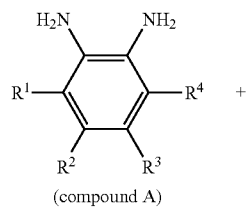
(compound A)

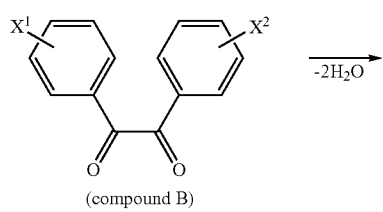
(compound B)

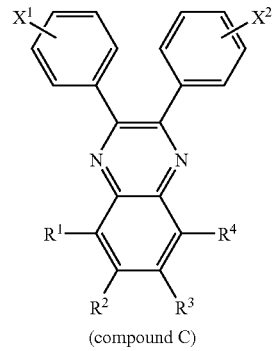
(compound C)

(In Synthesis Scheme (A-1), $X^1$ and $X^2$ may be the same or different from each other, and each represent a halogen atom. $R^1$ to $R^4$ may be the same or different from each other, and each represent a hydrogen atom, an alkyl group with 1 to 4 carbon atoms, or an aryl group with 6 to 25 carbon atoms. In addition, $R^1$ and $R^2$, $R^2$ and $R^3$, and $R^3$ and $R^4$ may be bonded so that each pair forms a condensed ring.)

Subsequently, as shown in Synthesis Scheme (A-2), organic lithium is added to halogen-substituted quinoxaline (compound C) that is obtained so that the compound C is lithiated. Then, by reacting the compound C with trimethyl borate or triisopropyl borate, boronic acid of a quinoxaline derivative (compound D) can be obtained.

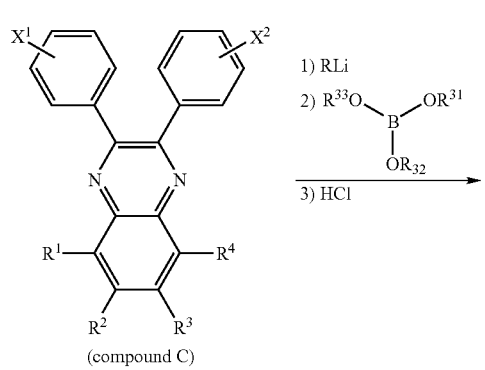 (A-2)

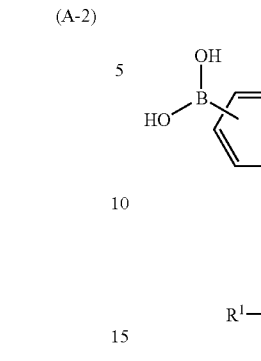

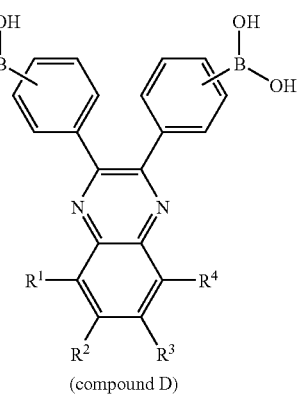 (A-3)

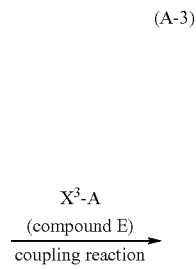

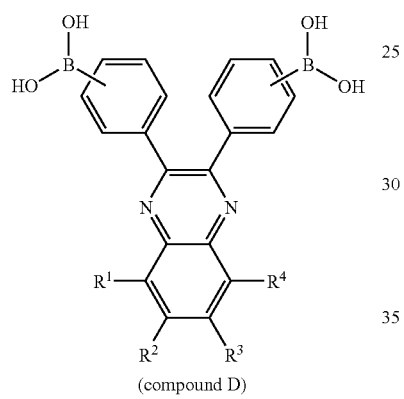

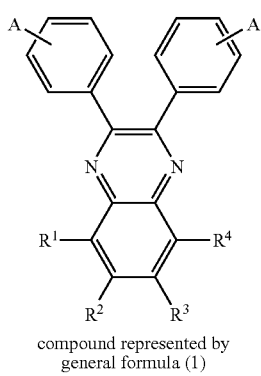

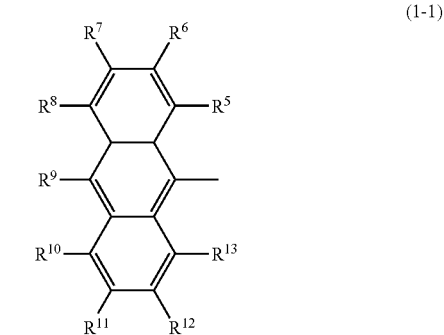 (1-1)

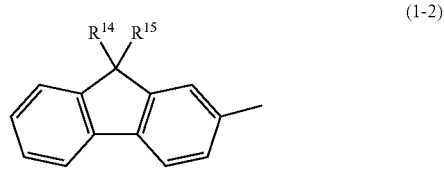 (1-2)

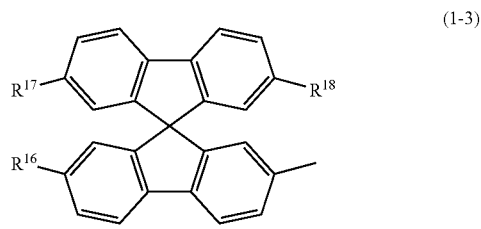 (1-3)

(In Synthesis Scheme (A-2), $X^1$ and $X^2$ may be the same or different from each other, and each represent a halogen atom. As the halogen atom, bromine, iodine, and chlorine are given. Bromine or iodine is preferable when easiness of handling and appropriate reactivity are taken into consideration. $R^1$ to $R^4$ may be the same or different from each other, and each represent any of a hydrogen atom, an alkyl group with 1 to 4 carbon atoms, or an aryl group with 6 to 25 carbon atoms. In addition, $R^1$ and $R^2$, $R^2$ and $R^3$, and $R^3$ and $R^4$ may be bonded so that each pair forms a condensed ring.)

Next, as shown in Synthesis Scheme (A-3), by coupling the boronic acid of a quinoxaline derivative (compound D)) and a halogenated arene (compound E) using a palladium catalyst with an existence of a base, the quinoxaline derivative of the present invention represented by General Formula (1) can be synthesized. For the base, an inorganic base such as potassium carbonate or sodium carbonate, or an organic base such as a metal alkoxide can be used. As the palladium catalyst, palladium(II) acetate, tetrakis(triphenylphosphine)palladium (0), or the like can be used.

In Synthesis Scheme (A-3), $R^1$ to $R^4$ may be the same or different from each other, and each represent any of a hydrogen atom, an alkyl group with 1 to 4 carbon atoms, or an aryl group with 6 to 25 carbon atoms. In addition, $R^1$ and $R^2$, $R^2$ and $R^3$, and $R^3$ and $R^4$ may be bonded so that each pair forms a condensed ring. A represents any of substituent groups represented by General Formulas (1-1) to (1-3). In General Formulas (1-1) to (1-3), each of $R^5$ to $R^8$ and $R^{10}$ to $R^{13}$ represents a hydrogen atom or an alkyl group with 1 to 4 carbon atoms; $R^9$ represents any of a hydrogen atom, an alkyl group with 1 to 4 carbon atoms, or an aryl group with 6 to 14 carbon atoms; each of $R^{14}$ and $R^{15}$ represents a hydrogen atom, an alkyl group with 1 to 4 carbon atoms, or a phenyl group; and each of $R^{16}$ to $R^{18}$ represents a hydrogen atom or an alkyl group with 1 to 4 carbon atoms. Also, $R^{31}$ to $R^{33}$ may be bonded together to form a condensed ring. $X^3$ represents a halogen atom. As the halogen atom, bromine, iodine, and chlorine are given. Bromine or iodine is preferable when easiness of handling and appropriate reactivity are taken into consideration.

In addition, as shown in Synthesis Scheme (A-4), by coupling the halogen-substituted quinoxaline (compound C) and boronic acid of aryl or an organoboron compound of aryl (compound F) using a palladium catalyst with an existence of a base, the quinoxaline derivative of the present invention represented by General Formula (1) can also be synthesized. For the base, an inorganic base such as potassium carbonate or sodium carbonate, or an organic base such as a metal alkoxide can be used. As the palladium catalyst, palladium acetate, palladium chloride, tetrakis(triphenylphosphine)palladium(0), or the like can be used.

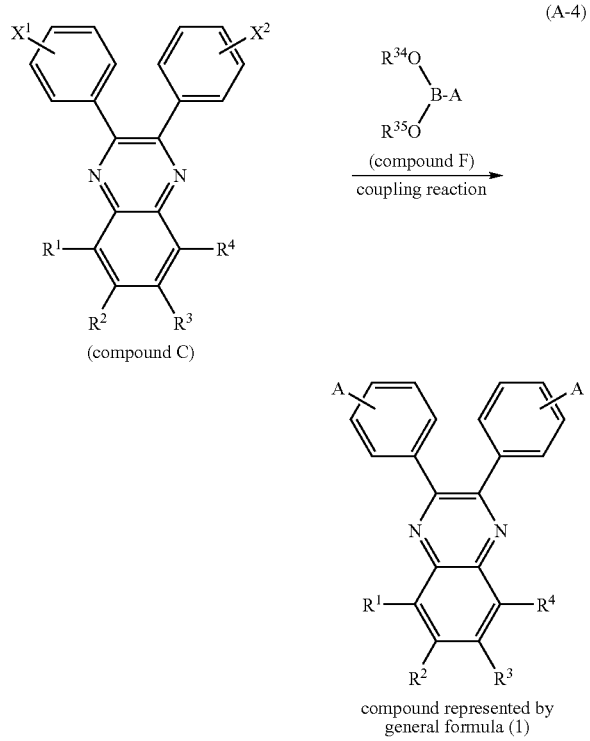

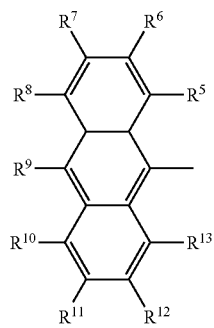

(1-1)

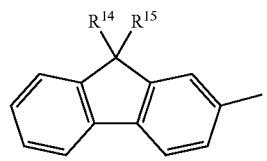

(1-2)

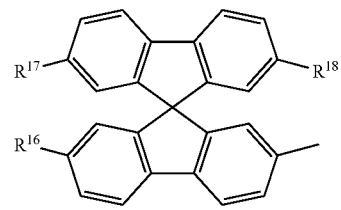

(1-3)

In Synthesis Scheme (A-4), $R^1$ to $R^4$ may be the same or different from each other, and each represent any of a hydrogen atom, an alkyl group, an alkyl group with 1 to 4 carbon atoms, or an aryl group with 6 to 25 carbon atoms. In addition, $R^1$ and $R^2$, $R^2$ and $R^3$, and $R^3$ and $R^4$ may be bonded so that each pair forms a condensed ring. A represents any of substituent groups represented by General Formulas (1-1) to (1-3). In General Formulas (1-1) to (1-3), each of $R^5$ to $R^8$ and $R^{10}$ to $R^{13}$ represents a hydrogen atom or an alkyl group with 1 to 4 carbon atoms; $R^9$ represents any of a hydrogen atom, an alkyl group with 1 to 4 carbon atoms, or an aryl group with 6 to 14 carbon atoms; each of $R^{14}$ and $R^{15}$ represents a hydrogen atom, an alkyl group with 1 to 4 carbon atoms, or a phenyl group; and each of $R^{16}$ to $R^{18}$ represents a hydrogen atom or an alkyl group with 1 to 4 carbon atoms. $R^{34}$ and $R^{35}$ may be the same or different from each other, and each may be a hydrogen atom or an alkyl group with 1 to 10 carbon atoms. Also, $R^{34}$ to $R^{35}$ may be bonded together to form a condensed ring. $X^1$ and $X^2$ may be the same or different from each other, and each represent a halogen atom. As the halogen atom, bromine, iodine, and chlorine are given. Bromine or iodine is preferable when easiness of handling and appropriate reactivity are taken into consideration.

The quinoxaline derivative of the present invention is an organic compound capable of emitting visible light. Accordingly, the quinoxaline derivative of the present invention can favorably be used for a light-emitting element.

Further, the quinoxaline derivative of the present invention gives a broad emission spectrum with a large half bandwidth. Accordingly, by using it for a light-emitting element a light-emitting element that emits light across the entire visible light region can be obtained. Therefore, a light-emitting element that exhibits white light emission with an excellent color rendering property can be obtained.

In addition, the quinoxaline derivative of the present invention can favorably be used for a light-emitting element as a substance that disperses a light-emitting material.

Embodiment Mode 2

In this embodiment mode, one mode of a light-emitting element using the quinoxaline derivative of the present invention is described below with reference to FIGS. 1A to 2.

A light-emitting element of the present invention has a plurality of layers between a pair of electrodes. The plurality of layers are stacked by combining layers formed from a substance with a high carrier injecting property or a substance with a high carrier transporting property, so that a light-emitting region is formed in a place separated from the electrodes, in other words, carriers are recombined in a portion separated from the electrodes. In the present specification, a plurality of layers formed between a pair of electrodes is hereinafter referred to as an EL layer.

In this embodiment mode, a light-emitting element includes a first electrode 102, a first layer 103, a second layer 104, a third layer 105, a fourth layer 106, and a second electrode 107, which are sequentially stacked. It is to be noted that description will be made below in this embodiment mode under the condition that the first electrode 102 serves as an anode and the second electrode 107 serves as a cathode.

A substrate 101 is used as a supporting base of the light-emitting element. For the substrate 101, glass, plastic, or the like can be used, for example. It is to be noted that another material may be used as long as it serves as a supporting base in a manufacturing process of the light-emitting element.

As the first electrode 102, a metal, an alloy, an electrically conductive compound, a mixture thereof, or the like having a high work function (specifically, 4.0 eV or more) is preferably used. Specifically, indium oxide-tin oxide (ITO: Indium Tin Oxide), indium oxide-tin oxide containing silicon or silicon oxide, indium oxide-zinc oxide (IZO: Indium Zinc Oxide), indium oxide containing tungsten oxide and zinc oxide (IWZO), or the like can be given. Although these conductive metal oxide films are generally formed by sputtering, they may be formed by applying a sol-gel method or the like. For example, a film of indium oxide-zinc oxide (IZO) can be formed by a sputtering method using a target in which 1 to 20 wt % of zinc oxide is added to indium oxide. A film of indium oxide containing tungsten oxide and zinc oxide (IWZO) can be formed by a sputtering method using a target in which 0.5 to 5 wt % of tungsten oxide and 0.1 to 1 wt % of zinc oxide are contained in indium oxide. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride: TiN), or the like can be given.

The first layer 103 is a layer including a substance having a high hole-injecting property. Molybdenum oxide (MoOx), vanadium oxide (VOx), ruthenium oxide (RuOx), tungsten oxide (WOx), manganese oxide (MnOx), or the like can be used. Alternatively, the first layer 103 can be formed using phthalocyanine (abbreviation: $H_2Pc$); a phthalocyanine-based compound such as copper phthalocyanine (CuPC); an aromatic amine compound such as 4,4'-bis[N-(4-diphenylaminophenyl)-N-phenylamino]biphenyl (abbreviation: DPAB) or 4,4'-bis(N-{4-[N-(3-methylphenyl)-N-phenylamino]phenyl}-N-phenylamino)biphenyl (abbreviation: DNTPD); or a high molecular material such as poly(ethylene dioxythiophene)/poly(styrenesulfonic acid) (PEDOT/PSS), or the like.

Alternatively, a composite material formed by combining an organic compound and a compound having an electron accepting property with respect to the organic compound can be used for the first layer 103. In particular, a composite material including an organic compound and an inorganic compound having an electron accepting property with respect to the organic compound has an excellent hole-injecting property and hole-transporting property because the electrons are transferred between the organic compound and the inorganic compound, and the carrier density is increased.

In a case of using a composite material formed by combining an organic compound and an inorganic compound for the first layer 103, the first layer 103 can achieve an ohmic contact with the first electrode 102; therefore, a material of the first electrode can be selected regardless of work function.

As the organic compound having an electron accepting property with respect to the organic compound, 7,7,8,8-tetracyanoquinodimethane (abbreviation: TCNQ), 2,3,5,6-tetrafluoro-7,7,8,8-tetracyanoquinodimethane (abbreviation: $F_4TCNQ$), or the like can be used. Further, as the inorganic compound having an electron accepting property with respect to the organic compound, an oxide of a transition metal is preferably used. Moreover, oxides of metals belonging to Groups 4 to 8 in the periodic table can be given. Specifically, it is preferable to use vanadium oxide, niobium oxide, tantalum oxide, chromium oxide, molybdenum oxide, tungsten oxide, manganese oxide, and rhenium oxide, because of their high electron accepting properties. Among them, molybdenum oxide is particularly preferable because it is stable under air, has a low moisture absorption property, and is easily handled.

As the organic compound used for the composite material, various compounds such as an aromatic amine compound, a carbazole derivative, an aromatic hydrocarbon, and a high molecular compound (such as oligomer, dendrimer, or polymer) can be used. The organic compound used for the composite material is preferably an organic compound having a high hole-transporting property. Specifically, a substance having a hole mobility of greater than or equal to $10^{-6}$ $cm^2/Vs$ is preferably used. However, other materials than these materials may also be used as long as the hole-transporting properties thereof are higher than the electron-transporting properties thereof. The organic compounds that can be used for the composite material will be specifically shown below.

For example, the following can be given as the aromatic amine compound: N,N'-di(p-tolyl)-N,N-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N-(3-methylphenyl)-N-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); and the like.

As the carbazole derivatives that can be used for the composite material, the following can be provided specifically: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation-PCzPCA2); 3-[N-(1-naphtyl)-N-(9-phenylcarbazol-3-yl)amino]-9-phenylcarbazole (abbreviation: PCzPCN1); and the like.

Moreover, as the carbazole derivative that can be used for the composite material, the following can be given: 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene; or the like.

As the aromatic hydrocarbon that can be used for the composite material, the following can be given for example: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Besides these compounds, pentacene, coronene, or the like can also be used. In particular, an aromatic hydrocarbon which has a hole mobility of greater than or equal to $1 \times 10^{-6}$ cm$^2$/Vs and which has 14 to 42 carbon atoms is more preferable.

The aromatic hydrocarbon that can be used for the composite material may have a vinyl skeleton. As the aromatic hydrocarbon having a vinyl group, the following are given for example: 4,4'-bis(2,2-diphenylvinyl)biphenyl (abbreviation: DPVBi); 9,10-bis[4-(2,2-diphenylvinyl)phenyl]anthracene (abbreviation: DPVPA); and the like.

Moreover, a high molecular compound such as poly(N-vinylcarbazole) (abbreviation: PVK) or poly(4-vinyltriphenylamine) (abbreviation: PVTPA) can also be used.

As a substance forming the second layer 104, a substance having a high hole-transporting property, specifically, an aromatic amine compound (that is, a compound having a benzene ring-nitrogen bond) is preferable. As a material that is widely used, 4,4'-bis[N-(3-methylphenyl)-N-phenylamino]biphenyl, derivatives thereof such as 4,4'-bis[N-(1-naphthyl)-N-phenylamino]biphenyl (hereinafter referred to as NPB), and star burst aromatic amine compounds such as 4,4',4''-tris(N,N-diphenyl-amino)triphenylamine and 4,4',4''-tris[N-(3-methylphenyl)-N-phenylamino]triphenylamine can be given. These materials described here are mainly substances each having a hole mobility of greater than or equal to $10^{-6}$ cm$^2$/Vs. However, other materials than these compounds may also be used as long as the hole-transporting properties thereof are higher than the electron-transporting properties thereof. The second layer 104 is not limited to a single layer, and a mixed layer of the aforementioned substances, or a stacked layer which comprises two or more layers each including the aforementioned substance may be used.

The third layer 105 is a layer including a substance with a light-emitting property. In this embodiment mode, the third layer 105 includes the quinoxaline derivative of the present invention described in Embodiment Mode 1. Since the quinoxaline derivative of the present invention gives light emission of visible light, it can be favorably used for a light-emitting element as a light-emitting substance.

As the fourth layer 106, a substance having a high electron-transporting property can be used. For example, a layer including a metal complex or the like having a quinoline or benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq) can be used. Alternatively, a metal complex or the like having an oxazole-based or thiazole-based ligand, such as bis[2-(2-hydroxyphenyl)benzoxazolato]zinc (abbreviation: Zn(BOX)$_2$) or bis[2-(2-hydroxyphenyl)-benzothiazolato]zinc (abbreviation: Zn(BTZ)$_2$) can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances described here are mainly substances each having an electron mobility of greater than or equal to $10^{-6}$ cm$^2$/Vs. The electron-transporting layer may be formed using other materials than those described above as long as the materials have higher electron-transporting properties than hole-transporting properties. Furthermore, the electron-transporting layer is not limited to a single layer, and two or more layers in which each layer is made of the aforementioned substance may be stacked.

As a substance forming the second electrode 107, a metal, an alloy, an electrically conductive compound, a mixture thereof, or the like having a low work function (specifically, 3.8 eV or less) is preferably used. As a specific example of such a cathode material, an element belonging to Group 1 or Group 2 in the periodic table, that is, an alkali metal such as lithium (Li) or cesium (Cs), an alkaline earth metal such as magnesium (Mg), calcium (Ca), or strontium (Sr), an alloy including these metals (MgAg, AlLi) can be employed. A rare earth metal such as europium (Eu) or ytterbium (Yb), an alloy including these rare earth metals, or the like is also suitable. However, by providing a layer having a function of promoting electron injection between the second electrode 107 and the fourth layer 106 so that it is stacked with the second electrode, various conductive materials such as Al, Ag, ITO, or ITO containing silicon or silicon oxide can be used for the second electrode 107 regardless of the magnitude of the work function.

As the layer having a function of promoting electron injection, an alkali metal, an alkaline earth metal, or a compound thereof such as lithium fluoride (LiF), cesium fluoride (CsF), or calcium fluoride (CaF$_2$) can be used. For example, a layer which contains substance having an electron-transporting property and an alkali metal, an alkaline earth metal, or a compound thereof (Alq including magnesium (Mg) for example) can be used. It is preferable to use such a layer because electron injection from the second electrode 107 proceeds efficiently.

Various methods can be used for forming the first layer 103, the second layer 104, the third layer 105, and the fourth layer 106. For example, an evaporation method, an ink-jet method, a spin coating method, or the like may be used. Furthermore, each electrode or each layer may be formed by a different film formation method.

By making current flow due to a potential difference generated between the first electrode 102 and the second electrode 107, holes and electrons are recombined in the third layer 105 including a substance with a high light-emitting property, which results in a light-emission from the light-emitting element of the present invention. That is, the light-emitting element of the present invention has a structure in which a light-emitting region is formed in the third layer 105.

Figure 1B:
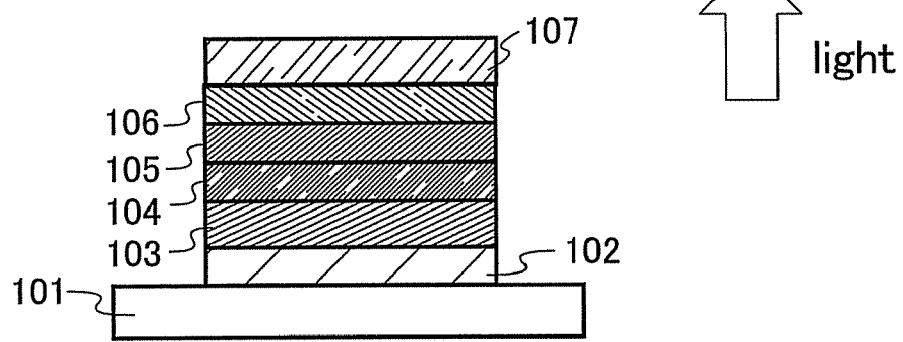
Figure 1C:
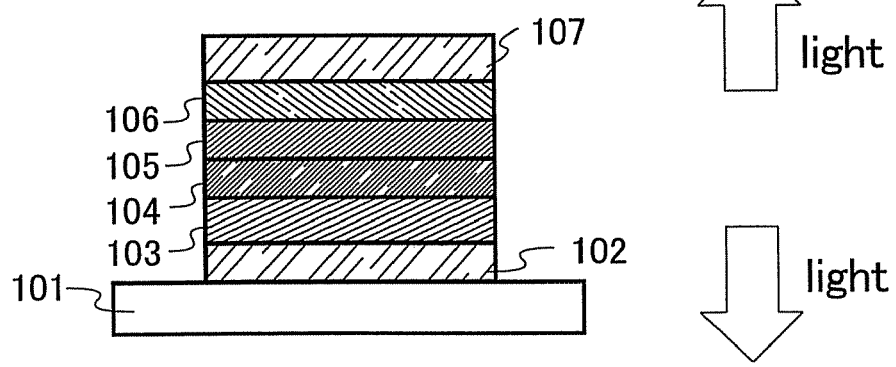

Light emission is extracted outside through one or both of the first electrode 102 and the second electrode 107. Therefore, one or both of the first electrode 102 and the second electrode 107 is/are formed using an electrode having a light transmitting property. In a case where only the first electrode 102 is an electrode having a light transmitting property, light emission is extracted from a substrate side through the first electrode 102 as shown in FIG. 1A. Alternatively, in a case where only the second electrode 107 is an electrode having a light transmitting property, light emission is extracted from the side opposite to the substrate through the second electrode 107 as shown in FIG. 1B. In a case where both of the first electrode 102 and the second electrode 107 are the electrodes having a light transmitting property, light emission is extracted from both of the substrate side and the side opposite to the substrate through the first electrode 102 and the second electrode 107, as shown in FIG. 1C.

A structure of layers provided between the first electrode 102 and the second electrode 107 is not limited to the above-described structure. A structure other than the above-described structure may be used as long as the light-emitting region, in which holes and electrons are recombined, is located away from the first electrode 102 and the second electrode 107, to prevent the quenching due to proximity of the light-emitting region and the metal.

In other words, a stacked structure of the layer is not particularly limited to the abovementioned structure, and a layer formed using a substance having a high electron-transporting property, a substance having a high hole-transporting property, a substance having a high electron-injecting property, a substance having a high hole-injecting property, a bipolar substance (substance having a high electron-transporting property and a high hole-transporting property), a hole blocking material, or the like may be freely combined with the quinoxaline derivative of the present invention.

Figure 2:
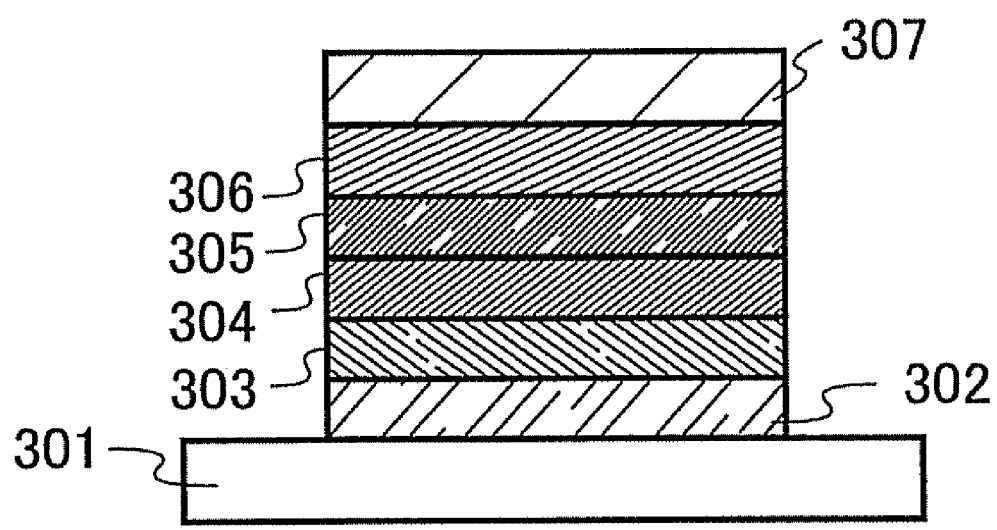
FIG. 2 is a view explaining a light-emitting element of the present invention.

A light-emitting element shown in FIG. 2 has a structure in which a first electrode 302 serving as a cathode, a first layer 303 formed using a substance having a high electron-transporting property, a second layer 304 including a light-emitting substance, a third layer 305 formed using a substance having a high hole-transporting property, a fourth layer 306 formed using a substance having a high hole-injecting property, and a second electrode 307 serving as an anode are sequentially stacked over a substrate 301.

In this embodiment mode, a light-emitting element is manufactured over a substrate made of glass, plastic, or the like. By manufacturing a plurality of the light-emitting elements described above over one substrate, a passive-matrix light-emitting device can be manufactured. Alternatively, for example, a thin film transistor (TFT) may be formed over a substrate made of glass, plastic, or the like, and the light-emitting elements may be manufactured over an electrode electrically connected to the TFT. Accordingly, an active matrix light-emitting device can be manufactured, in which driving of the light-emitting element is controlled by the TFT. The structure of the TFT is not strictly limited, and the TFT may be a staggered TFT or an inverted staggered TFT Crystallinity of a semiconductor used for the TFT is also not limited, and an amorphous semiconductor or a crystalline semiconductor may be used. In addition, a driving circuit formed over a TFT substrate may be formed using an N-type TFT and a P-type TFT, or may be formed using any one of an N-type TFT and a P-type TFT.

A quinoxaline derivative of the present invention can be used for a light-emitting layer as shown in this embodiment mode without adding any other light-emitting substance, because the quinoxaline derivative emits visible light.

In addition, since the quinoxaline derivative of the present invention exhibits a broad emission spectrum with a large half bandwidth a light-emitting element that emits light across the entire visible light region can be obtained. Therefore, a light-emitting element that exhibits white light emission with an excellent color rendering property can be obtained.

Embodiment Mode 3

In this embodiment mode, a light-emitting element with a different structure from the structure shown in Embodiment Mode 2 is described.

The third layer 105 shown in Embodiment Mode 2 is formed to have a structure in which a quinoxaline derivative of the present invention is dispersed into another substance, whereby light emission can be obtained from the quinoxaline derivative of the present invention.

Here, as the substance in which the quinoxaline derivative of the present invention is dispersed, various materials can be used other than the substance having a high hole-transporting property or the substance having a high electron-transporting property described in Embodiment Mode 2, such as the following: 4,4'-di(N-carbazolyl)biphenyl (abbreviation: CBP); 2,2',2"-(1,3,5-benzenetriyl)tris(1-phenyl-1H-benzimidazole) (abbreviation: TPBI); 9,10-di(2-naphthyl)anthracene (abbreviation: DNA); or 2-tert-butyl-9,10-di(2-naphthyl)anthracene (abbreviation: t-BuDNA).

Since the quinoxaline derivative of the present invention emits visible light, it can be favorably used as a light-emitting material for a light-emitting element.

In addition, since the quinoxaline derivative of the present invention exhibits a broad emission spectrum with a large half bandwidth, a light-emitting element that emits light across the entire visible light region can be obtained. Therefore, a light-emitting element that exhibits white light emission with an excellent color rendering property can be obtained.

Note that except for the third layer 105, the structure described in Embodiment Mode 2 can be appropriately used.

Embodiment Mode 4

In this embodiment mode, a light-emitting element with a different structure from the structures described in Embodiment Mode 2 and 3 is described.

The third layer 105 shown in Embodiment Mode 2 is formed to have a structure in which a light-emitting substance is dispersed into the quinoxaline derivative of the present invention, whereby light emission from the light-emitting substance can be obtained.

In a case where the quinoxaline derivative of the present invention is used as a material for dispersing another light-emitting substance, a light emission color derived from the light-emitting substance can be obtained. Further, a mixed light emission color resulted from the quinoxaline derivative of the present invention and the light-emitting substance dispersed in the quinoxaline derivative can also be obtained.

Here, as the light-emitting substance that is dispersed in the quinoxaline derivative of the present invention, various materials can be used. Specifically, a fluorescence emitting substance that emits fluorescent light such as 4-(dicyanomethylene)-2-methyl-6-(p-dimethylaminostyryl)-4H-pyran (abbreviation: DCM1); 4-(dicyanomethylene)-2-methyl-6-(julolidine-4-yl-vinyl)-4H-pyran (abbreviation: DCM2); N,N'-dimethylquinacridone (abbreviation: DMQd); 9,10-diphenylanthracene (abbreviation: DPA); 5,12-diphenyltetracene (abbreviation: DPT); coumarin 6; perylene; or rubrene can be used. Alternatively, a phosphorescence emitting substance that emits phosphorescent light such as bis(2-phenylbenzothiazolato-N,$C^{2'}$)iridium(III) acetylacetonate (abbreviation: Ir(bt)$_2$(acac)); tris(2-phenylquinolinato-N,$C^{2'}$) iridium(III) (abbreviation: Ir(pq)$_3$); bis(2-phenylquinolinato-N,$C^{2'}$)iridium(III)(acetylacetonate) (abbreviation: Ir(pq)$_2$ (acac)); bis[2-(2'-benzo[4,5-α]thienyl)pyridinato-N,$C^{3'}$] iridium(III)acetylacetonate (abbreviation: Ir(btp)$_2$(acac)); bis(1-phenylisoquinolinato-N,$C^{2'}$)iridium(III)acetylacetonate (abbreviation: Ir(piq)$_2$(acac)); (acetylacetonato)bis[2,3-bis(4-fluorophenyl)quinoxalinato]iridium(III) (abbreviation: Ir(Fdpq)$_2$(acac)); or 2,3,7,8,12,13,17,18-octaethyl-21H, 23H-porphyrinplatinum(II) (abbreviation: PtOEP) can be used.

Note that as the light-emitting substance that is dispersed in the quinoxaline derivative of the present invention, when a phosphorescence emitting substance is used, it is preferable that the peak of an emission spectrum of the phosphorescence emitting substance is more than or equal to 560 nm and less than or equal to 700 nm. Further, when a fluorescence emitting substance is used, it is preferable that the peak of an emission spectrum is more than or equal to 540 nm and less than or equal to 700 nm.

Note that except for the third layer 105, the structure described in Embodiment Mode 2 can be appropriately used.

Embodiment Mode 5

In this embodiment mode, a light-emitting element in which a plurality of light-emitting units according to the present invention are stacked (hereinafter, referred to as a stacked type element) will be described with reference to FIG. 3. This light-emitting element is a light-emitting element that has a plurality of light-emitting units between a first electrode and a second electrode.

Figure 3:
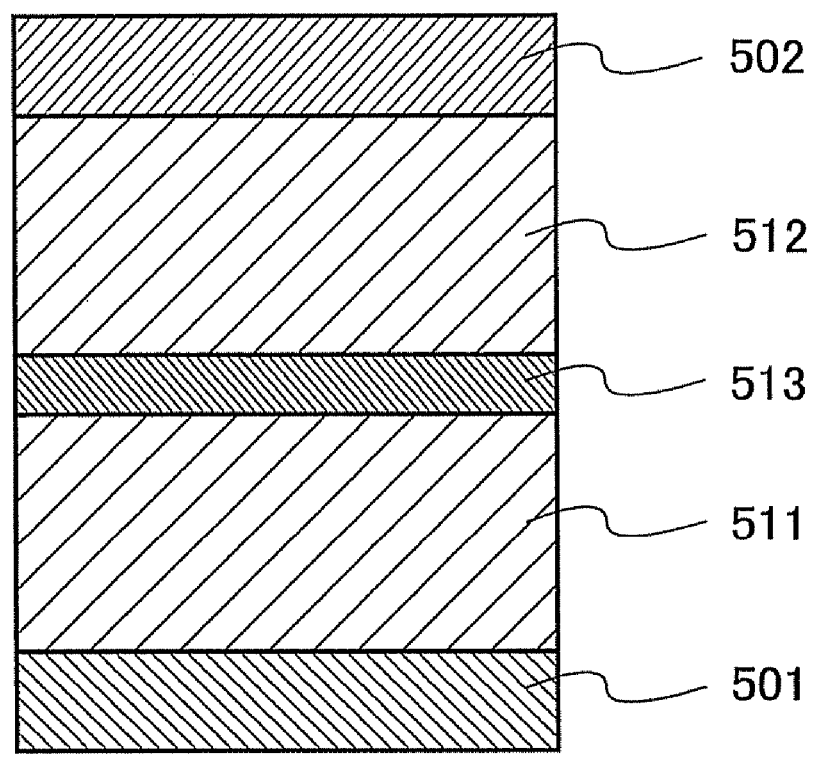
FIG. 3 is a view explaining a light-emitting element of the present invention.

In FIG. 3, a first light-emitting unit 511 and a second light-emitting unit 512 are stacked between a first electrode 501 and a second electrode 502. An electrode similar to that described in Embodiment Mode 2 can be applied to the first electrode 501 and the second electrode 502. The first light-emitting unit 511 and the second light-emitting unit 512 may have the same structure or different structures, and a structure similar to those described in Embodiment Modes 2 to 4 can be applied.

A charge generation layer 513 includes a composite material of an organic compound and a metal oxide. The composite material of an organic compound and a metal oxide is described in Embodiment Mode 2, and includes an organic compound and a metal oxide such as $V_2O_5$, $MoO_3$, or $WO_3$. As the organic compound, various compounds such as an aromatic amine compound, a carbazole derivative, an aromatic hydrocarbon, and a high molecular compound (such as oligomer, dendrimer, or polymer) can be used. An organic compound having a hole mobility of greater than or equal to $1 \times 10^{-6}$ cm$^2$/Vs is preferably applied as the organic compound having a hole-transporting property. However, other substances than these compounds may also be used as long as the hole-transporting properties thereof are higher than the electron-transporting properties thereof. The composite material of an organic compound and metal oxide is superior in a carrier injecting property and a carrier transporting property, and accordingly, low-voltage driving and low-current driving can be realized.

It is to be noted that the charge generation layer 513 may be formed with a combination of a composite material of an organic compound and metal oxide and other materials. For example, the charge generation layer 513 may be formed with a combination of a layer including the composite material of an organic compound and metal oxide and a layer including one compound selected from electron donating substances and a compound having a high electron-transporting property. Further, the charge generation layer 513 may be formed with a combination of a layer including the composite material of an organic compound and metal oxide and a transparent conductive film.

In any case, the charge generation layer 513 interposed between the first light-emitting unit 511 and the second light-emitting unit 512 is acceptable as long as electrons are injected to one light-emitting unit and holes are injected to the other light-emitting unit when a voltage is applied between the first electrode 501 and the second electrode 502.

In this embodiment mode, the light-emitting element having two light-emitting units is described; however, the present invention can be applied to a light-emitting element in which three or more light-emitting units are stacked. By arranging a plurality of light-emitting units between a pair of electrodes in such a manner that the plurality of light-emitting units are partitioned with a charge generation layer as the light-emitting element of this embodiment mode, an element having a long lifetime in a high luminance region can be realized with keeping a low current density. In a case of applying the light-emitting element to a lightning system, voltage drop due to resistance of an electrode material can be decreased; therefore, uniform light emission in a large area is possible. Further, low voltage driving is possible, and a light-emitting device with low power consumption can be realized.

Note that this embodiment mode can be appropriately combined with another embodiment mode.

Embodiment Mode 6

In this a light-emitting device that is manufactured using a quinoxaline derivative of the present invention is described with reference to FIGS. 4A and 4B.

Figure 4A:
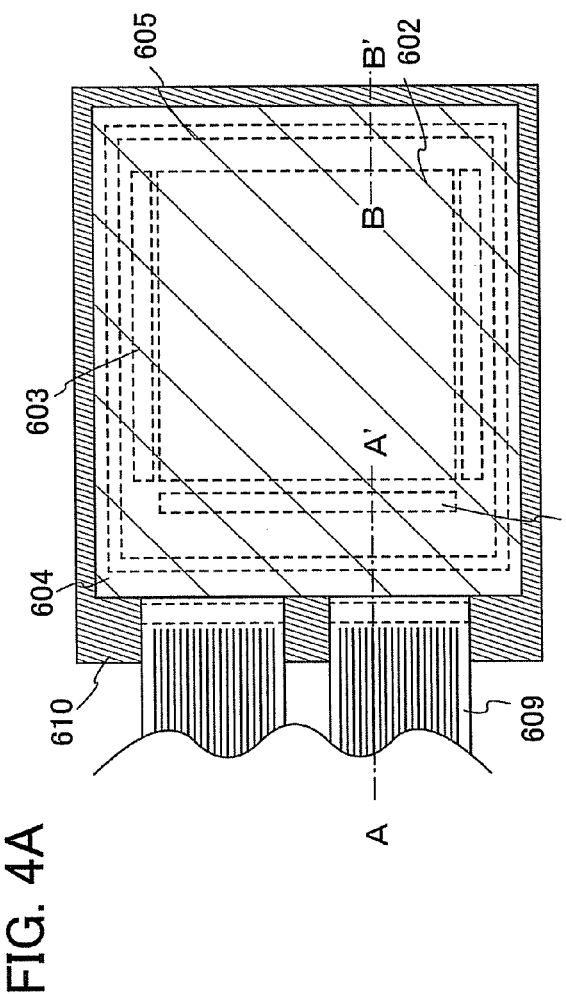
FIGS. 4A and 4B are views explaining a light-emitting device of the present invention.
Figure 4B:
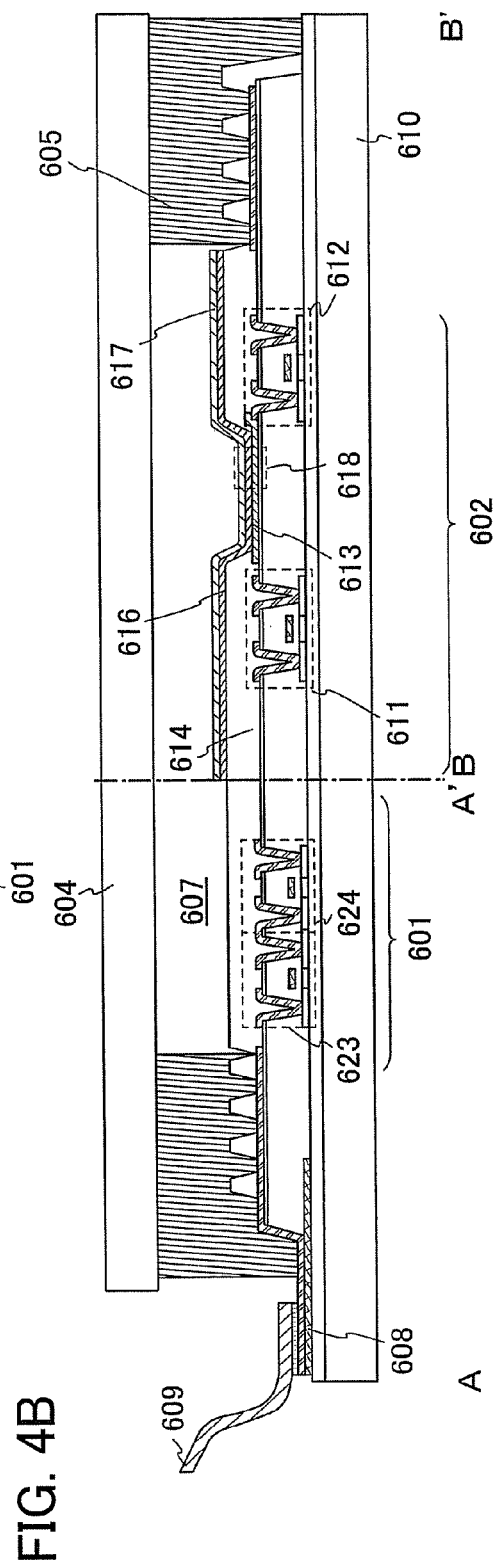

FIG. 4A is a top view showing a light-emitting device, and FIG. 4B is a cross-sectional view of FIG. 4A taken along lines A-A' and B-B'. In this light-emitting device, as portions that control light emission of a light-emitting element, a driver circuit portion 601 (source driver circuit), a pixel portion 602, and a driver circuit portion 603 (gate driver circuit) are included and indicated by dotted lines. Also, a sealing substrate and a sealing material are denoted by reference numerals 604 and 605, respectively, and a portion surrounded by the sealing material 605 corresponds to a space 607.

A leading wiring 608 is a wiring for transmitting a signal to be inputted to the source driver circuit 601 and the gate driver circuit 603, and this wiring 608 receives a video signal, a clock signal, a start signal, a reset signal, and the like from an FPC (flexible printed circuit) 609 that is an external input terminal. It is to be noted that only the FPC is shown here; however, the FPC may be provided with a printed wiring board (PWB). The light-emitting device in the present specification includes not only a light-emitting device itself but also a light-emitting device attached with an FPC or a PWB.

Subsequently, a cross-sectional structure will be described with reference to FIG. 4B. The driver circuit portion and the pixel portion are formed over an element substrate 610. Here, the source driver circuit 601, which is the driver circuit portion, and one pixel in the pixel portion 602 are shown.

A CMOS circuit, which is a combination of an n-channel TFT 623 and a p-channel TFT 624, is formed as the source driver circuit 601. A TFT that forms a driver circuit may be formed using various CMOS circuits, PMOS circuits, or NMOS circuits. Although a driver-integration type device, in which a driver circuit is formed over a substrate, is described in this embodiment, a driver circuit is not necessarily formed over a substrate and can be formed outside a substrate. In addition, crystallinity of a semiconductor used for the TFT is not particularly limited, and an amorphous semiconductor or a crystalline semiconductor may be used.

The pixel portion 602 has a plurality of pixels, each of which includes a switching TFT 611, a current control TFT 612, and a first electrode 613 that is electrically connected to a drain of the current control TFT 612. It is to be noted that an insulator 614 is formed so as to cover an end portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in a case of using a positive photosensitive acrylic as a material for the insulator 614, the insulator 614 is preferably formed so as to have a curved surface with a curvature radius (0.2 μm to 3 μm) only at the upper end portion thereof. Either a negative type which becomes insoluble in an etchant by irradiation with light or a positive type which becomes soluble in an etchant by irradiation with light can be used for the insulator 614.

An EL layer 616 and a second electrode 617 are formed over the first electrode 613. Here, a material having a high work function is preferably used as a material for the first electrode 613 serving as an anode. For example, the first electrode 613 can be formed by using stacked layers of a titanium nitride film and a film including aluminum as its main component; a three-layer structure of a titanium nitride film, a film including aluminum as its main component, and a titanium nitride film; or the like as well as a single-layer film such as an ITO film, an indium tin oxide film containing silicon, an indium oxide film containing 2 to 20 wt % of zinc oxide, a titanium nitride film, a chromium film, a tungsten film, a Zn film, or a Pt film. When the first electrode 613 has a stacked structure, the electrode 613 shows low resistance enough to serve as a wiring, giving favorable ohmic contact.

In addition, the EL layer 616 is formed by various methods such as an evaporation method using an evaporation mask, an ink-jet method, and a spin coating method. The EL layer 616 includes the quinoxaline derivative of the present invention described in Embodiment Mode 1. Further, another material that forms the EL layer 616 may be a low molecular compound, oligomer, dendrimer, or a high molecular compound.

As a material used for the second electrode 617, which is formed over the EL layer 616 and serves as a cathode, a material having a low work function (Al, Mg, Li, Ca, or an alloy or a compound thereof such as MgAg, MgIn, AlLi, LiF, or $CaF_2$) is preferably used. In a case where light generated in the EL layer 616 is transmitted through the second electrode 617, stacked layers of a metal thin film and a transparent conductive film (ITO, indium oxide containing 2 to 20 wt % of zinc oxide, indium oxide-tin oxide containing silicon or silicon oxide, zinc oxide (ZnO), or the like) are preferably used as the second electrode 617.

By attachment of the sealing substrate 604 to the element substrate 610 with the sealing material 605, a light-emitting element 618 is provided in the space 607 surrounded by the element substrate 610, the sealing substrate 604, and the sealing material 605. It is to be noted that the space 607 is filled with an inert gas (nitrogen, argon, or the like). There is also a case where the space 607 is filled with the sealing material 605.

It is to be noted that an epoxy-based resin is preferably used as the sealing material 605. It is desired that the material allows as little moisture and oxygen as possible to penetrate. As the sealing substrate 604, a plastic substrate formed using FRP (Fiberglass-Reinforced Plastics), PVF (polyvinyl fluoride), polyester, acrylic resin, or the like can be used as well as a glass substrate or a quartz substrate.

Accordingly, a light-emitting device that is manufactured using the quinoxaline derivative of the present invention can be obtained.

Since the light-emitting device of the present invention uses the quinoxaline derivative described in Embodiment Mode 1, a light-emitting device with favorable characteristics can be obtained.

Since the quinoxaline derivative of the present invention emits visible light, it can be favorably used as a light-emitting material for a light-emitting element.

In addition, since the quinoxaline derivative of the present invention exhibits a broad emission spectrum with a large half bandwidth a light-emitting element that emits light across the entire visible light region can be obtained. Therefore, a light-emitting element that exhibits white light emission with an excellent color rendering property can be obtained.

In addition, the quinoxaline derivative of the present invention can be favorably used for a light-emitting element as a substance that disperses a light-emitting material.

Figure 5A:
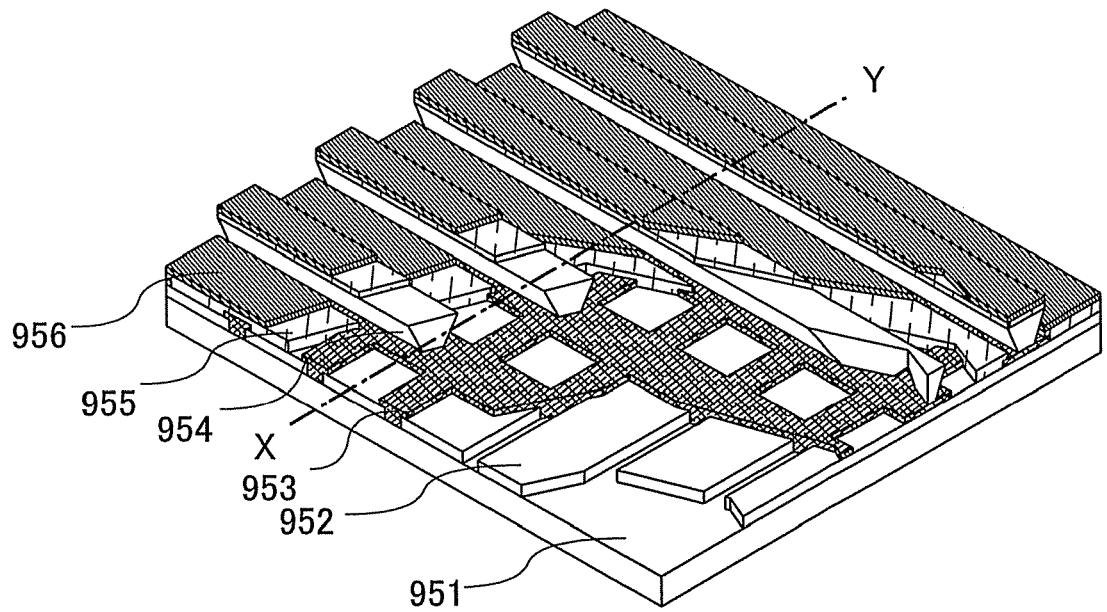
FIGS. 5A and 5B are views explaining a light-emitting device of the present invention.
Figure 5B:
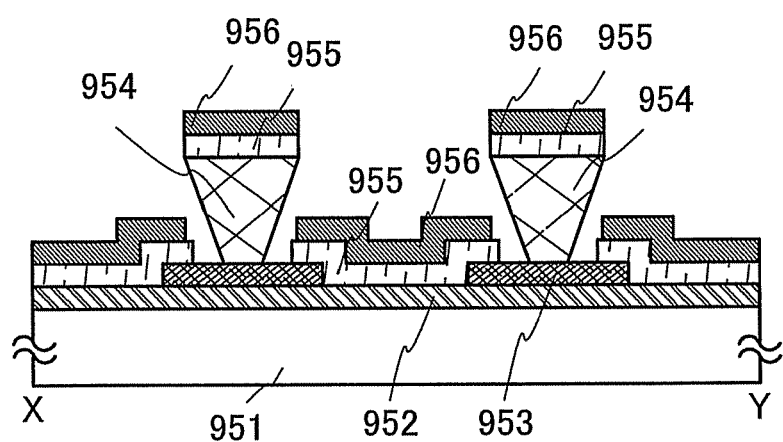

As described above, an active-matrix light-emitting device that controls driving a light-emitting element with a transistor is described in this embodiment mode; however, a passive-matrix light-emitting device may be used. A perspective view of a passive-matrix light-emitting device manufactured to which the present invention is applied is shown in FIG. 5A. In FIGS. 5A and 5B, an EL layer 955 is provided between an electrode 952 and an electrode 956 over a substrate 951. An end of the electrode 952 is covered with an insulating layer 953. Then, a partition layer 954 is provided over the insulating layer 953. A sidewall of the partition layer 954 slopes so that a distance between one sidewall and the other sidewall becomes narrow toward a substrate surface. In other words, a cross section of the partition layer 954 in the direction of a short side is trapezoidal, and a base (a side expanding in a similar direction as a plane direction of the insulating layer 953 and in contact with the insulating layer 953) is shorter than an upper side (a side expanding in a similar direction as the plane direction of the insulating layer 953 and not in contact with the insulating layer 953). The partition layer 954 provided in this manner allows prevention of defects of a light-emitting element due to static electricity. A light-emitting device with an excellent color rendering property can also be obtained in the case of the passive-matrix light-emitting device by including the light-emitting element of the present invention.

Embodiment Mode 7

By using the quinoxaline derivative of the present invention for a light-emitting material, white light emission with a high color rendering property can be obtained. Therefore, the quinoxaline derivative of the present invention can be favorably used for a lighting system. A mode in which a light-emitting element of the present invention is used for a lighting system is described with reference to FIGS. 6 to 8.

Figure 6:
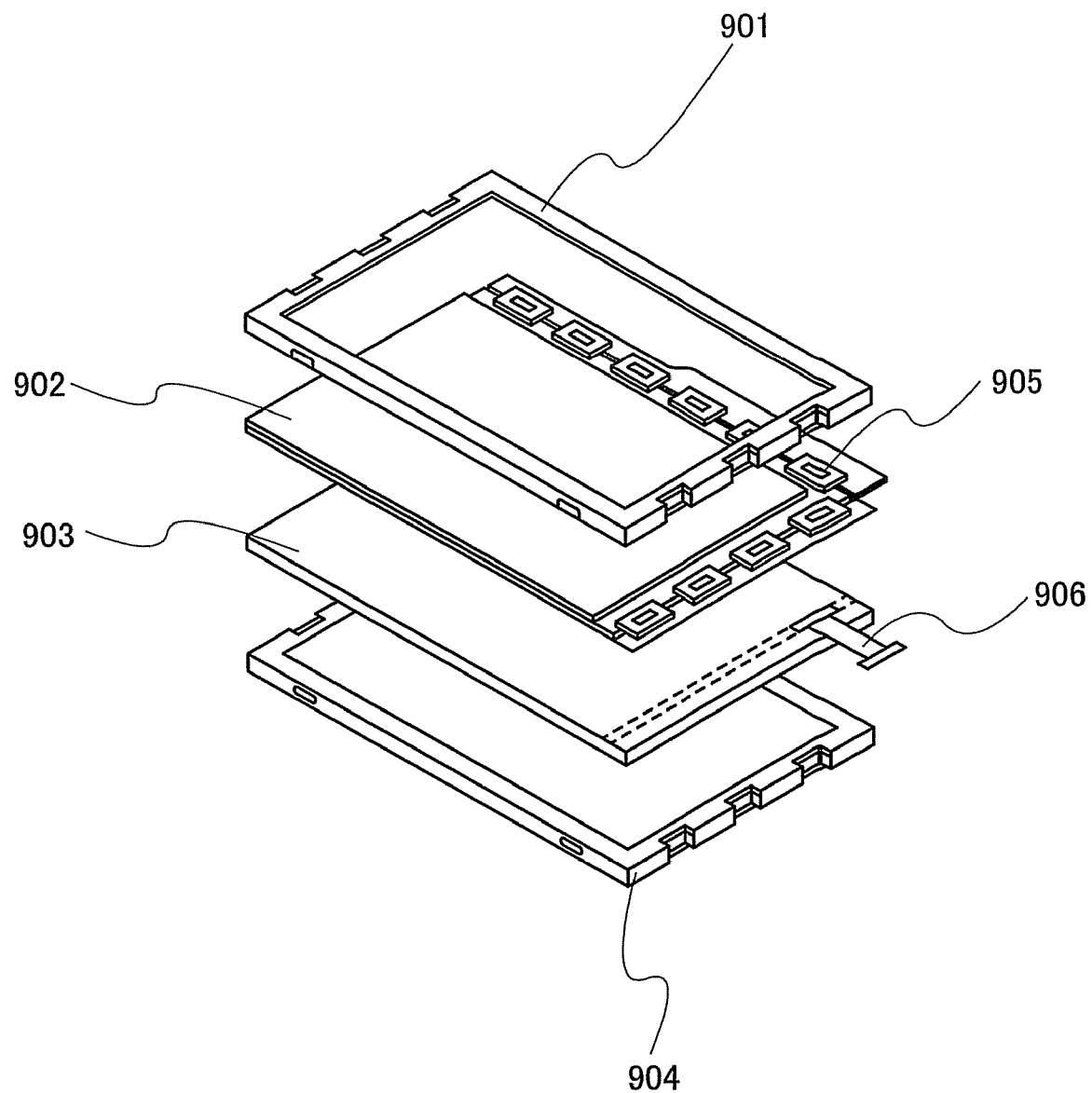
FIG. 6 is a view explaining an electronic appliance using a light-emitting device of the present invention.

FIG. 6 shows a liquid crystal display device as an example of an electronic appliance using the light-emitting device of the present invention as a backlight. The liquid crystal display device shown in FIG. 6 includes a housing 901, a liquid crystal layer 902, a backlight 903, and a housing 904, and the liquid crystal layer 902 is connected to a driver IC 905. The light-emitting device of the present invention is used for the backlight 903, and current is supplied through a terminal 906.

By using the quinoxaline derivative of the present invention for a light-emitting material, a light-emitting device capable of white light emission with a high color rendering property can be obtained. Accordingly, by using the light-emitting device of the present invention as the backlight of the liquid crystal display device, a backlight with an excellent color rendering property can be obtained. Therefore, a liquid crystal display device with excellent color reproducibility can be obtained. Further, since the light-emitting device of the present invention is a lighting system with plane light emission, and can have a large area, the backlight can have a large area, and a liquid crystal display device having a large area can be obtained.

Figure 7:
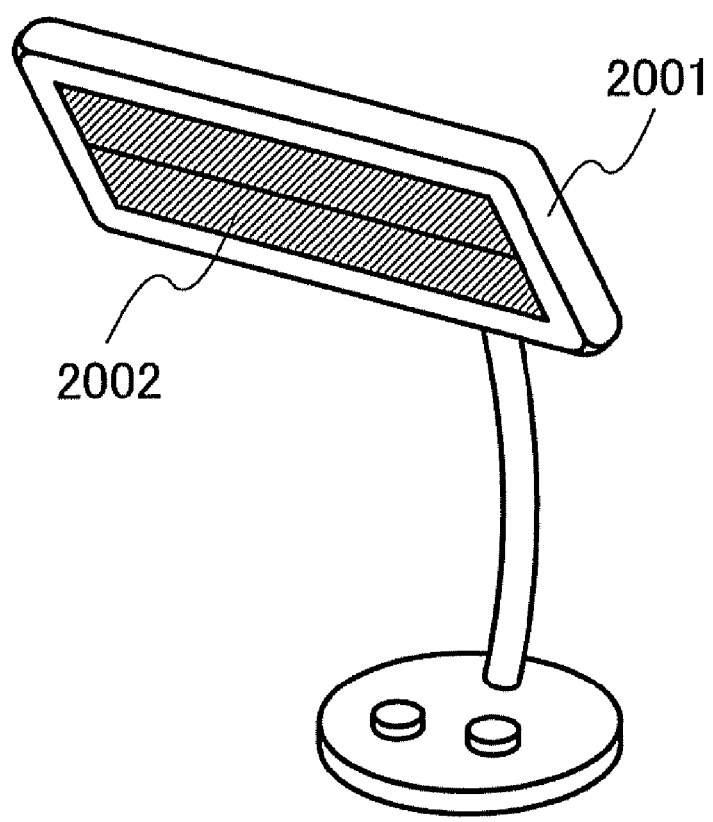
FIG. 7 is a view explaining a lighting system using a light-emitting device of the present invention.

FIG. 7 shows an example in which a light-emitting device to which the present invention is applied is used for a table lamp, which is a lighting system. A table lamp shown in FIG. 7 includes a housing 2001 and a light source 2002, and the light-emitting device of the present invention is used as the light source 2002. The light-emitting device of the present invention is capable of white light emission with an excellent color rendering property; therefore, a lighting system that gives light emission close to that of natural light can be obtained. In addition, by lighting with the lighting system of the present invention, color of an object can be recognized in a similar manner to recognition under natural light.

Figure 8:
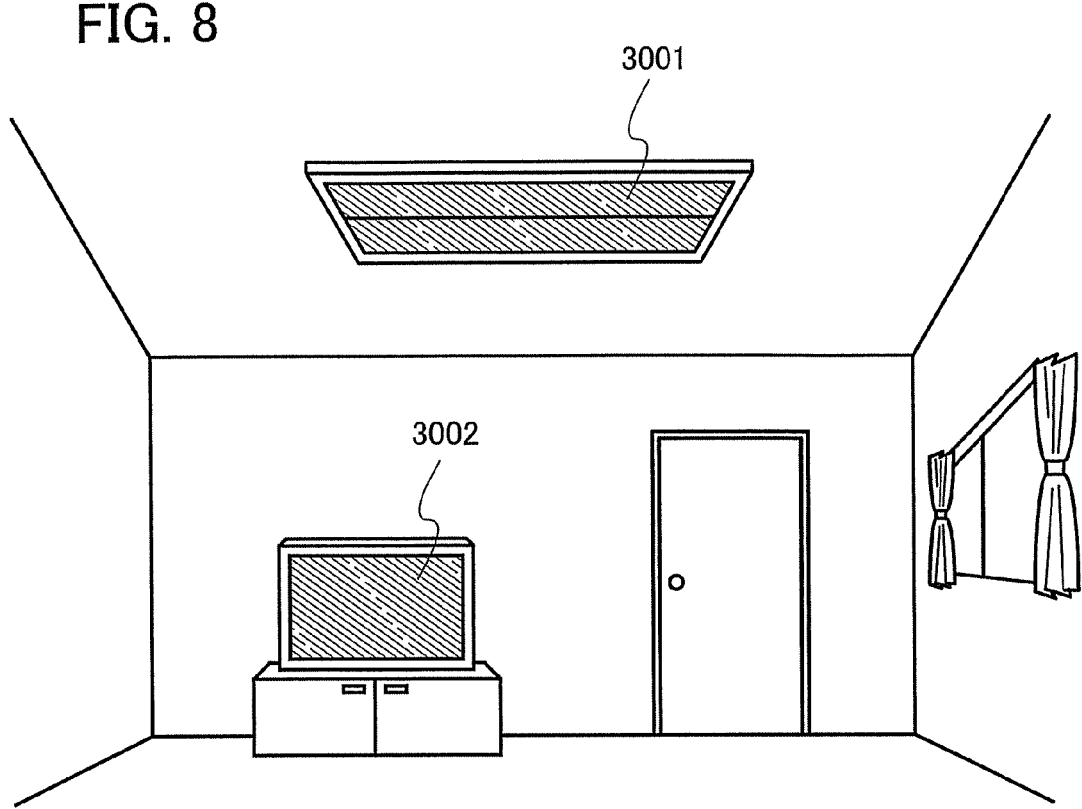
FIG. 8 is a view explaining a lighting system using a light-emitting device of the present invention.

FIG. 8 shows an example in which a light-emitting device to which the present invention is applied is used for an indoor lighting system 3001. The light-emitting device of the present invention is capable of white light emission with an excellent color rendering property; therefore, a lighting system that gives light emission close to that of natural light can be obtained. In addition, by lighting with the lighting system of the present invention, color of an object can be recognized in a similar manner to recognition under natural light. Further, since the light-emitting device of the present invention can also have a large area, the light-emitting device of the present invention can be used as a lighting system having a large emission area. Furthermore, the light-emitting device of the present invention has a thin shape; therefore, the light-emitting device of the present invention can be used as a lighting system having a thin shape. A television device 3002 using the light-emitting device of the present invention as described in FIG. 6 is placed in a room in which the light-emitting device to which the present invention is applied is used as the indoor lighting device 3001, and public broadcasting and movies can be watched. In such a case, a beautiful image with excellent color reproducibility can be watched in a room lit with light that is close to natural light.

Embodiment 1

In this embodiment, a synthesis example of 2,3-bis[4-(10-anthryl)phenyl]quinoxaline (abbreviation: APQ) that is the quinoxaline derivative of the present invention represented by Structural Formula (101) below, is specifically described.

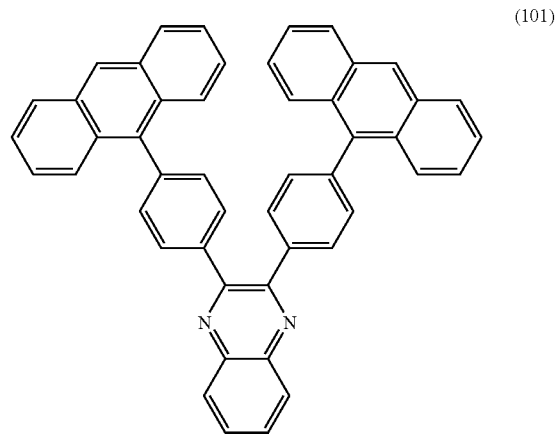

[Step 1] Synthesis of 2,3-bis(4-bromophenyl)quinoxaline

A synthesis method of 2,3-bis(4-bromophenyl)quinoxaline is described. A synthesis scheme of 2,3-bis(4-bromophenyl)quinoxaline is shown in (B-1).

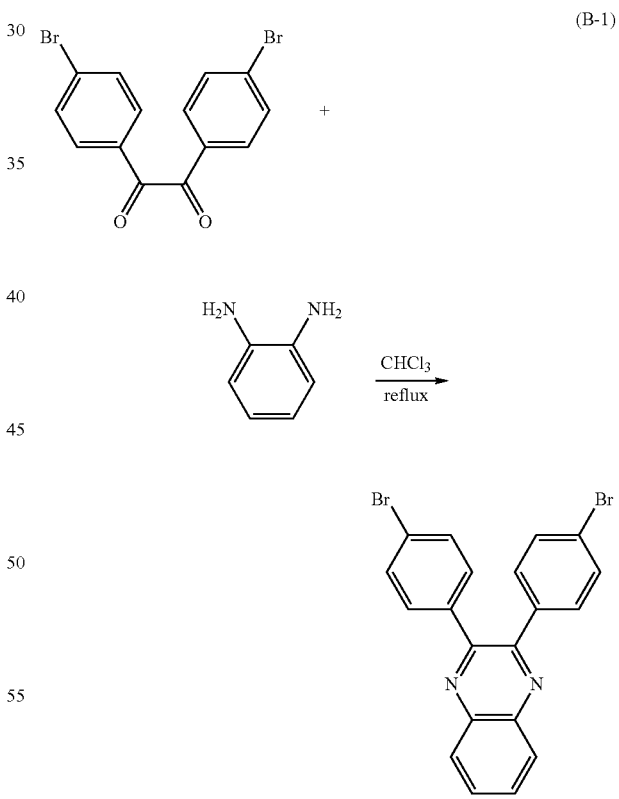

Under a nitrogen gas stream, 30.2 g (82.0 mmol) of 4,4'-dibromobenzyl, 9.31 g (86.1 mmol) of 1,2-phenylenediamine, and 300 mL of chloroform were put into a 500 mL three-neck flask. This solution was refluxed at 80° C. for 5 hours. After a reaction was completed, the reaction solution was cooled to room temperature and washed with water. A water layer was extracted with chloroform, and the extracted solution was combined with an organic layer and then dried with magnesium sulfate. After drying, the mixture was subjected to suction filtration and the filtrate was concentrated. An obtained solid was dissolved in toluene, and this solution was subjected to suction filtration through Florisil, celite, and alumina. The filtrate was concentrated, and 30 g of a white, powdery solid of 2,3-bis(4-bromophenyl)quinoxaline, which was a target matter, was obtained with the yield of 99%.

[Step 2] Synthesis of 4,4'-(quinoxaline-2,3-diyl)diphenyl boronic acid

A synthesis method of 4,4'-(quinoxaline-2,3-diyl)diphenyl boronic acid is described. A synthesis scheme of 4,4'-(quinoxaline-2,3-diyl)diphenyl boronic acid is shown in (3-2).

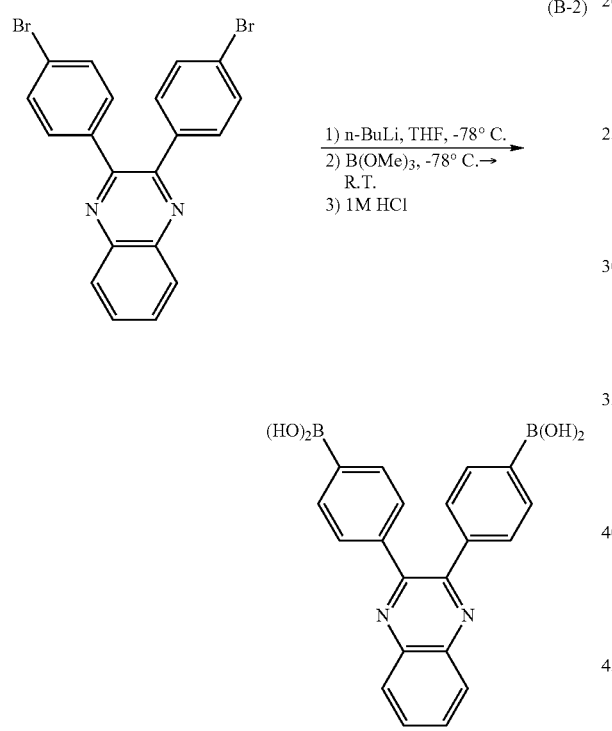

20.0 g (54.1 mol) of 2,3-bis(4-bromophenyl)quinoxaline was put into a 500 mL three-neck flask, and nitrogen substitution in the flask was carried out. 150 mL of tetrahydrofuran (abbreviation: THF) was added to this mixture. After this solution was brought to −78° C., 75.8 mL (119 mmol) of n-butyllithium (1.57 mol/L hexane solution) was dropped and the solution was stirred at the same temperature for 2 hours. Thereafter, 22.5 g (216 mmol) of trimethyl borate was added, and the solution was stirred for 24 hours as it was brought back to room temperature. After completion of a reaction, 200 mL of 1.0 mol/L hydrochloric acid was added to the reaction solution and stirred at room temperature for 1 hour. A precipitate in the reaction mixture was collected by suction filtration, and an obtained residue was recrystallized with a mixed solvent of chloroform and hexane, thereby obtaining 14.6 g of a white, powdery solid of 4,4'-(quinoxaline-2,3-diyl)diphenyl boronic acid, which was the target matter, with the yield of 73%.

[Step 3] Synthesis of APQ

A synthesis scheme of 2,3-bis[4-(10-anthryl)phenyl]quinoxaline (abbreviation: APQ) is shown in (B-3).

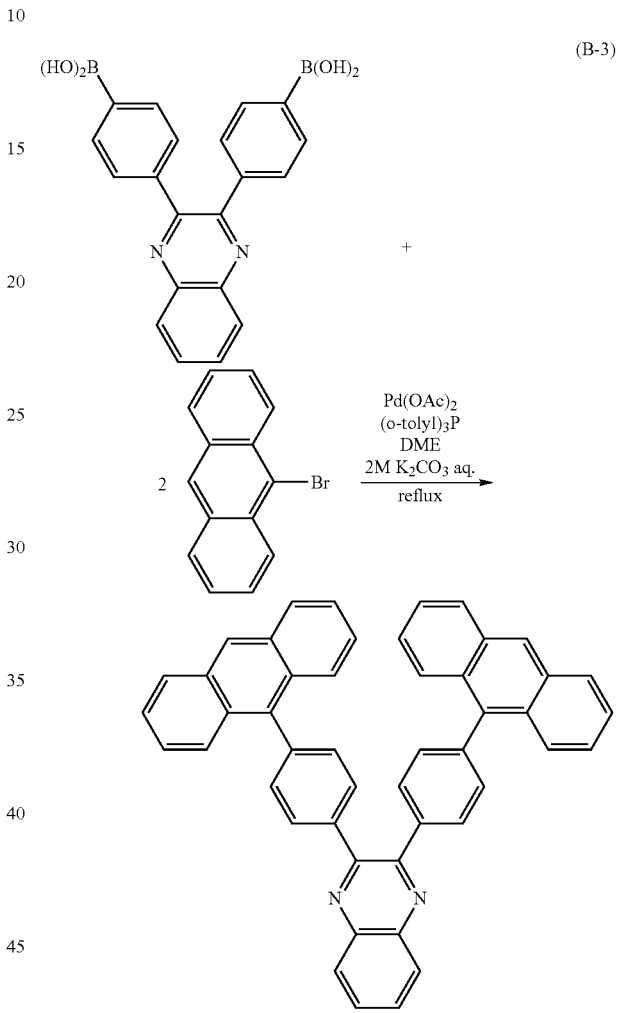

7.5 g (30 mmol) of 9-bromoanthracene, 5.0 g (14 mmol) of 4,4'-(quinoxaline-2,3-diyl)diphenyl boronic acid, 0.067 g (0.30 mmol) of palladium(II) acetate, and 0.64 g (2.1 mmol) of tri(ortho-tolyl)phosphine were put into a 200 mL three-neck flask, and nitrogen substitution in the flask was carried out. Then, 60 mL of ethylene glycol dimethyl ether (abbreviation: DME) and 45 mL (90 mmol) of a potassium carbonate aqueous solution (2.0 mol/L) were added to this mixture. This mixture was refluxed under a nitrogen gas stream at 80° C. for 7 hours. After completion of a reaction, a precipitate in the reaction mixture was collected by suction filtration. An obtained solid was dissolved in chloroform, and this solution was subjected to suction filtration through Florisil, celite, and alumina. When a solid obtained by concentrating the filtrate was recrystallized with a mixed solvent of chloroform and hexane 7.0 g of a light yellow, powdery solid, which was a target matter, was obtained with the yield of 81%. By a nuclear magnetic resonance method (NMR), it was confirmed that this compound was 2,3-bis[4-(10-anthryl)phenyl]quinoxaline (abbreviation: APQ).

Figure 10A:
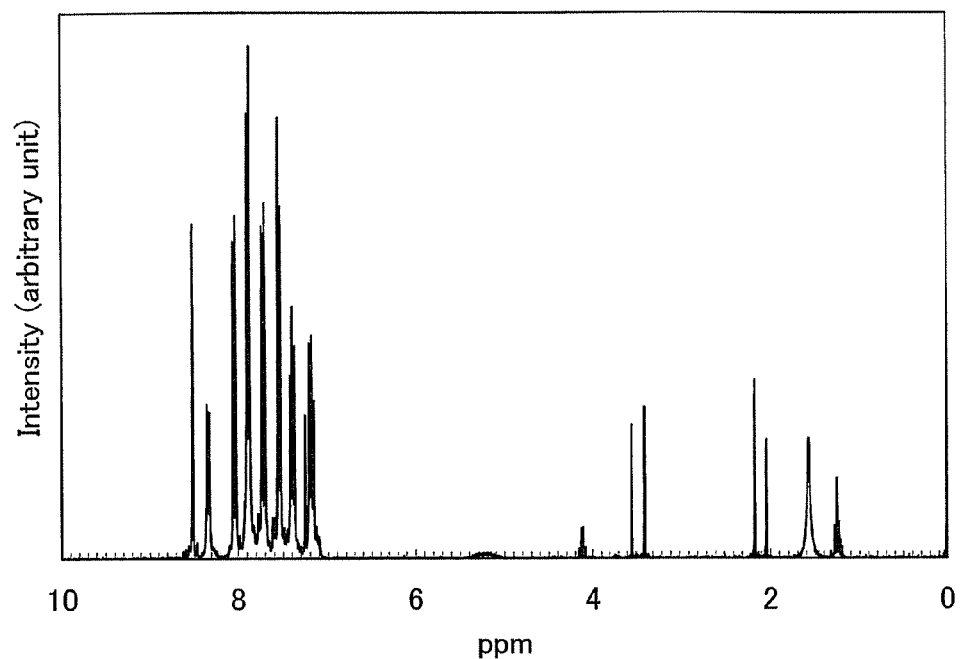
FIGS. 10A and 10B are each a graph showing an $^1$H NMR chart of 2,3-bis[4-(10-anthryl)phenyl]quinoxaline (abbreviation: APQ), which is a quinoxaline derivative of the present invention.
Figure 10B:
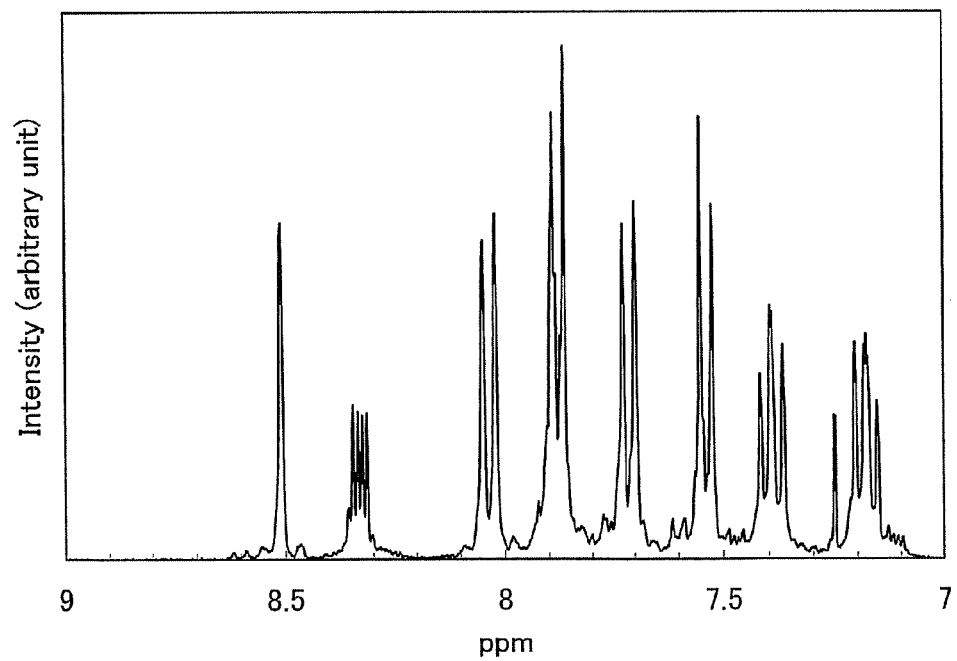

The analysis result of APQ by a proton nuclear magnetic resonance method ($^1$H NMR) was as follows: $^1$H NMR (300 MHz, CDCl$_3$): δ=7.16-7.20 (m, 4H), 7.37-7.42 (m, 4H), 7.54 (d, J=8.4 Hz, 4H), 7.71 (d, J=9.3 Hz, 4H), 7.86-7.89 (m, 6H), 8.04 (d, J=8.4 Hz, 4H), 8.31-8.35 (m, 2H), 8.51 (s, 2H). Also, a $^1$H NMR chart is shown in each of FIGS. 10A and 10B. Note that FIG. 10B is a chart showing an enlargement of FIG. 10A in the range of 7.0 ppm to 9.0 ppm.

The thermogravimetry-differential thermal analysis (TG-DTA) of APQ was performed using a thermo-gravimetric/differential thermal analyzer (TG/DTA 320, product of Seiko Instruments Inc.). The thermophysical properties were evaluated under a nitrogen atmosphere at a rate of temperature increase of 10° C./min. As a result, based on the relationship between gravity and temperature (thermogravimetric measurement), the temperature at which the gravity is 95% or less of the gravity at the starting point of the measurement, under normal pressure, was 441° C., and high heat resistance was exhibited.

Figure 11:
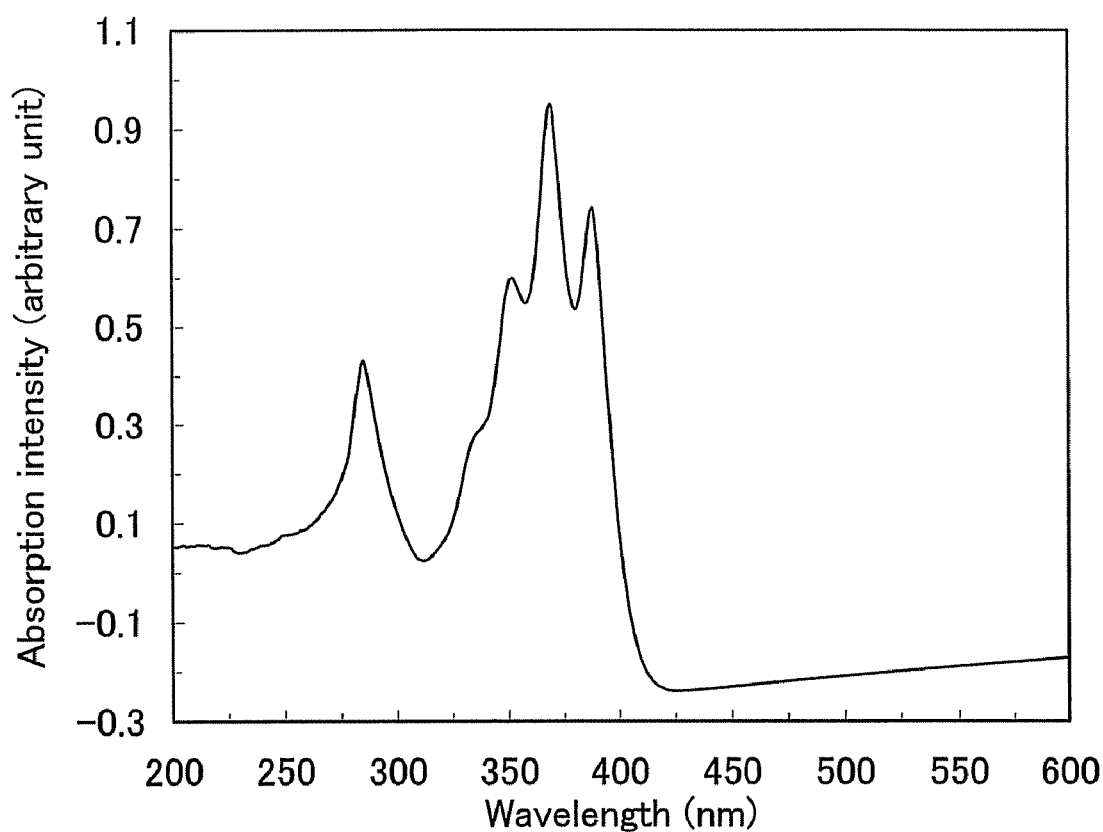
FIG. 11 is a graph showing an absorption spectrum of 2,3-bis[4-(10-anthryl)phenyl]quinoxaline (abbreviation: APQ), which is a quinoxaline derivative of the present invention, in a toluene solution.
Figure 12:
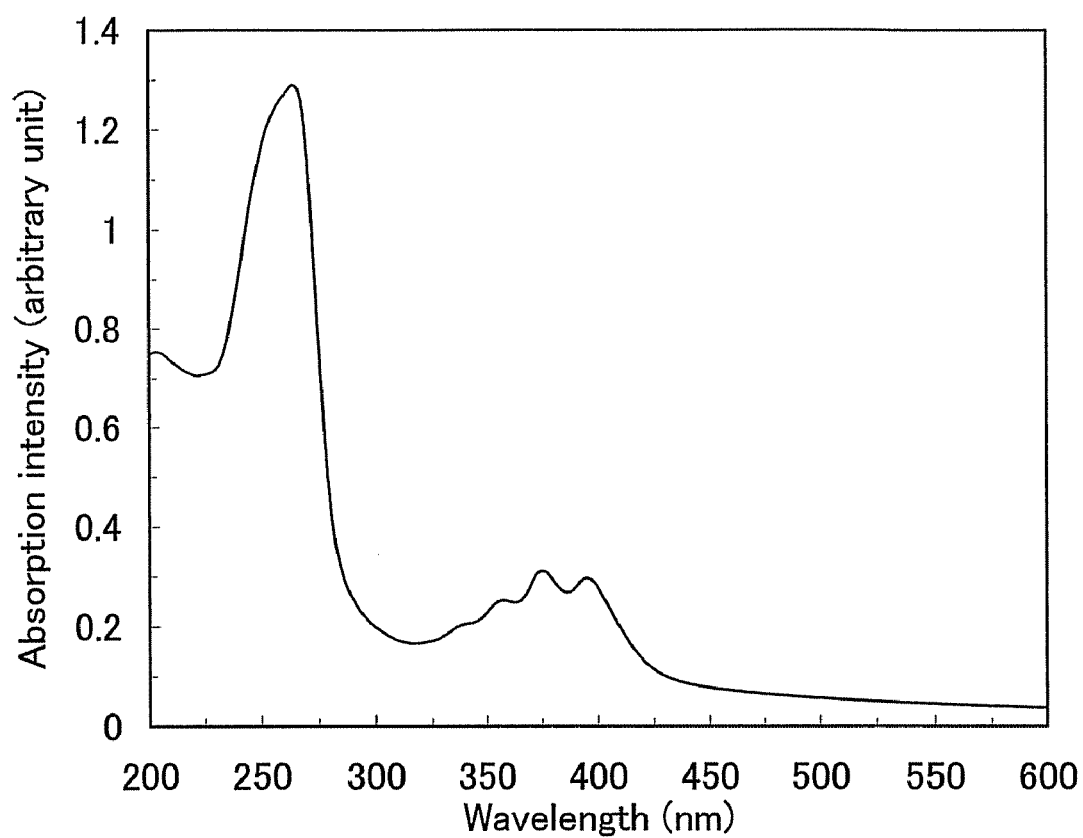
FIG. 12 is a graph showing an absorption spectrum of a thin film of 2,3-bis[4-(10-anthryl)phenyl]quinoxaline (abbreviation: APQ), which is a quinoxaline derivative of the present invention.
Figure 13:
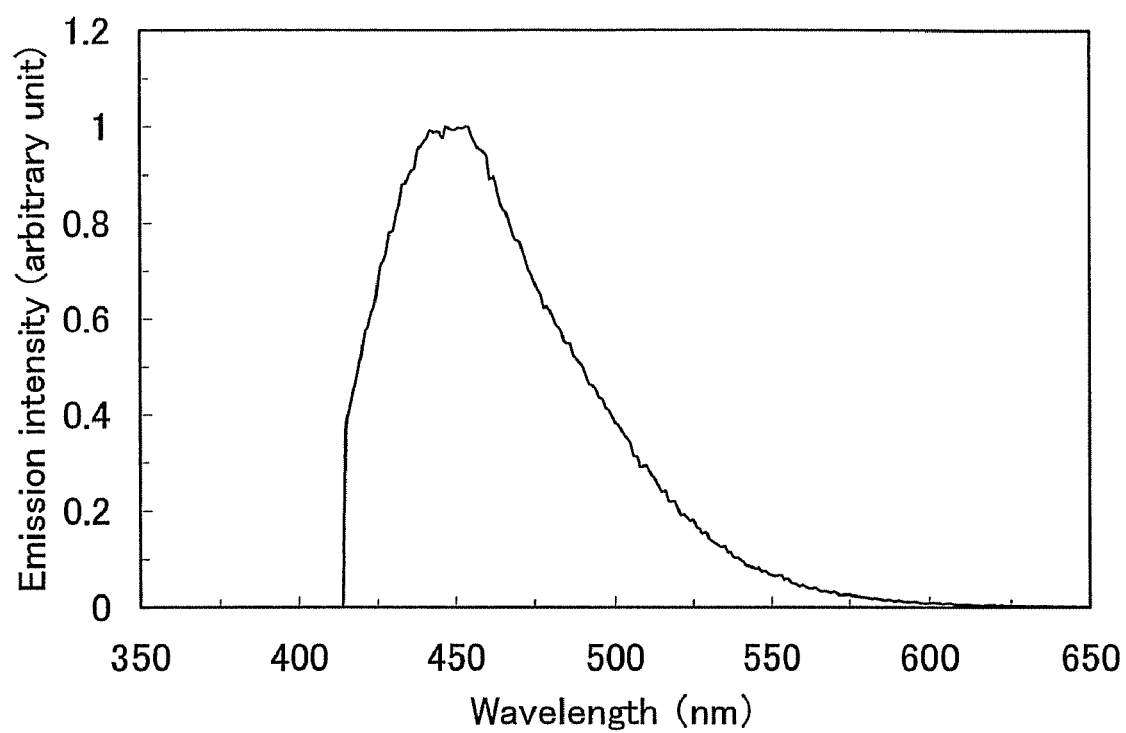
FIG. 13 is a graph showing an emission spectrum of 2,3-bis[4-(10-anthryl)phenyl]quinoxaline (abbreviation: APQ), which is a quinoxaline derivative of the present invention, in a toluene solution.
Figure 14:
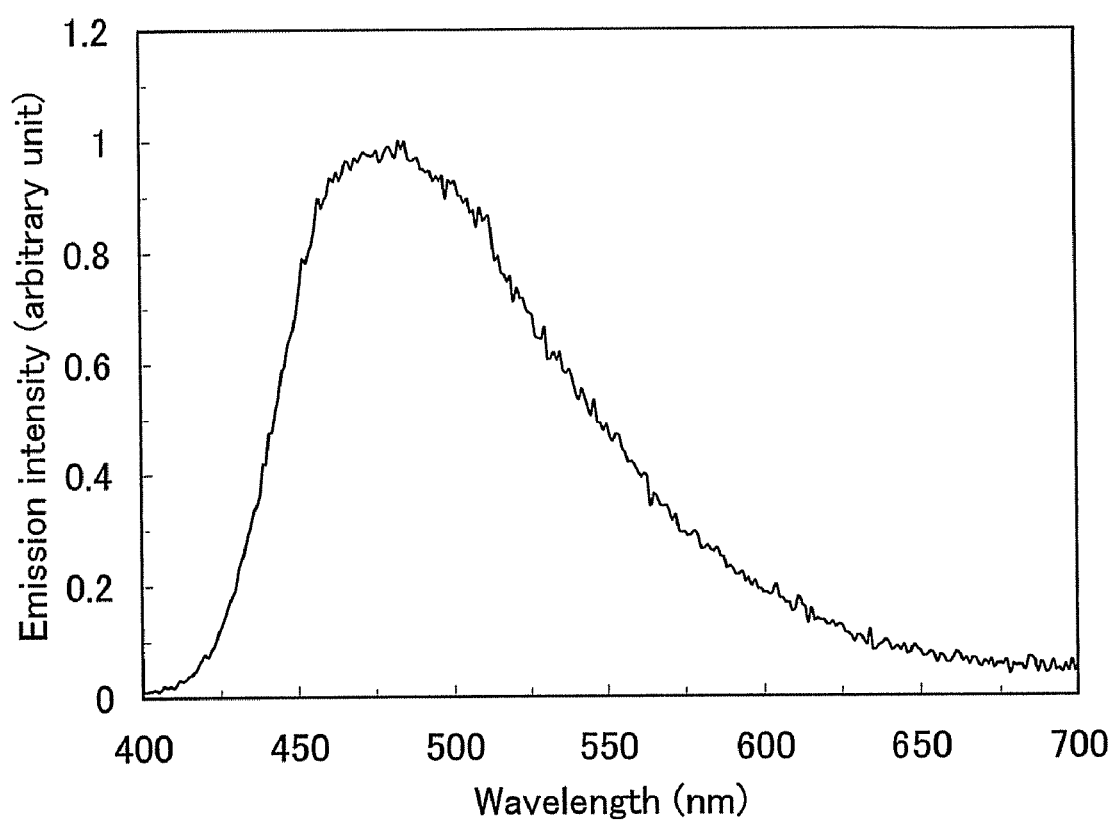
FIG. 14 is a graph showing an emission spectrum of a thin film of 2,3-bis[4-(10-anthryl)phenyl]quinoxaline (abbreviation: APQ), which is a quinoxaline derivative of the present invention.

FIG. 11 shows an absorption spectrum of a toluene solution of APQ. FIG. 12 shows an absorption spectrum of a thin film of APQ. An ultraviolet-visible spectrophotometer (V-550, manufactured by JASCO Corporation) was used for the measurement. The solution was put into a quartz cell and the thin film was evaporated on a quartz substrate to form the samples. The absorption spectra thereof from each of which the absorption spectrum of quartz was subtracted, are shown in FIGS. 11 and 12. In FIGS. 11 and 12, the horizontal axis indicates the wavelength (nm) and the vertical axis indicates the absorption intensity (arbitrary unit). In the case of the toluene solution, absorption was observed around 357 nm, 369 nm, and 380 nm, and in the case of the thin film, absorption was observed around 376 nm and 396 nm. The emission spectrum of the toluene solution of APQ (excitation wavelength: 393 nm) is shown in FIG. 13. The emission spectrum of the thin film of APQ (excitation wavelength: 396 nm) is shown in FIG. 14. In FIGS. 13 and 14, the horizontal axis indicates the wavelength (nm), and the vertical axis indicates the emission intensity (arbitrary unit). The maximum emission wavelength was 447 nm (the excitation wavelength: 393 nm) in the case of the toluene solution, and 483 nm (the excitation wavelength: 396 nm) in the case of the thin film.

In addition, the ionization potential of APQ in the thin film state was 5.76 eV, which was measured by a photoelectron spectrometer (AC-2, manufactured by Riken Keiki Co., Ltd.) in the air. As a result the HOMO level was found to be −5.76 eV. Moreover, the absorption edge was obtained from Tauc plot, with an assumption of direct transition, using data on the absorption spectrum of the thin film of APQ in FIG. 12. When the absorption edge was estimated as an optical energy gap, the energy gap was 2.96 eV The LUMO level was calculated from the obtained value of the energy gap and the HOMO level, which was −2.80 eV.

Embodiment 2

In this embodiment, a synthesis example of 2,3-bis[4-(9-phenyl-10-anthryl)phenyl]quinoxaline (abbreviation: PAPQ), which is a quinoxaline derivative of the present invention represented by Structural Formula (118) below, is specifically described.

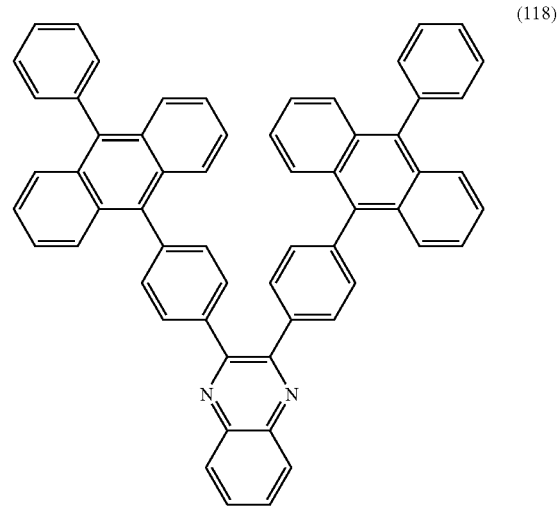

(118)

[Step 1] Synthesis of 9-phenylanthracene

A synthesis method of 9-phenylanthracene is described. A synthesis scheme of 9-phenylanthracene is shown in (C-1).

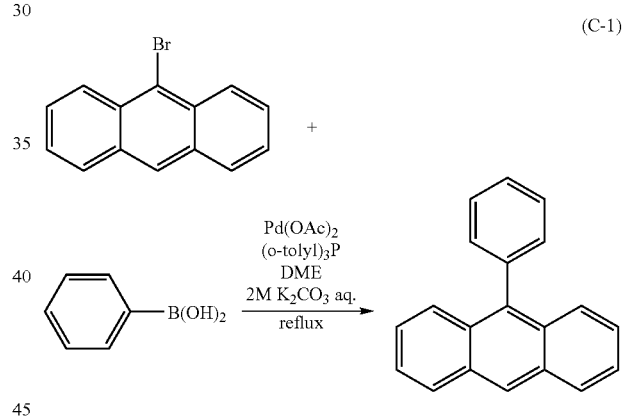

(C-1)

25.4 g (100 mmol) of 9-bromoanthracene, 12.8 g (105 mmol) of phenylboronic acid, 0.233 g (1.00 mmol) of palladium(II) acetate, and 0.913 g (3.00 mmol) of tri(ortho-tolyl)phosphine were put into a 500 mL three-neck flask, and nitrogen substitution in the flask was carried out. Then, 100 mL of ethylene glycol dimethyl ether (abbreviation: DME) and 75 ml (150 mmol) of a potassium carbonate aqueous solution (2.0 mol/L) were added to this mixture. This solution was refluxed under a nitrogen gas stream at 90° C. for 6 hours. After completion of a reaction, a precipitate in the reaction mixture was collected by suction filtration. When an obtained solid was recrystallized with a mixed solvent of chloroform and hexane, 20.8 g of a white, powdery solid of 9-phenylanthracene, which was a target matter, was obtained with the yield of 82%.

[Step 2] Synthesis of 9-bromo-10-phenylanthracene

A synthesis method of 9-bromo-10-phenylanthracene is described. A synthesis scheme of 9-bromo-10-phenylanthracene is shown in (C-2).

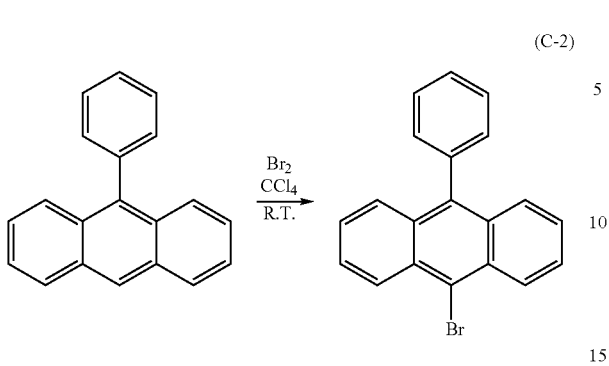

(C-2)

20.8 g (81.7 mmol) of 9-phenylanthracene and 300 mL of carbon tetrachloride were put into a 500 mL three-neck flask. Then, a solution in which 13.1 g (81.7 mmol) of bromine was dissolved in 5.00 mL of carbon tetrachloride was dropped into this mixture, and after dropping, the mixture was stirred at room temperature for 3 hours. After completion of a reaction, a sodium thiosulfate aqueous solution was added to the reaction solution, and then an organic layer was washed with water and dried with magnesium sulfate. After drying, this mixture was subjected to suction filtration, and a filtrate was concentrated. When an obtained solid was recrystallized with a mixed solvent of chloroform and hexane, 23.8 g of a light yellow, powdery solid of 9-bromo-10-phenylanthracene, which was a target matter, was obtained with the yield of 71%.

A synthesis method of 2,3-bis[4-(9-phenyl-10-anthryl)phenyl]quinoxaline (abbreviation: PAPQ) is described. A synthesis scheme of PAPQ is shown in (C-3).

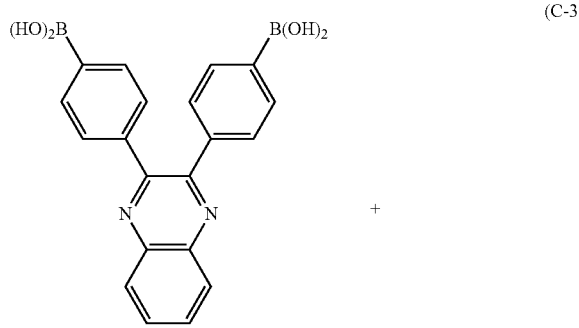

(C-3)

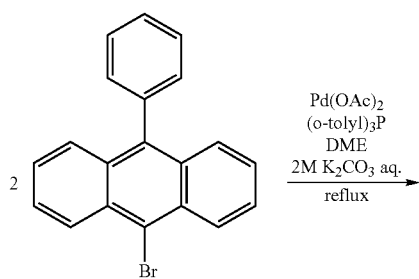

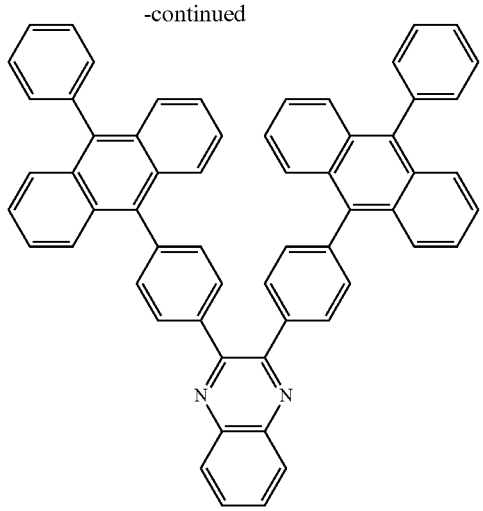

-continued 4.0 g (12 mmol) of 9-bromo-10-phenylanthracene, 2.0 g (5.4 mmol) of 4,4'-(quinoxaline-2,3-diyl)diphenyl boronic acid that was synthesized in Embodiment 1, 0.024 g (0.11 mmol) of palladium(II) acetate, and 0.23 g (0.76 mmol) of tri(ortho-tolyl)phosphine were put into a 100 mL three-neck flask, and nitrogen substitution in the flask was carried out. Then, 30 mL of ethylene glycol dimethyl ether (abbreviation: DME) and 8 mL (16 mmol) of a potassium carbonate aqueous solution (2.0 mol/L) were added to this mixture. This mixture was refluxed under a nitrogen-gas substitution stream at 80° C. for 17 hours. After completion of a reaction, a precipitate in the reaction mixture was collected by suction filtration. An obtained solid was dissolved in chloroform, and this solution was subjected to suction filtration through Florisil, celite, and alumina. When a filtrate was concentrated and an obtained solid was recrystallized with a mixed solvent of chloroform and hexane, 2.4 g of a light yellow, powdery solid that was a target matter, was obtained with the yield of 55%. By a nuclear magnetic resonance method (NMR), it was confirmed that this compound was 2,3-bis[4-(9-phenyl-10-anthryl)phenyl]quinoxaline (abbreviation: PAPQ).

When 2.3 g of the obtained 2,3-bis[4-(9-phenyl-10-anthryl)phenyl]quinoxaline (abbreviation: PAPQ) was subjected to sublimation purification by heating it to 360° C. under a condition of a pressure of 7.8 Pa and an argon flow rate of 3.0 mL/min, 1.7 g was collected, and the collection rate was 71%.

Figure 15A:
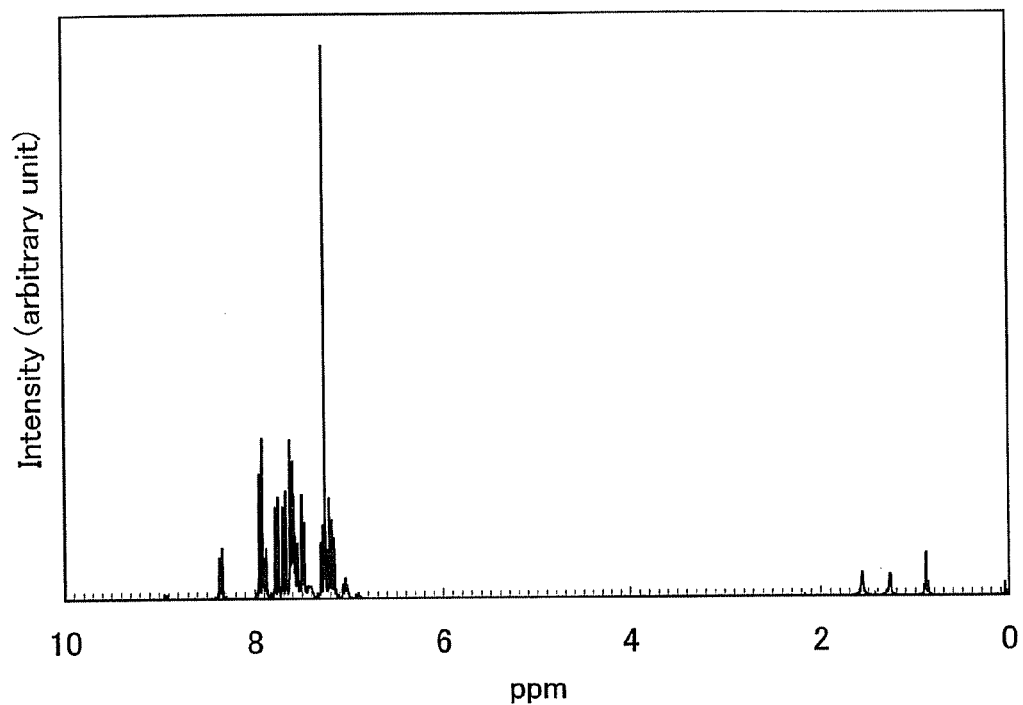
FIGS. 15A and 15B are each a graph showing a $^1$H NMR chart of 2,3-bis[4-(9-phenyl-10-anthryl)phenyl]quinoxaline (abbreviation: PAPQ), which is a quinoxaline derivative of the present invention.
Figure 15B:
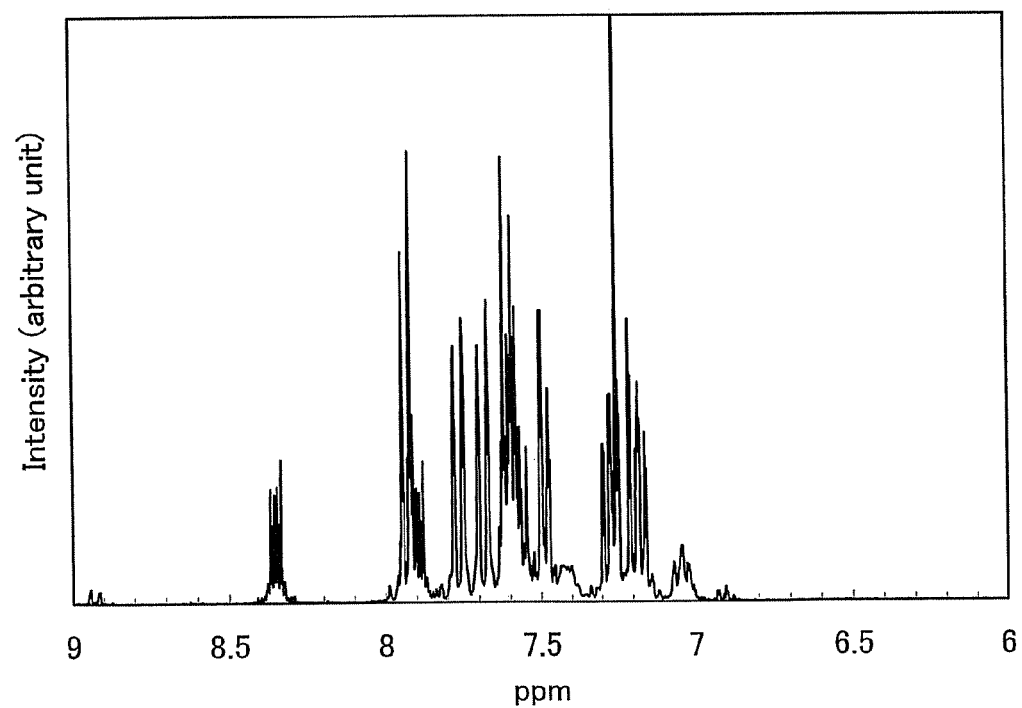

The analysis result of PAPQ by a proton nuclear magnetic resonance method ($^1$H NMR) was as follows: $^1$H NMR (300 MHz, CDCl$_3$): δ=7.03-7.07 (m, 1H), 7.16-7.21 (m, 5H), 7.24-7.30 (m, 4H), 7.47-7.50 (m, 4H), 7.55-7.63 (m, 10H), 7.67-7.70 (m, 4H), 7.75-7.78 (m, 4H), 7.88-7.95 (m, 6H). In addition, a $^1$H NMR chart is shown in each of FIGS. 15A and 15B. Note that FIG. 15B is a chart showing an enlargement of FIG. 15A in the range of 6.0 ppm to 9.0 ppm.

The thermogravimetry-differential thermal analysis (TG-DTA) of PAPQ was performed using a thermo-gravimetric/differential thermal analyzer (TG/DTA 320, product of Seiko Instruments Inc.), and a thermophysical property was evaluated under a nitrogen atmosphere and a rate of temperature increase of 10° C./min. As a result, based on the relationship between gravity and temperature (thermogravimetric measurement), the temperature at which the gravity is 95% or less of the gravity at the starting point of the measurement, under normal pressure, was 481° C., and high heat resistance was exhibited.

Figure 16:
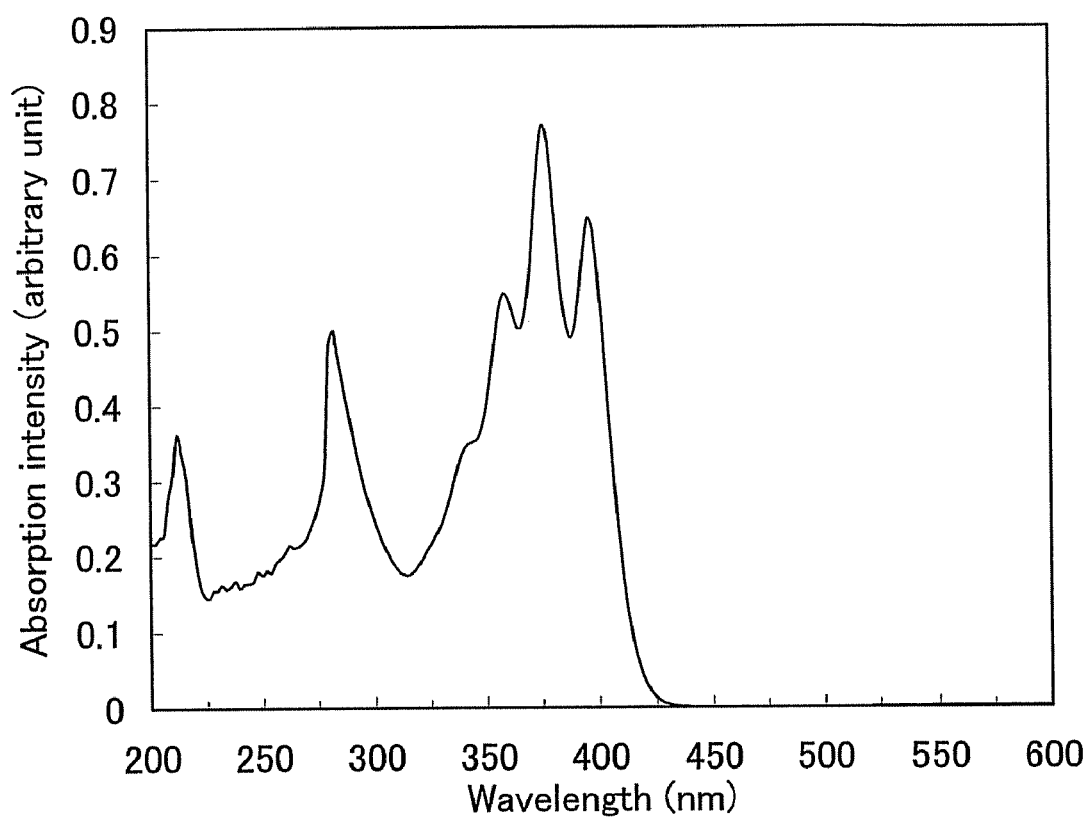
FIG. 16 is a graph showing an absorption spectrum of 2,3-bis[4-(9-phenyl-10-anthryl)phenyl]quinoxaline (abbreviation: PAPQ), which is a quinoxaline derivative of the present invention, in a toluene solution.
Figure 17:
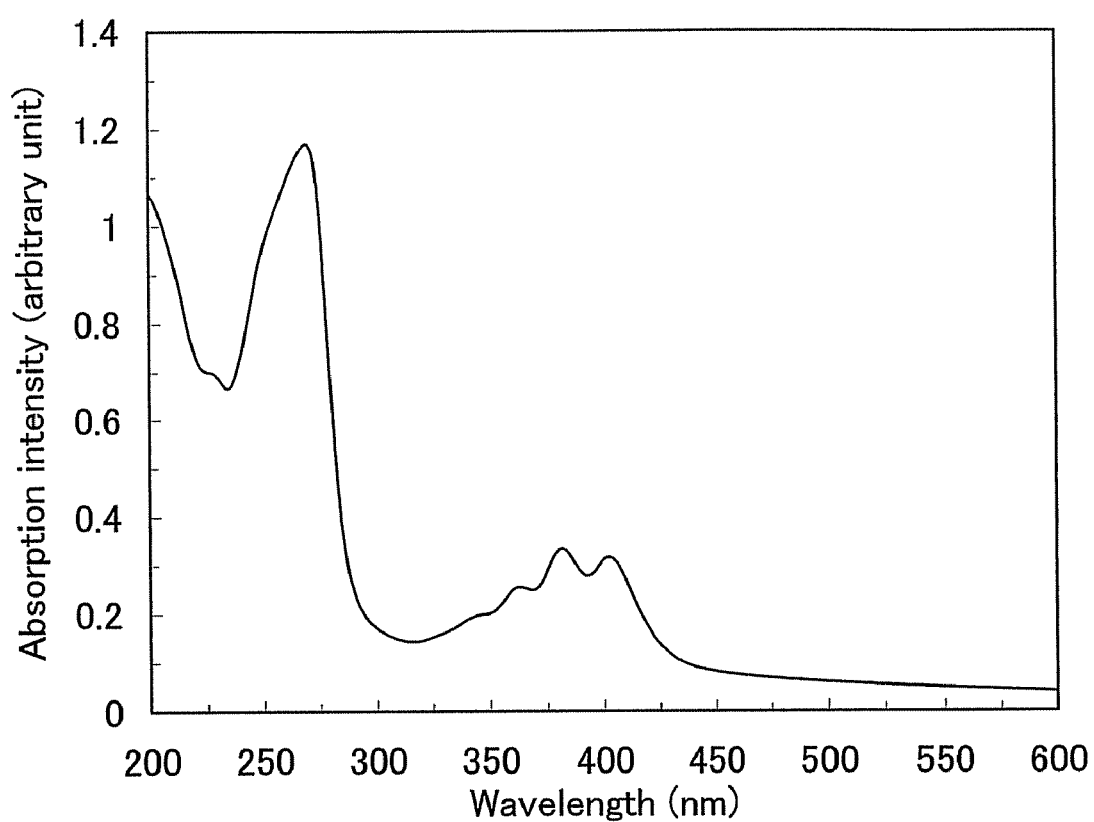
FIG. 17 is a graph showing an absorption spectrum of a thin film of 2,3-bis[4-(9-phenyl-10-anthryl)phenyl]quinoxaline (abbreviation: PAPQ), which is a quinoxaline derivative of the present invention.
Figure 18:
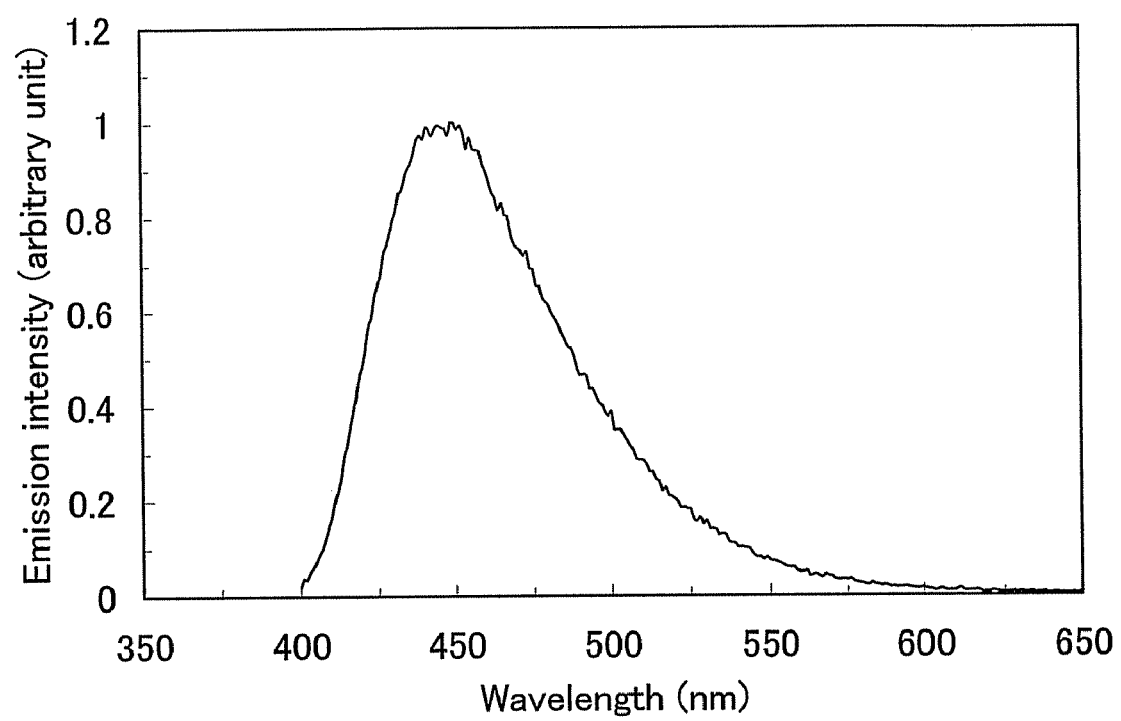
FIG. 18 is a graph showing an emission spectrum of 2,3-bis[4-(9-phenyl-10-anthryl)phenyl]quinoxaline (abbreviation: PAPQ), which is a quinoxaline derivative of the present invention, in a toluene solution.
Figure 19:
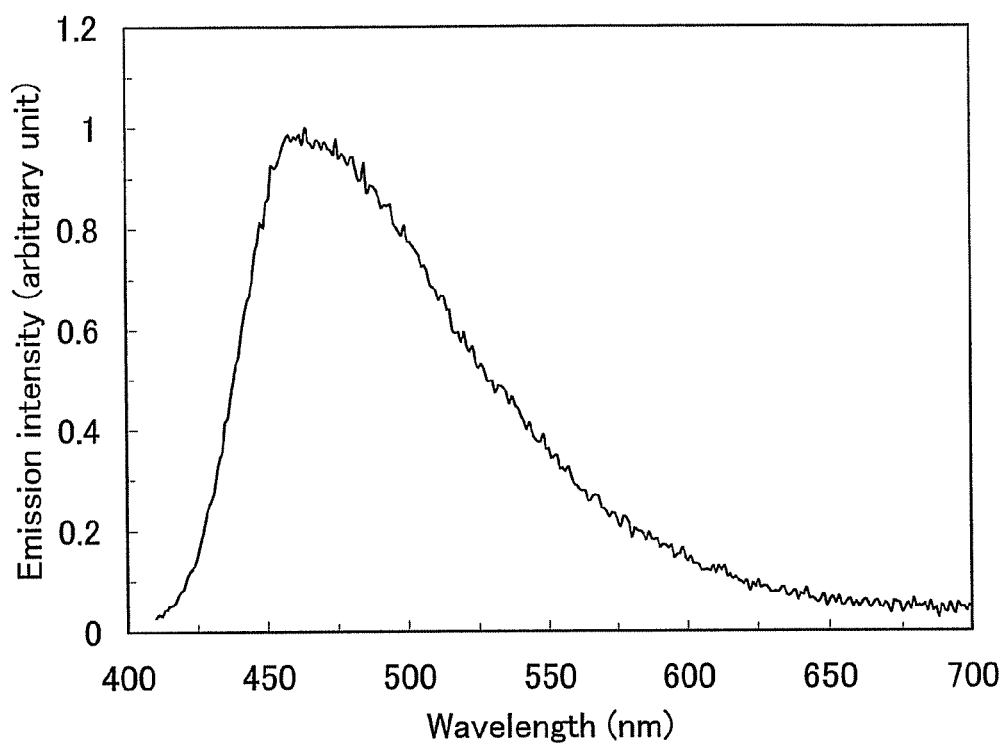
FIG. 19 is a graph showing an emission spectrum of a thin film of 2,3-bis[4-(9-phenyl-10-anthryl)phenyl]quinoxaline (abbreviation: PAPQ), which is a quinoxaline derivative of the present invention.

FIG. 16 shows an absorption spectrum of a toluene solution of PAPQ. FIG. 17 shows an absorption spectrum of a thin film of PAPQ. The measurement was conducted by using a UV-visible spectrophotometer (V-550, manufactured by JASCO Corporation). The solution was put in a quartz cell, and the thin film was evaporated on a quartz substrate to form the samples. The absorption spectra thereof, from each of which the absorption spectrum of quartz was subtracted, are shown in FIGS. 16 and 17. In FIGS. 16 and 17, the horizontal axis indicates a wavelength (nm) while the vertical axis indicates absorption intensity (arbitrary unit). In the case of the toluene solution, absorption was observed at around 358 nm, 376 nm, and 396 nm, and in the case of the thin film, absorption was observed at around 362 nm, 382 nm, and 402 nm. The emission spectrum of the toluene solution of PAPQ (excitation wavelength: 376 nm) is shown in FIG. 18, while that of the thin film of PAPQ (excitation wavelength: 402 nm) is shown in FIG. 19. In FIGS. 18 and 19, the horizontal axis indicates wavelength (nm) and the vertical axis indicates light emission intensity (arbitrary unit). The maximum light emission wavelength was 446 nm in the case of the toluene solution (excitation wavelength: 376 nm), and 464 nm in the case of the thin film (excitation wavelength: 402 nm).

In addition, the ionization potential of PAPQ in the thin film state was 5.76 eV, which was measured by a photoelectron spectrometer (AC-2, manufactured by Riken Keiki Co., Ltd.) in the air. As a result the HOMO level was found to be −5.76 eV. Moreover, the absorption edge was obtained from Tauc plot, with an assumption of direct transition, using data on the absorption spectrum of the thin film of PAPQ in FIG. 17. When the absorption edge was estimated as an optical energy gap, the energy gap was 2.92 eV. The LUMO level was calculated from the obtained value of the energy gap and the HOMO level, which was −2.84 eV.

Embodiment 3

In this embodiment, a synthesis example of 2,3-bis[4-(9,9-dimethylfluoren-2-yl)phenyl]quinoxaline (abbreviation: FPQ), which is a quinoxaline derivative of the present invention represented by Structural Formula (126) below, is specifically described.

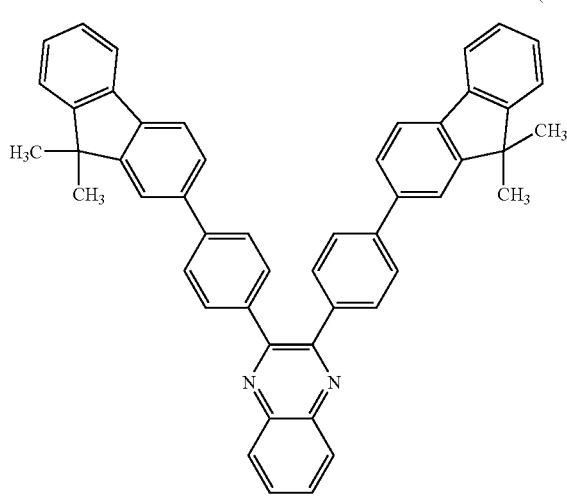

(126)

[Step 1] Synthesis of 2-iodo-9,9-dimethylfluorene

A synthesis method of 2-iodo-9,9-dimethylfluorene is described. A synthesis scheme of 2-iodo-9,9-dimethylfluorene is shown in (D-1).

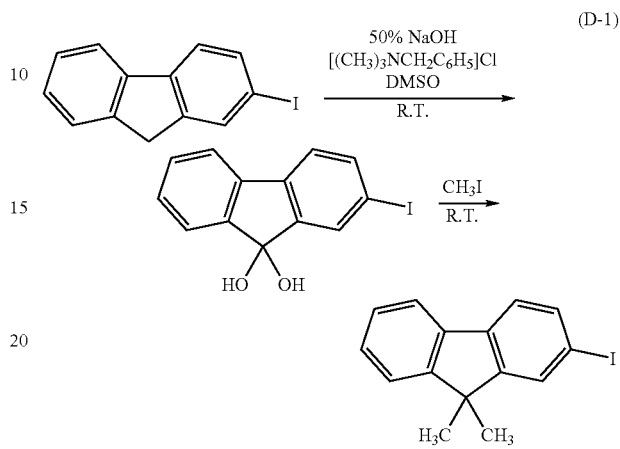

(D-1)

25 g (86 mmol) of 2-iodofluorene and 1.5 L of dimethylsulfoxide (abbreviation: DMSO) were put into a 2.0 L three-neck flask, and 1.0 g (5.4 mmol) of benzyltrimethylammonium chloride and 24 mL of 50% sodium hydroxide aqueous solution were added to the mixture. This mixture was stirred at room temperature for 3 hours. Thereafter, 19 g (130 mmol) of iodomethane was added to this reaction mixture and stirred at room temperature for 3 hours. After completion of the reaction, the reaction solution was washed with 1.0 mol/L hydrochloric acid, a water layer was extracted with ethyl acetate, combined with an organic layer and washed with saturated saline, and then dried with magnesium sulfate. After drying, the mixture was subjected to suction filtration, and a filtrate was concentrated. An obtained residue was purified by silica gel column chromatography (developing solvent: hexane), and an obtained solution was concentrated. When an obtained solid was recrystallized with a mixed solvent of chloroform and hexane, 24.7 g of a white, powdery solid of 2-iodo-9,9-dimethylfluorene, which was a target matter, was obtained with the yield of 90%.

[Step 2] Synthesis of FPQ

A synthesis method of 2,3-bis[4-(9,9-dimethylfluoren-2-yl)phenyl]quinoxaline (abbreviation: FPQ) is described. A synthesis scheme of FPQ is shown in (D-2).

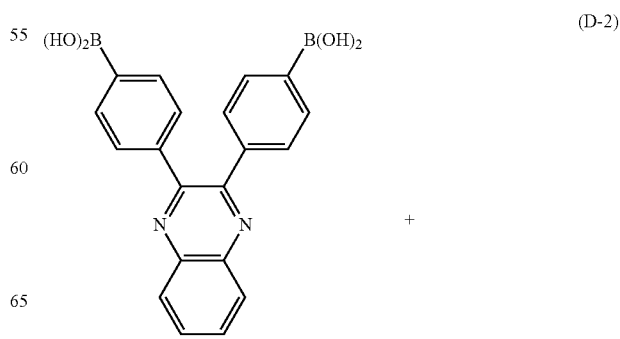

(D-2)

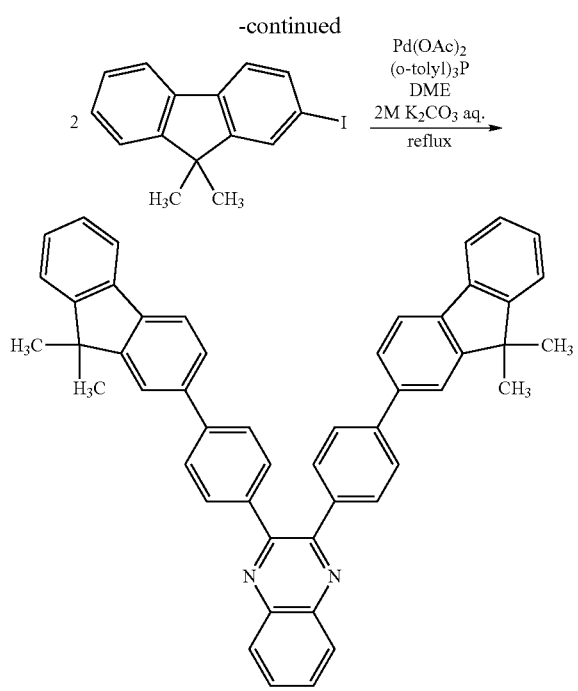

9.3 g (29 mmol) of 2-bromo-9,9-dimethylfluorene, 4.8 g (13 mmol) of 4,4'-(quinoxaline-2,3-diyl)diphenyl boronic acid that was synthesized in Embodiment 1, 0.065 g (0.29 mmol) of palladium(II) acetate, and 0.61 g (2.0 mmol) of tri(ortho-tolyl)phosphine were put into a 200 mL three-neck flask, and nitrogen substitution in the flask was carried out. Then, 60 mL of ethylene glycol dimethyl ether (abbreviation: DME) and 44 mL (87 mmol) of a potassium carbonate aqueous solution (2.0 mol/L) were added to this mixture. This mixture was refluxed under a nitrogen gas stream at 80° C. for 7 hours. After completion of a reaction, a precipitate in the reaction mixture was collected by suction filtration. An obtained solid was dissolved in chloroform, and suction filtration through Florisil, celite, and alumina was performed. When a filtrate was concentrated and an obtained solid was recrystallized with a mixed solvent of chloroform and hexane, 9.8 g of a light yellow, powdery solid that was a target matter, was obtained with the yield of 55%. By a nuclear magnetic resonance method (NMR), it was confirmed that this compound was 2,3-bis[4-(9,9-dimethylfluoren-2-yl)phenyl]quinoxaline (abbreviation: FPQ).

Figure 20A:
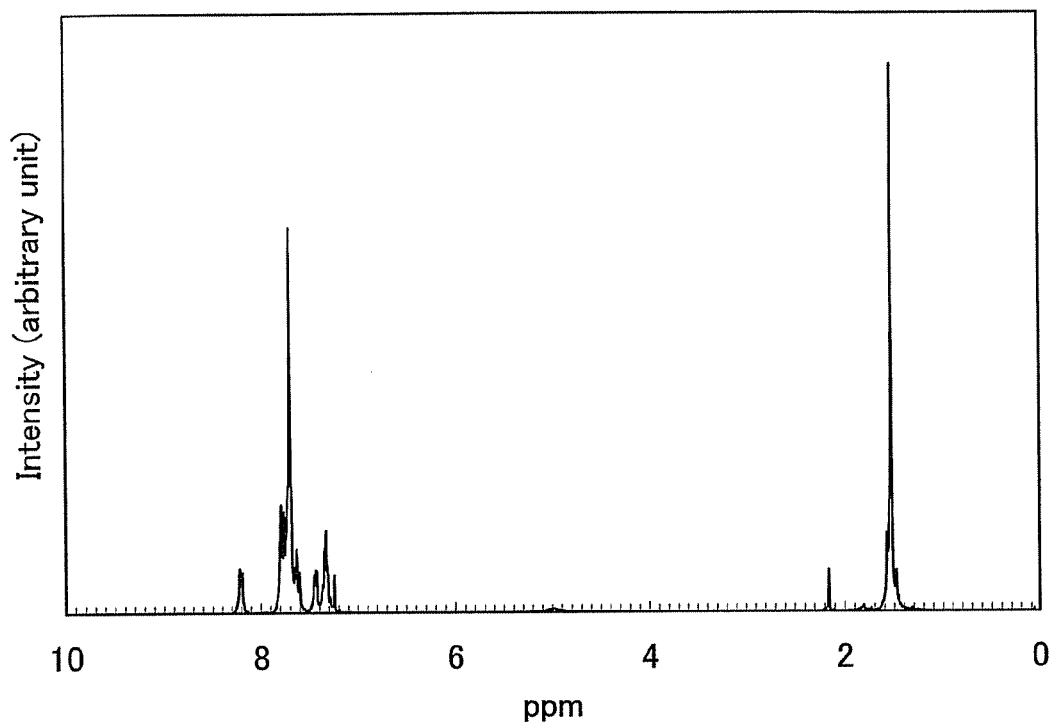
FIGS. 20A and 20B are each a graph showing a $^1$H NMR chart of 2,3-bis[4-(9,9-dimetheylfluoren-2-yl)phenyl] (abbreviation: FPQ), which is a quinoxaline derivative of the present invention.
Figure 20B:
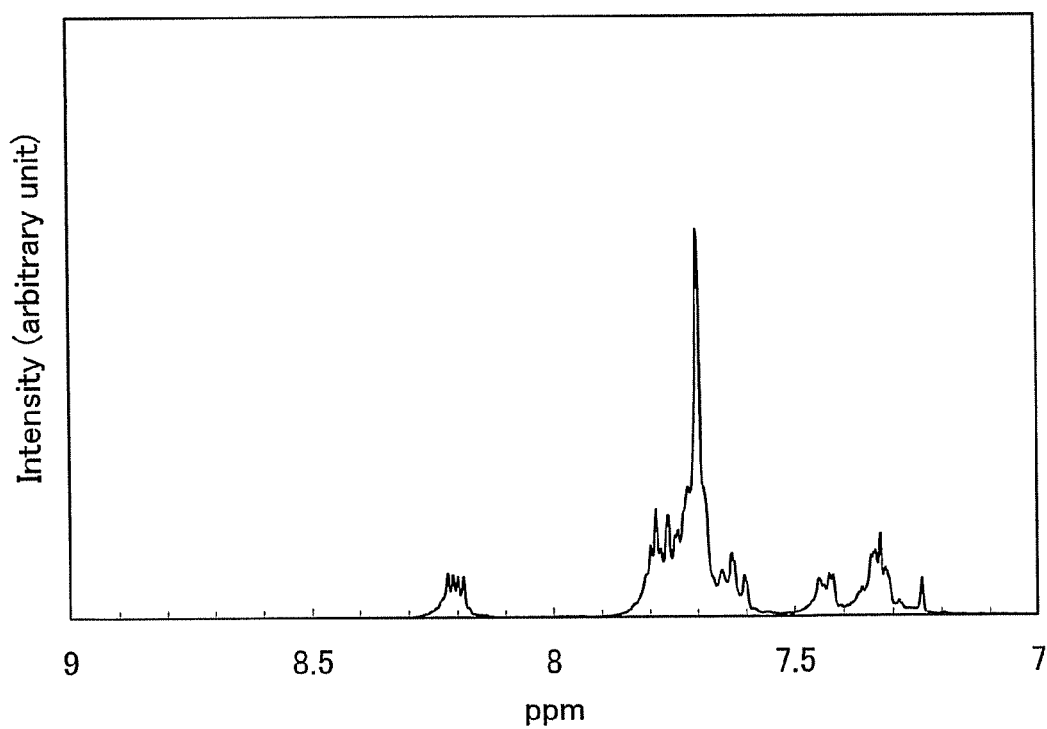

The analysis result of FPQ by a proton nuclear magnetic resonance method ($^1$H NMR) was as follows: $^1$H NMR (300 MHz, CDCl$_3$): δ=1.52 (s, 12H), 7.24-7.45 (m, 6H), 7.60-7.80 (m, 18H), 8.19-8.22 (m, 2H). In addition, a $^1$H NMR chart is shown in each of FIGS. 20A and 20B. Note that FIG. 20 is a chart showing an enlargement of FIG. 20A in the range of 7.0 ppm to 9.0 ppm.

The thermogravimetry-differential thermal analysis (TG-DTA) of FPQ was performed using a thermo-gravimetric/differential thermal analyzer (TG/DTA 320, product of Seiko Instruments Inc.), and a thermophysical property was evaluated under a nitrogen atmosphere and a rate of temperature increase of 10° C./min. As a result, based on the relationship between gravity and temperature (thermogravimetric measurement), the temperature at which the gravity is 95% or less of the gravity at the starting point of the measurement, under normal pressure, was 414° C., and high heat resistance was exhibited.

Figure 21:
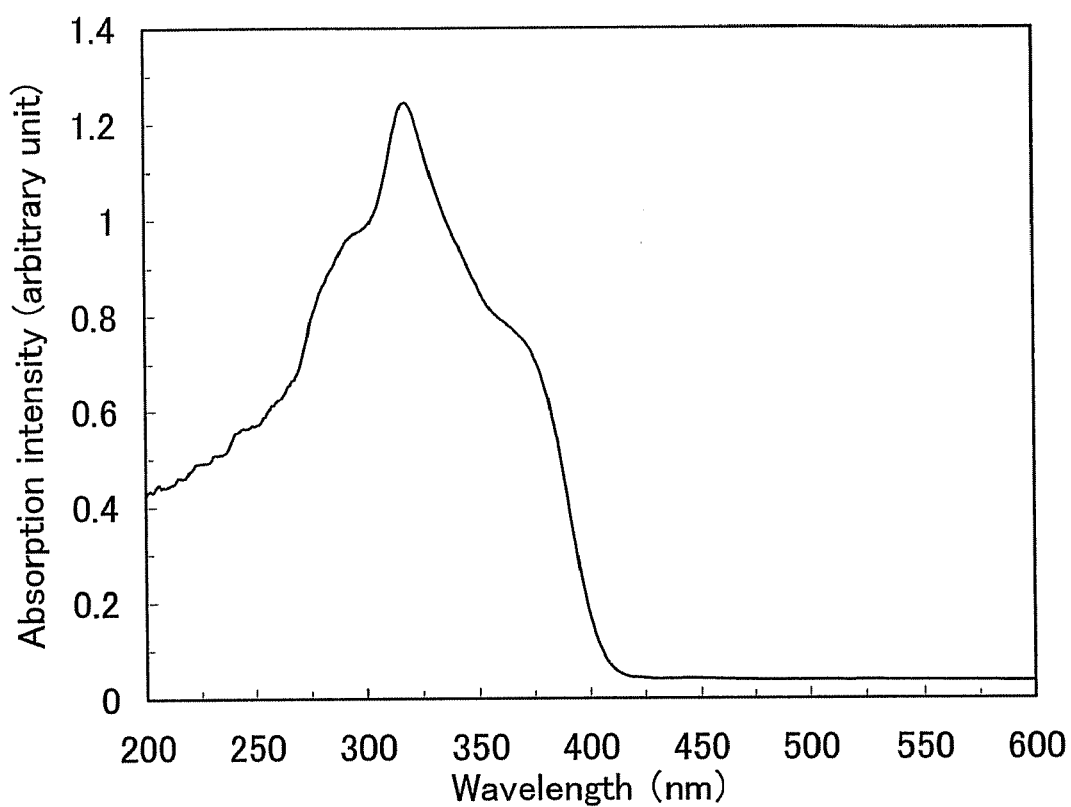
FIG. 21 is a graph showing an absorption spectrum of 2,3-bis[4-(9,9-dimetheylfluoren-2-yl)phenyl] (abbreviation: FPQ), which is a quinoxaline derivative of the present invention, in a toluene solution.
Figure 22:
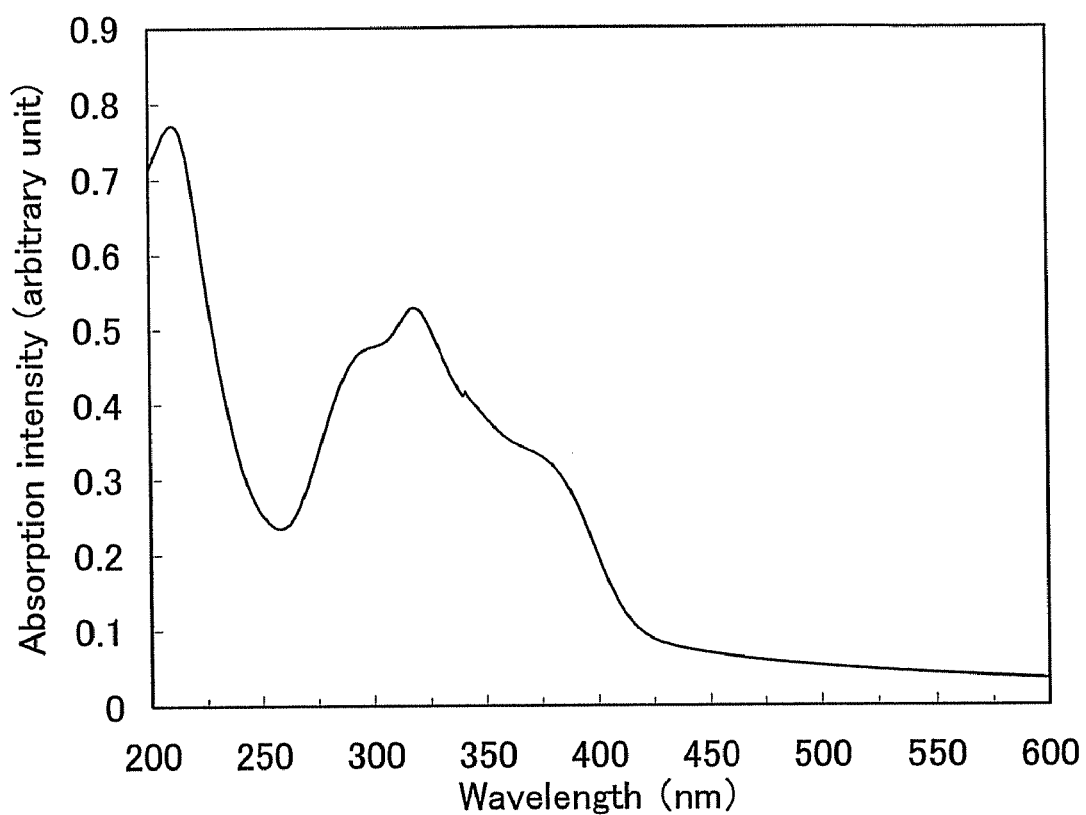
FIG. 22 is a graph showing an absorption spectrum of a thin film of 2,3-bis[4-(9,9-dimetheylfluoren-2-yl)phenyl] (abbreviation: FPQ), which is a quinoxaline derivative of the present invention.
Figure 23:
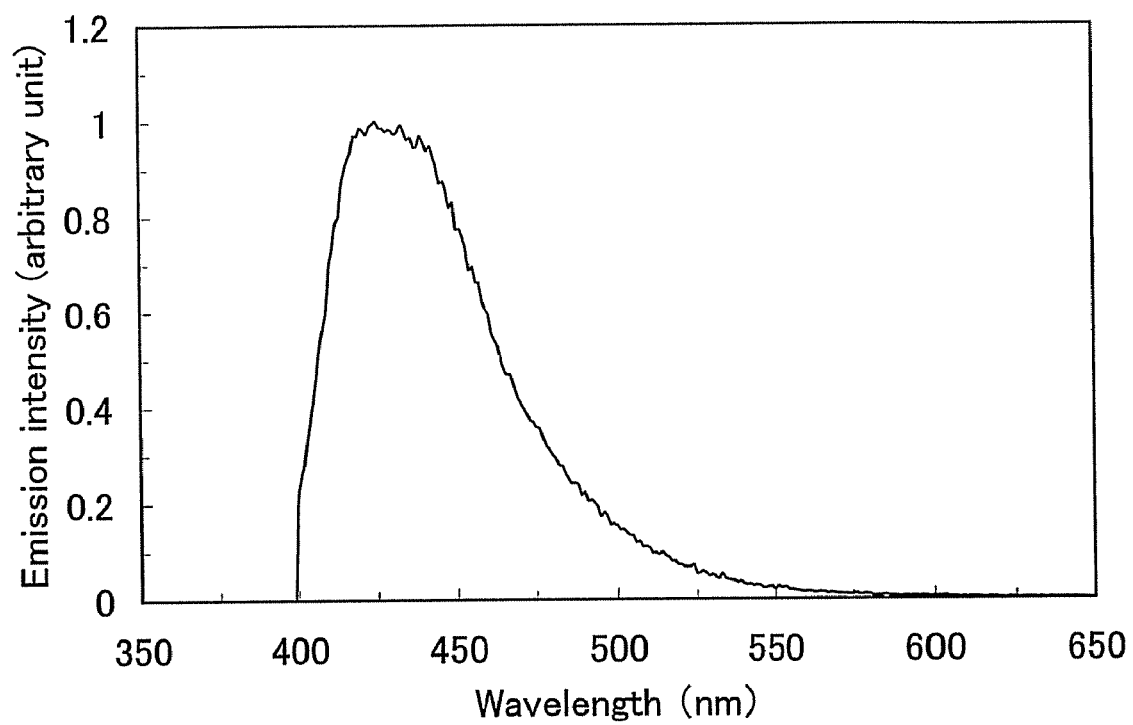
FIG. 23 is a graph showing an emission spectrum of 2,3-bis[4-(9,9-dimetheylfluoren-2-yl)phenyl] (abbreviation: FPQ), which is a quinoxaline derivative of the present invention, in a toluene solution.
Figure 24:
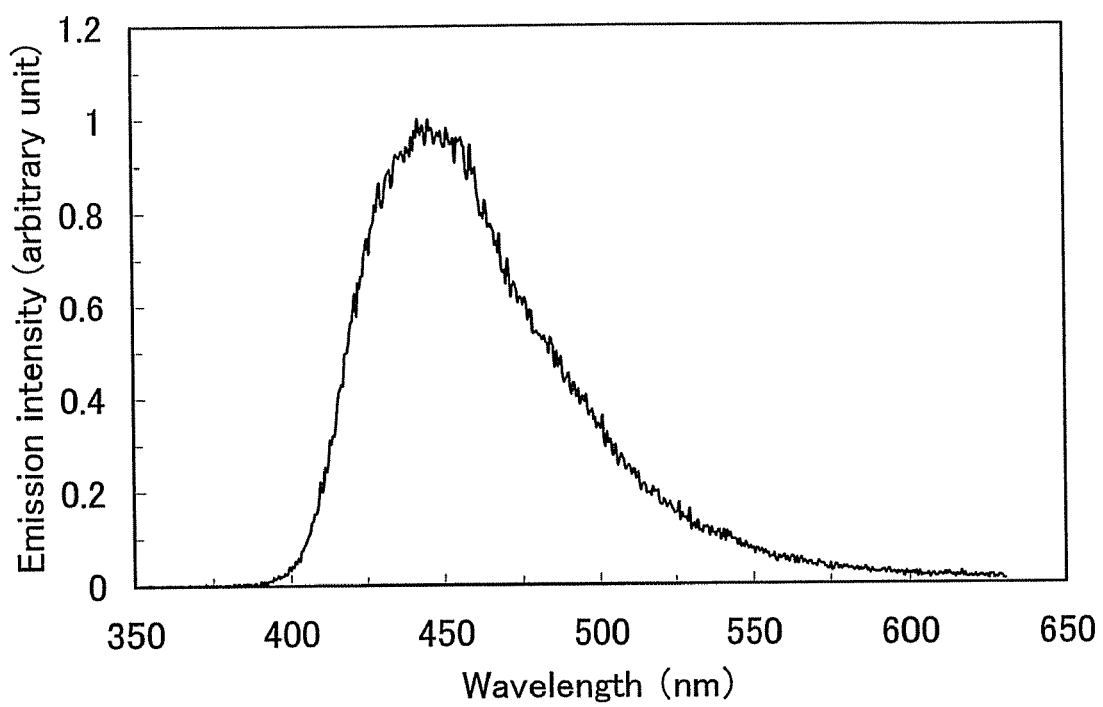
FIG. 24 is a graph showing an emission spectrum of a thin film of 2,3-bis[4-(9,9-dimetheylfluoren-2-yl)phenyl] (abbreviation: FPQ), which is a quinoxaline derivative of the present invention.

FIG. 21 shows an absorption spectrum of a toluene solution of FPQ. FIG. 22 shows an absorption spectrum of a thin film of FPQ. The measurement was conducted by using a UV-visible spectrophotometer (V-550, manufactured by JASCO Corporation). The solution was put in a quartz cell, and the thin film was evaporated on a quartz substrate to form the samples. The absorption spectra thereof, from each of which the absorption spectrum of quartz was subtracted, are shown in FIGS. 21 and 22. In FIGS. 21 and 22, the horizontal axis indicates a wavelength (nm) while the vertical axis indicates absorption intensity (arbitrary unit). In the case of the toluene solution, absorption was observed at around 318 nm, and in the case of the thin film, absorption was observed at around 318 nm. The emission spectrum of the toluene solution of FPQ (excitation wavelength: 378 nm) is shown in FIG. 23, while that of the thin film of FPQ (excitation wavelength 378 nm) is shown in FIG. 24. In FIGS. 23 and 24, the horizontal axis indicates wavelength (nm) and the vertical axis indicates light emission intensity (arbitrary unit). The maximum light emission wavelength was 425 nm in the case of the toluene solution (excitation wavelength: 378 nm), and 445 nm in the case of the thin film (excitation wavelength: 378 nm).

In addition, the ionization potential of FPQ in the thin film state was 5.64 eV, which was measured by a photoelectron spectrometer (AC-2, manufactured by Riken Keiki Co., Ltd.) in the air. As a result, the HOMO level was found to be −5.64 eV. Moreover, the absorption edge was obtained from Tauc plot with an assumption of direct transition, using data on the absorption spectrum of the thin film of FPQ in FIG. 22. When the absorption edge was estimated as an optical energy gap, the energy gap was 2.92 eV. The LUMO level was calculated from the obtained value of the energy gap and the HOMO level, which was −2.72 eV.

Embodiment 4

In this embodiment, a synthesis example of 2,3-bis[4-(spiro-9,9'-bifluoren-2-yl)phenyl]quinoxaline (abbreviation: SFPQ), which is a quinoxaline derivative of the present invention represented by Structural Formula (144) below, is specifically described.

(144)

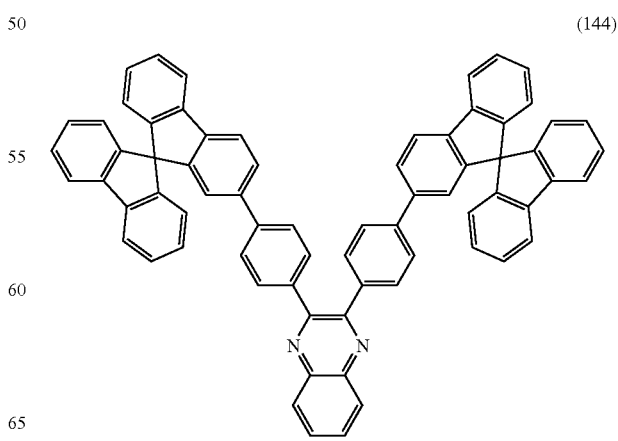

[Step 2] Synthesis of 2-bromo-9-fluorenone

A synthesis method of 2-bromo-9-fluorenone is described. A synthesis scheme of 2-bromo-9-fluorenone is described in (E-1).

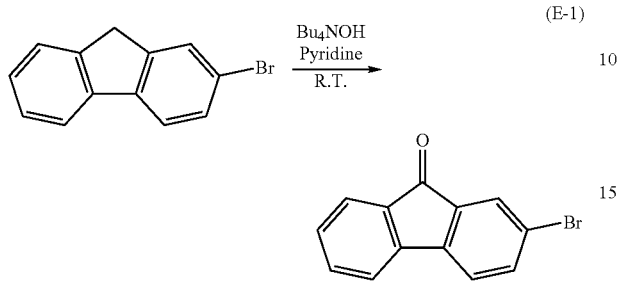

(E-1)

9.8 g (40 mmol) of 2-bromofluorene, 40 mL of pyridine, and 1.5 mL of tetrabutylammonium hydroxide (1.0 mol/1 methanol solution) were put into a 200 mL three-neck flask. This solution was stirred under air at room temperature for 24 hours. After completion of a reaction, 40 m/L of glacial acetic acid was added to the reaction solution and stirred for 1 hour. Then, the reaction solution was washed with water and a water layer was extracted with ethyl acetate. The extracted solution and an organic layer were combined and washed with saturated saline, and then dried with magnesium sulfate. After drying, this mixture was subjected to suction filtration, and a filtrate was concentrated. When an obtained solid was recrystallized with ethanol, 7.9 g of a yellow, powdery solid of 2-bromo-9-fluorenone that was a target matter was obtained with the yield of 76%.

[Step 2] Synthesis of 9-(biphenyl-2-yl)-2-bromofluoren-9-ol

A synthesis method of 9-(biphenyl-2-yl)-2-bromofluoren-9-ol is described. A synthesis scheme of 9-(biphenyl-2-yl)-2-bromofluoren-9-ol is shown in (E-2) and (E-3).

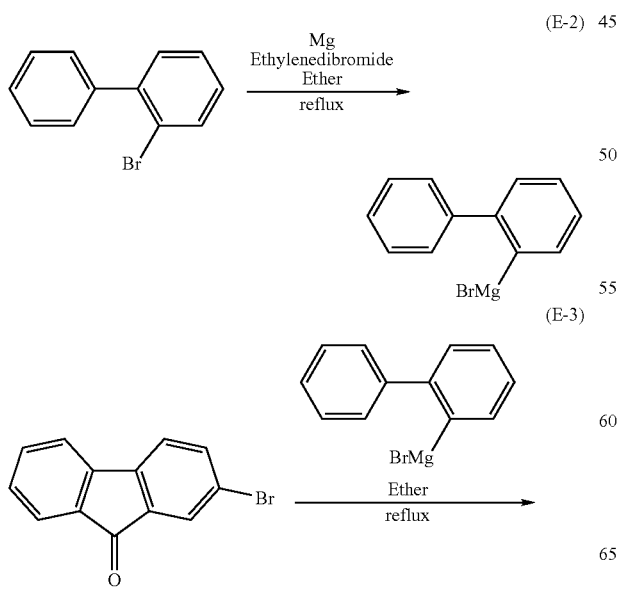

(E-2)

(E-3)

-continued

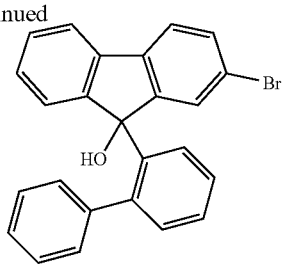

1.3 g (52 mmol) of magnesium was put into a 200 mL three-neck flask and stirred for 0.5 hours while reducing pressure with a rotary pump. Then, under a nitrogen gas stream, 5.0 mL of diethyl ether and one drop of dibromoethane were added. A solution in which 12 g (50 mmol) of 2-bromophenyl was dissolved in 15 mL of diethyl ether was dropped into this mixture at a pace that maintained reflux flow. After completion of dropping, the reaction mixture was refluxed at 50° C. for 3 hours so as to become a Grignard reagent. 12 g (45 mmol) of 2-bromo-9-fluorenone was put into a 200 mL three-neck flask, and after nitrogen substitution in the flask was carried out, 40 mL of diethyl ether was added into the flask. The synthesized Grignard reagent was dropped into this solution, and after completion of dropping, the solution was refluxed at 50° C. for 3 hours, and then stirred at room temperature for 24 hours. After completion of a reaction, the reaction solution was washed with water, and a water layer was extracted with ethyl acetate. The extracted solution and an organic layer were combined and washed with saturated saline, and then dried with magnesium sulfate. After drying, this mixture was subjected to suction filtration, and when a filtrate was concentrated, 19 g of a light yellow, powdery solid of 9-(biphenyl-2-yl)-2-bromofluoren-9-ol that was a target matter was obtained with the yield of 91%.

[Step 3] Synthesis of 2-bromospiro-9,9'-bifluorene

A synthesis method of 2-bromospiro-9,9'-bifluorene is described. A synthesis scheme of 2-bromospiro-9,9'-bifluorene is shown in (E-4).

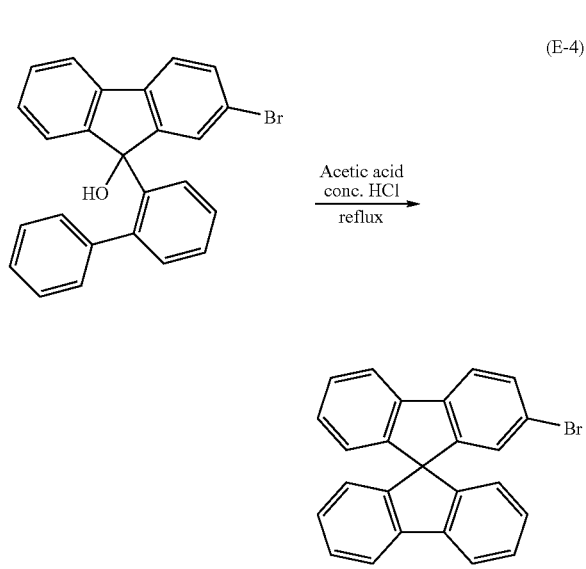

(E-4)

19 g (45 mmol) of 9-(biphenyl-2-yl)-2-bromofluoren-9-ol, 100 mL of glacial acetic acid, and a few drops of concentrated hydrochloric acid were put into a 300 mL three-neck flask, and this solution was refluxed at 120° C. for 2 hours. After completion of a reaction, a sodium hydrogen carbonate aqueous solution was added to the reaction mixture, and a precipitate in this mixture was collected by suction filtration. An obtained solid was washed with water, and 10 g of a light yellow, powdery solid of 2-bromospiro-9,9'-bifluorene, which was a target matter, was obtained with the yield of 57%.

[Step 4] Synthesis of SFPQ

A synthesis method of 2,3-bis[4-(spiro-9,9'-bifluoren-2-yl)phenyl]quinoxaline (abbreviation: SFPQ) is described. A synthesis scheme of SFPQ is shown in (E-5).

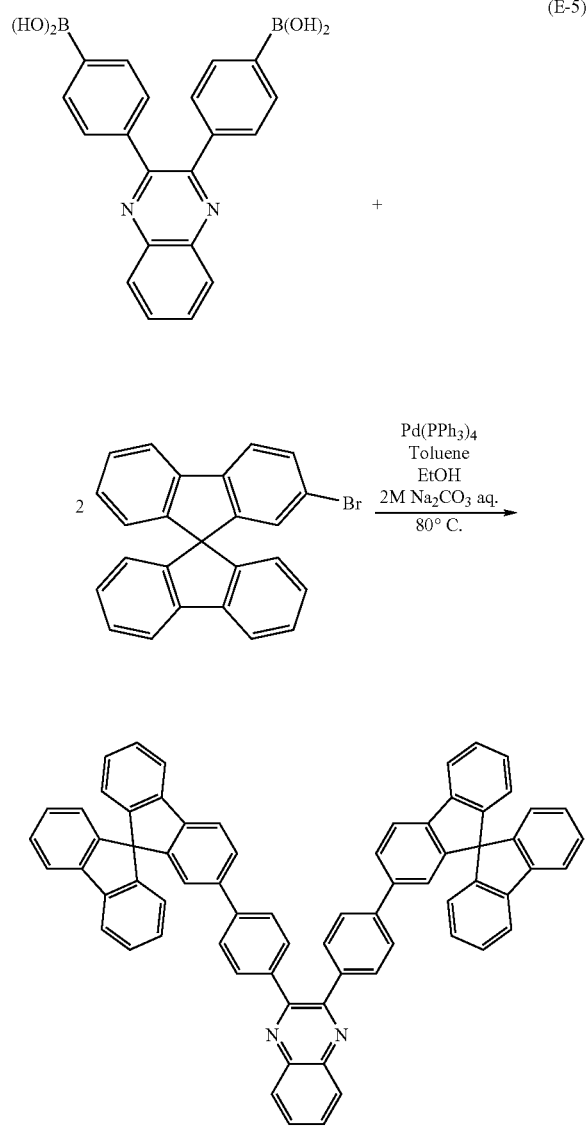

12 g (30 mmol) of 2-bromospiro-9,9'-bifluorene, 5.0 g (14 mmol) of 4,4'-(quinoxaline-2,3-diyl)diphenyl boronic acid that was synthesized in Embodiment 1, and 0.70 g (0.60 mmol) of tetrakis(triphenylphosphine)palladium(0) were put into a 300 mL three-neck flask, and nitrogen substitution in the flask was carried out. Then, 80 mL of toluene, 10 mL of ethanol, and 40 mL (80 mmol) of a sodium carbonate aqueous solution (2.0 mol/L) were added to this mixture. This mixture was stirred under a nitrogen gas stream at 80° C. for 7 hours. After completion of a reaction, a precipitate in the reaction mixture was collected by suction filtration. An obtained solid was dissolved in chloroform, and suction filtration through Florisil, celite, and alumina was performed. When a filtrate was concentrated and an obtained solid was recrystallized with a mixed solvent of chloroform and hexane, 9.5 g of a light yellow, powdery solid that was a target matter, was obtained with the yield of 77%. By a nuclear magnetic resonance method (NMR), it was confirmed that this compound was 2,3-bis[4-(spiro-9,9'-bifluoren-2-yl)phenyl]quinoxaline (abbreviation: SFPQ).

Figure 25A:
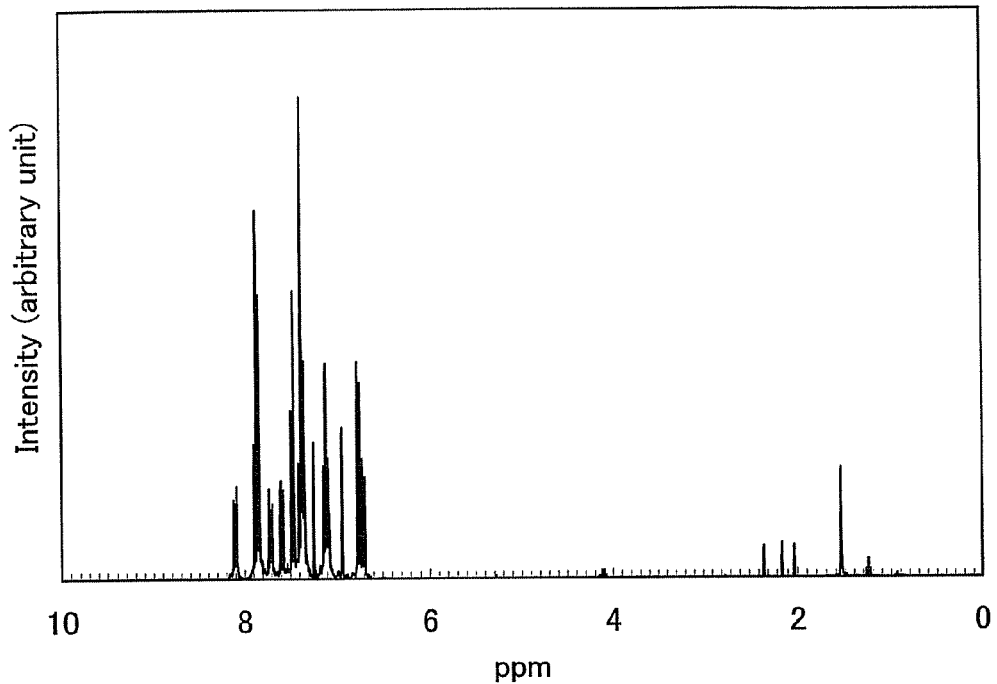
FIGS. 25A and 25B are each a graph showing a $^1$H NMR chart of 2,3-bis[4-(spiro-9,9-bifluoren-2-yl)phenyl]quinoxaline (abbreviation: SFPQ), which is a quinoxaline derivative of the present invention.
Figure 25B:
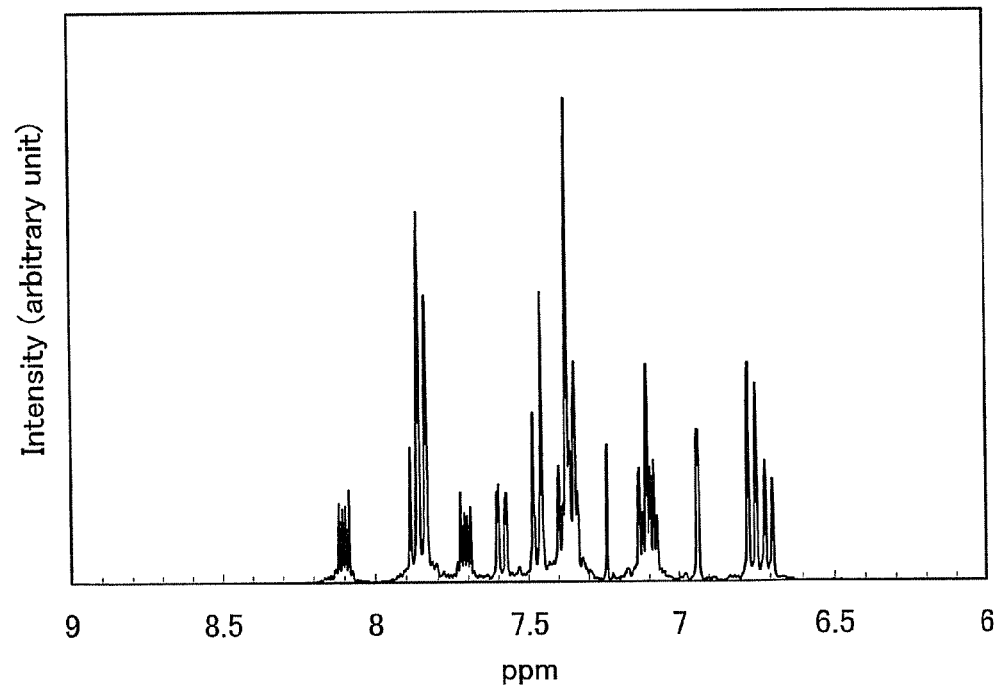

The analysis result of SFPQ by a proton nuclear magnetic resonance method ($^1$H NMR) was as follows: $^1$H NMR (300 MHz, CDCl$_3$): δ=6.69-6.77 (m, 6H), 6.94-6.94 (m, 2H), 7.07-7.14 (m, 6H), 7.34-7.40 (m, 10H), 7.46-7.49 (m, 4H), 7.57-7.60 (m, 2H), 7.69-7.72 (m, 2H), 7.84-7.89 (m, 8H), 8.09-8.12 (m, 2H). In addition, a $^1$H NMR chart is shown in each of FIGS. 25A and 25B. Note that FIG. 25B is a chart showing an enlargement of FIG. 25A in the range of 6.0 ppm to 9.0 ppm.

The thermogravimetry-differential thermal analysis (TG-DTA) of SFPQ was performed using a thermo-gravimetric/differential thermal analyzer (TG/DTA 320, product of Seiko Instruments Inc.), and a thermophysical property was evaluated under a nitrogen atmosphere and a rate of temperature increase of 10° C./min. As a result, based on the relationship between gravity and temperature (thermogravimetric measurement), the temperature at which the gravity is 95% or less of the gravity at the starting point of the measurement, under normal pressure, was 437° C., and high heat resistance was exhibited.

Figure 26:
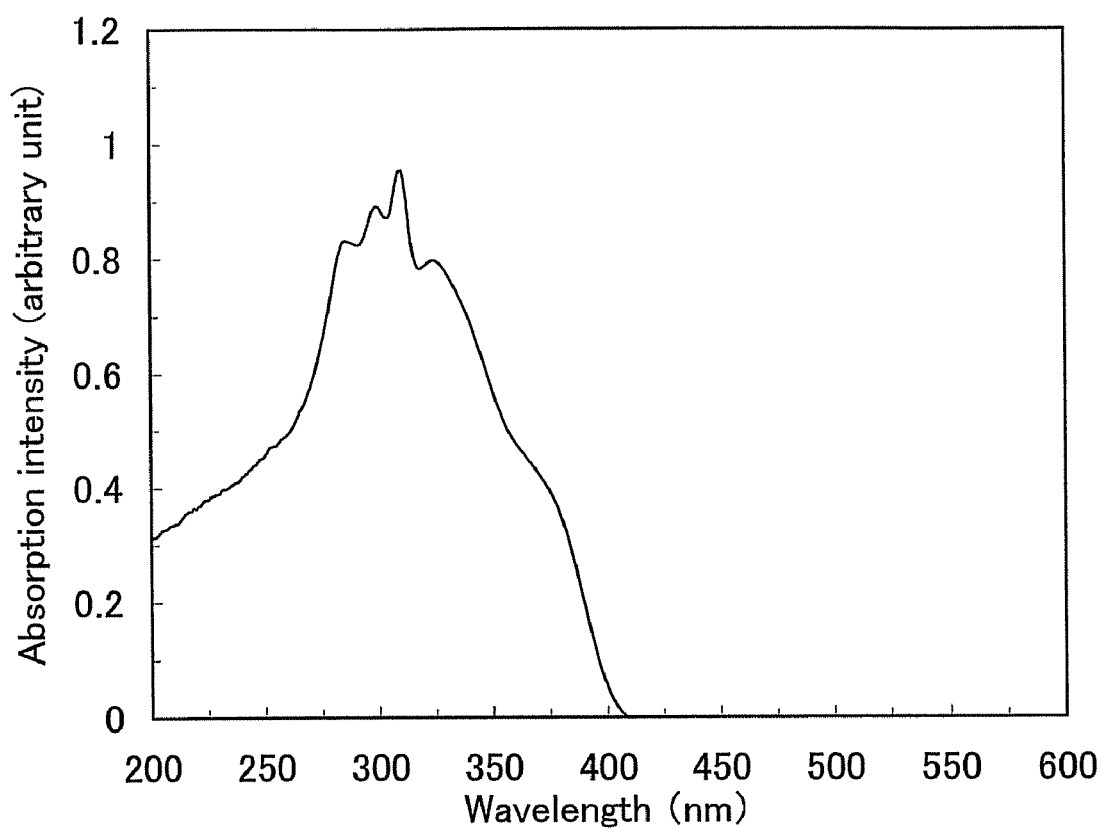
FIG. 26 is a graph showing an absorption spectrum of 2,3-bis[4-(spiro-9,9'-bifluoren-2-yl)phenyl]quinoxaline (abbreviation: SFPQ), which is a quinoxaline derivative of the present invention, in a toluene solution.
Figure 27:
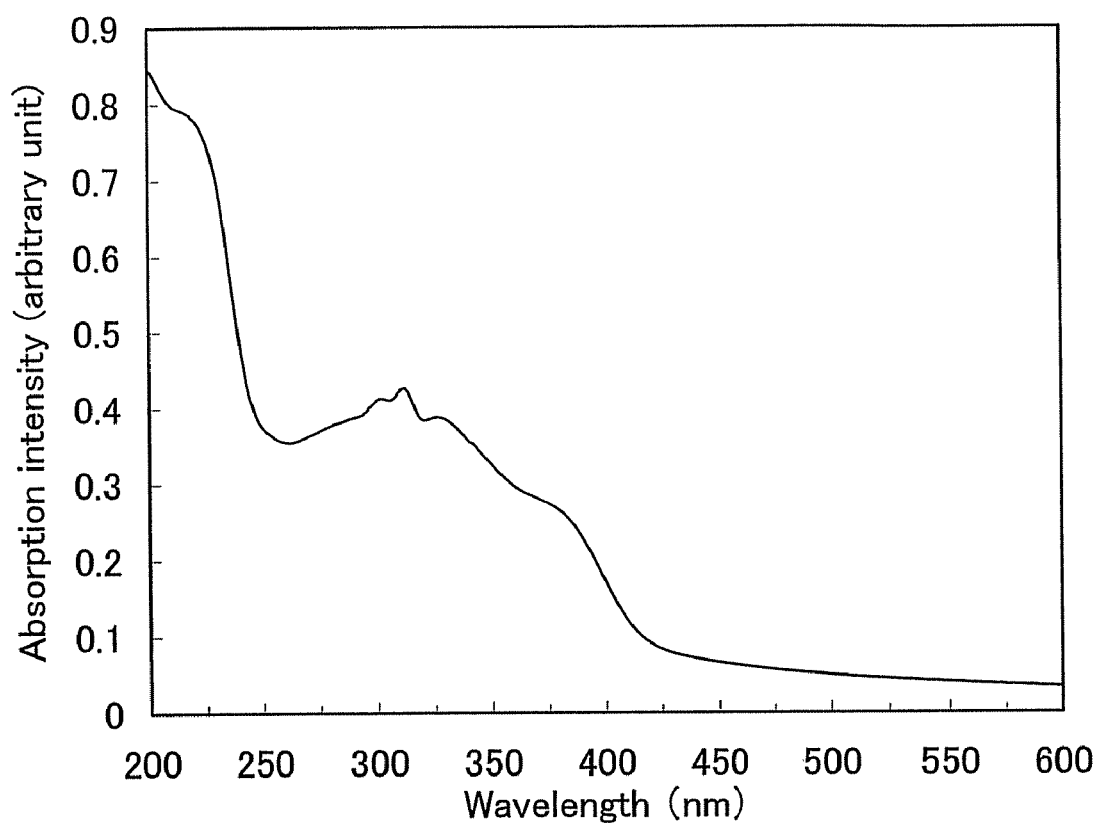
FIG. 27 is a graph showing an absorption spectrum of a thin film of 2,3-bis[4-(spiro-9,9'-bifluoren-2-yl)phenyl]quinoxaline (abbreviation: SFPQ), which is a quinoxaline derivative of the present invention.
Figure 28:
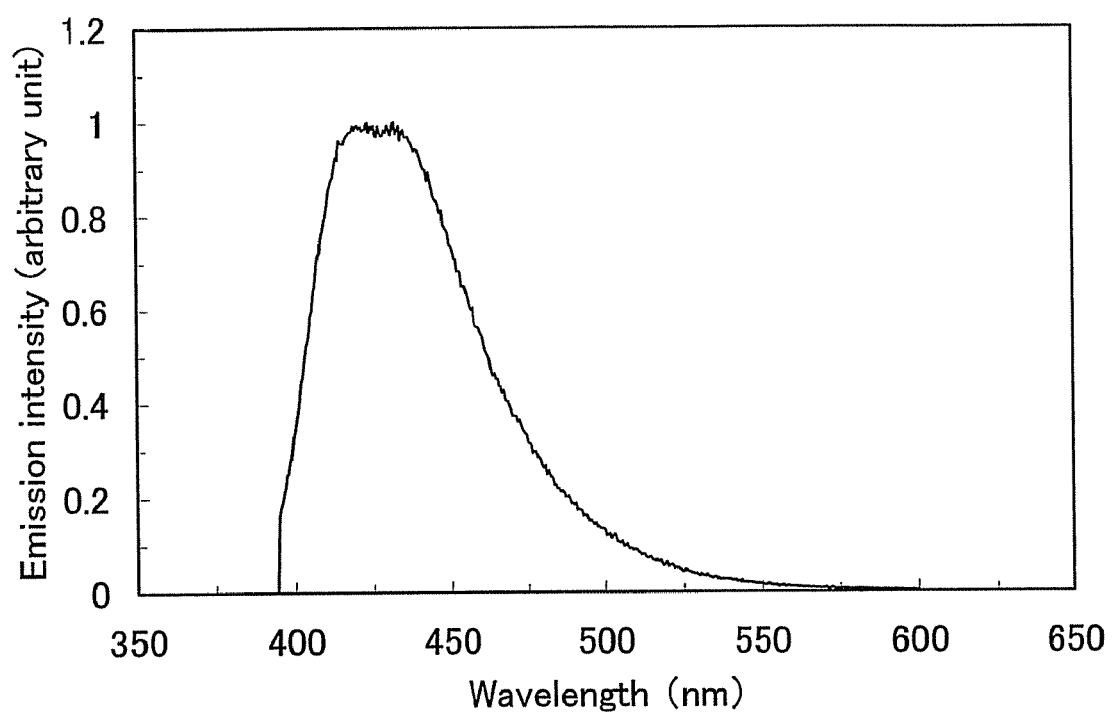
FIG. 28 is a graph showing an emission spectrum of 2,3-bis[4-(spiro-9,9'-bifluoren-2-yl)phenyl]quinoxaline (abbreviation: SFPQ), which is a quinoxaline derivative of the present invention, in a toluene solution.
Figure 29:
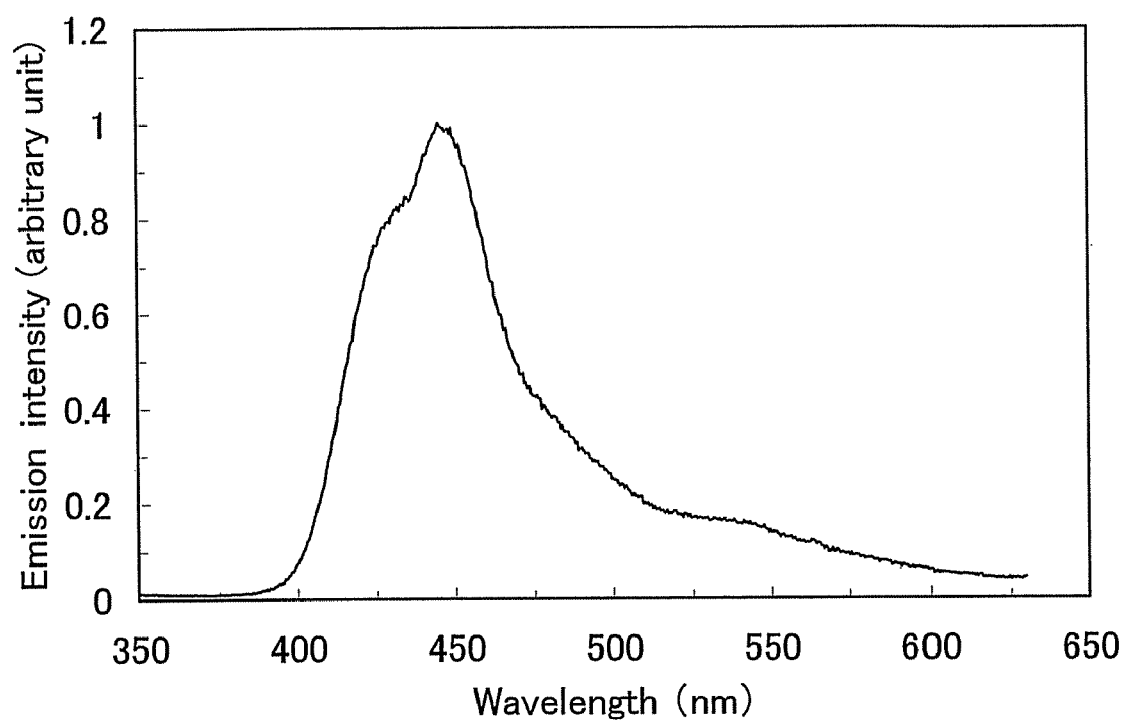
FIG. 29 is a graph showing an emission spectrum of a thin film of 2,3-bis[4-(spiro-9,9'-bifluoren-2-yl)phenyl]quinoxaline (abbreviation: SFPQ), which is a quinoxaline derivative of the present invention.

FIG. 26 shows an absorption spectrum of a toluene solution of SFPQ. FIG. 27 shows an absorption spectrum of a thin film of SFPQ. The measurement was conducted by using a UV-visible spectrophotometer (V-550, manufactured by JASCO Corporation). The solution was put in a quartz cell, and the thin film was evaporated on a quartz substrate to form the samples. The absorption spectra thereof from each of which the absorption spectrum of quartz was subtracted, are shown in FIGS. 26 and 27. In FIGS. 26 and 27, the horizontal axis indicates a wavelength (nm) while the vertical axis indicates absorption intensity (arbitrary unit). In the case of the toluene solution, absorption was observed at around 310 nm, and in the case of the thin film, absorption was observed at around 310 nm. The emission spectrum of the toluene solution of SFPQ (excitation wavelength: 374 nm) is shown in FIG. 28, while that of the thin film of SFPQ (excitation wavelength 310 nm) is shown in FIG. 29. In FIGS. 28 and 29, the horizontal axis indicates wavelength (nm) and the vertical axis indicates light emission intensity (arbitrary unit). The maximum light emission wavelength was 426 nm in the case of the toluene solution (excitation wavelength: 374 nm), and 446 nm in the case of the thin film (excitation wavelength: 310 nm).

In addition, the ionization potential of SFPQ in the thin film state was 5.72 eV, which was measured by a photoelectron spectrometer (AC-2, manufactured by Riken Keiki Co., Ltd.) in the air. As a result, the HOMO level was found to be −5.72 eV. Moreover, the absorption edge was obtained from Tauc plot, with an assumption of direct transition, using data on the absorption spectrum of the thin film of SFPQ in FIG. 27. When the absorption edge was estimated as an optical energy gap, the energy gap was 2.92 eV. The LUMO level was calculated from the obtained value of the energy gap and the HOMO level, which was −2.80 eV.

Embodiment 5

Figure 9:
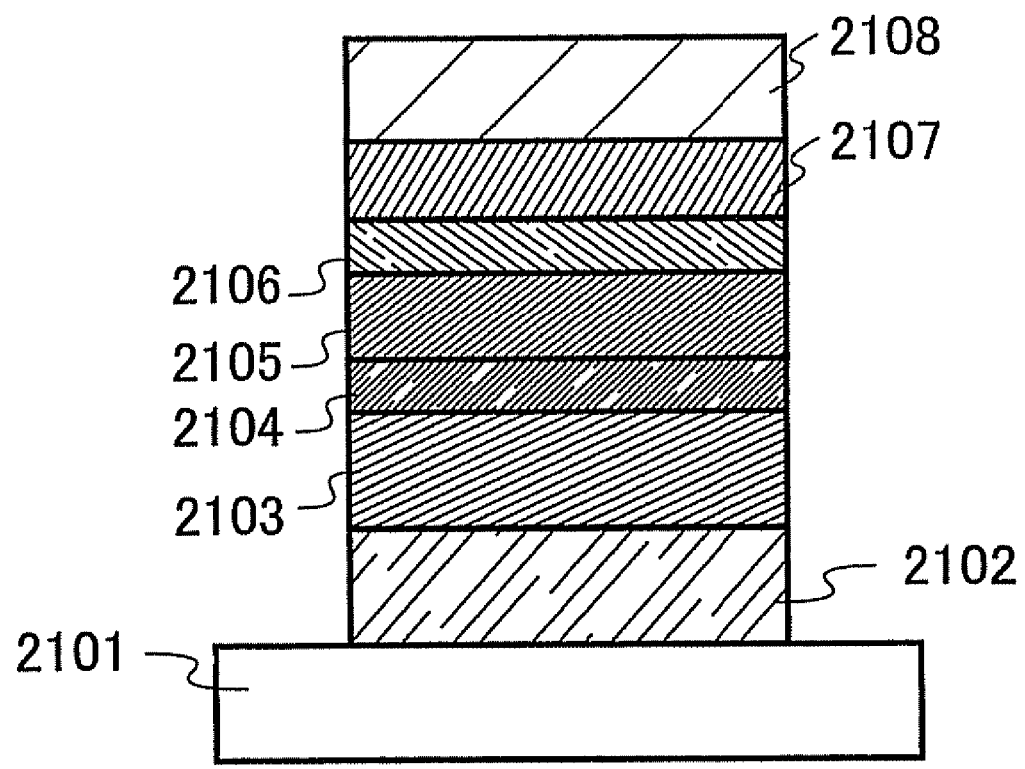
FIG. 9 is a view explaining a light-emitting element of embodiments.

In this embodiment, a light-emitting element of the present invention is described with reference to FIG. 9. A chemical formula of a material used in the embodiment hereinafter is shown below.

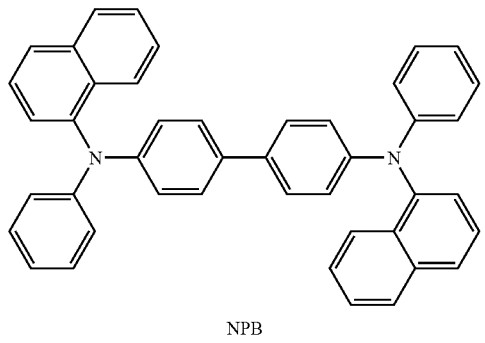

NPB

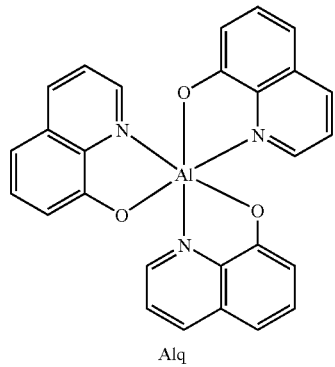

Alq

A manufacturing method of a light-emitting element of this embodiment is shown below.

(Light-Emitting Element 1)

First, indium tin oxide containing silicon oxide (ITSO) was deposited over a glass substrate 2101 by a sputtering method, so that a first electrode 2102 was formed. It is to be noted that the thickness thereof was 110 nm and an electrode area was 2 nm×2 nm.

Next, the substrate over which the first electrode was formed was fixed to a substrate holder provided in a vacuum evaporation apparatus in such a way that a surface of the substrate having the first electrode faced downward. The pressure was reduced to be about $10^{-4}$ Pa and then, 4,4'-bis[N-(1-napthyl)-N-phenylamino]biphenyl (abbreviation: NPB) and molybdenum oxide(VI) were co-evaporated on the first electrode 2102, thereby forming a layer 2103 containing a composite material of an organic compound and an inorganic compound. The film thickness of the layer 2103 was 50 nm, and the weight ratio between NPB and molybdenum oxide(VI) was set 4:1 (=NPB:molybdenum oxide). It is to be noted that the co-evaporation method is an evaporation method in which evaporation is performed at one time from plural evaporation sources in one process chamber.

Subsequently, a hole-transporting layer 2104 was formed having a thickness of 10 nm over the layer 2103 containing a composite material using 4,4'-bis[N-(1-napthyl)-N-phenylamino]biphenyl (abbreviation: NPB) by an evaporation method using resistance heating.

Further, a light-emitting layer 2105 having a thickness of 30 nm was formed over the hole-transporting layer 2104 by evaporating 2,3-bis[4-(10-anthryl)phenyl]quinoxaline (abbreviation. APQ), which is the quinoxaline derivative of the present invention represented by Structural Formula (101).

After that, an electron-transporting layer 2106 was formed having a thickness of 10 nm using tris(8-quinolinolato)aluminum (abbreviation: Alq) over the light-emitting layer 2105 by an evaporation method using resistance heating.

Moreover, an electron-injecting layer 2107 was formed having a thickness of 20 nm by co-evaporating tris(8-quinolinolato)aluminum (abbreviation: Alq) and lithium over the electron-transporting layer 2106. Here, the weight ratio between Alq and lithium was adjusted so as to be 1:0.01 (=Alq:lithium).

Then, a second electrode 2108 was formed of aluminum having a thickness of 200 nm over the electron-injecting layer 2107 by an evaporation method using resistance heating. Thus, a light-emitting element 1 was manufactured.

Figure 30:
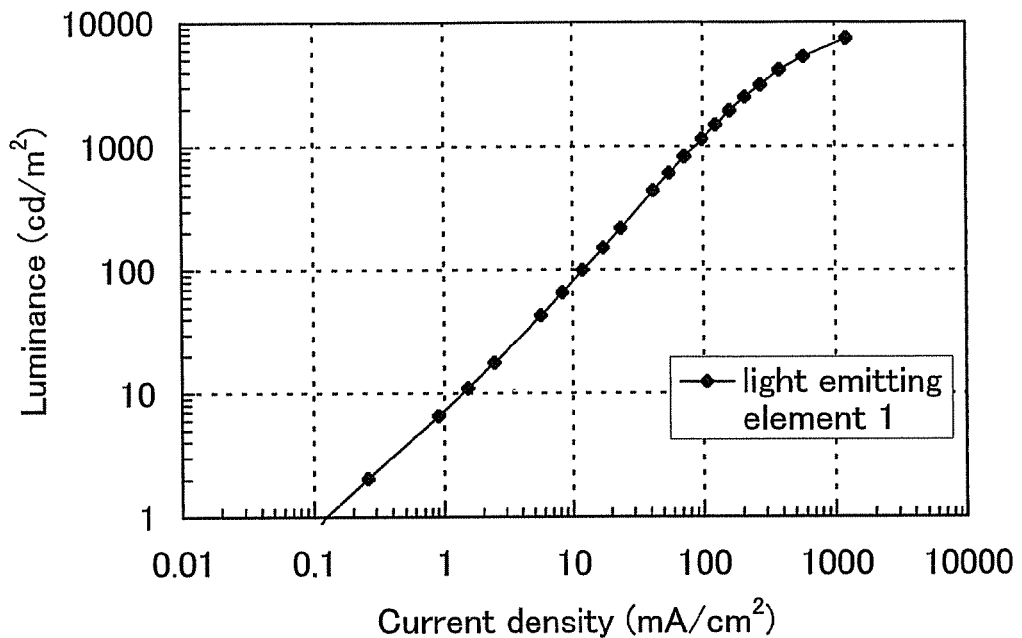
FIG. 30 is a graph showing current density-luminance characteristics of a light-emitting element manufactured in Embodiment 5.
Figure 31:
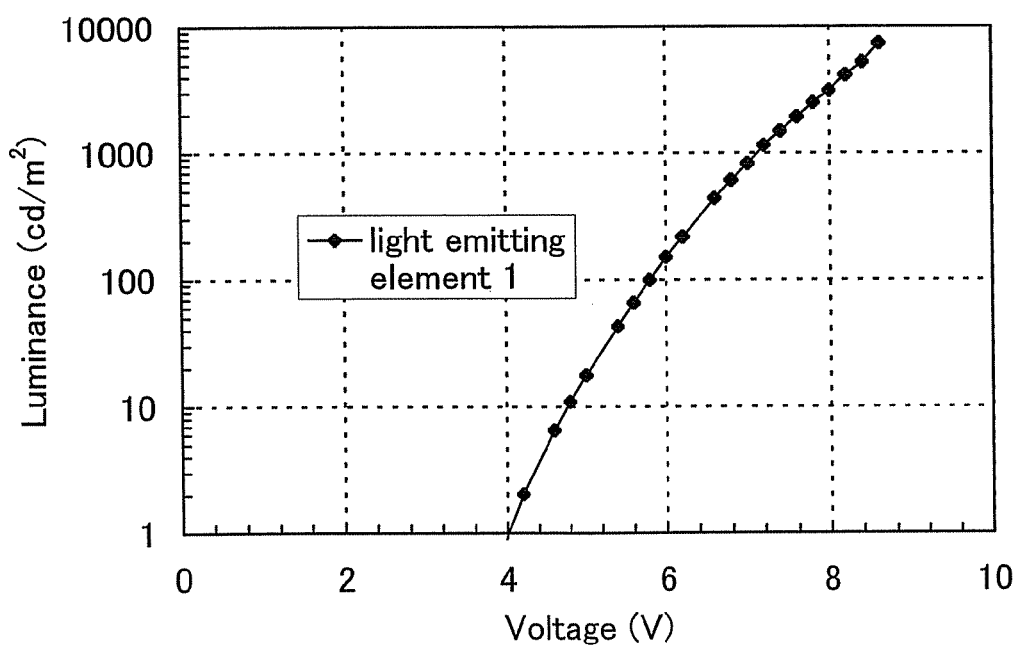
FIG. 31 is a graph showing voltage-luminance characteristics of a light-emitting element manufactured in Embodiment 5.
Figure 32:
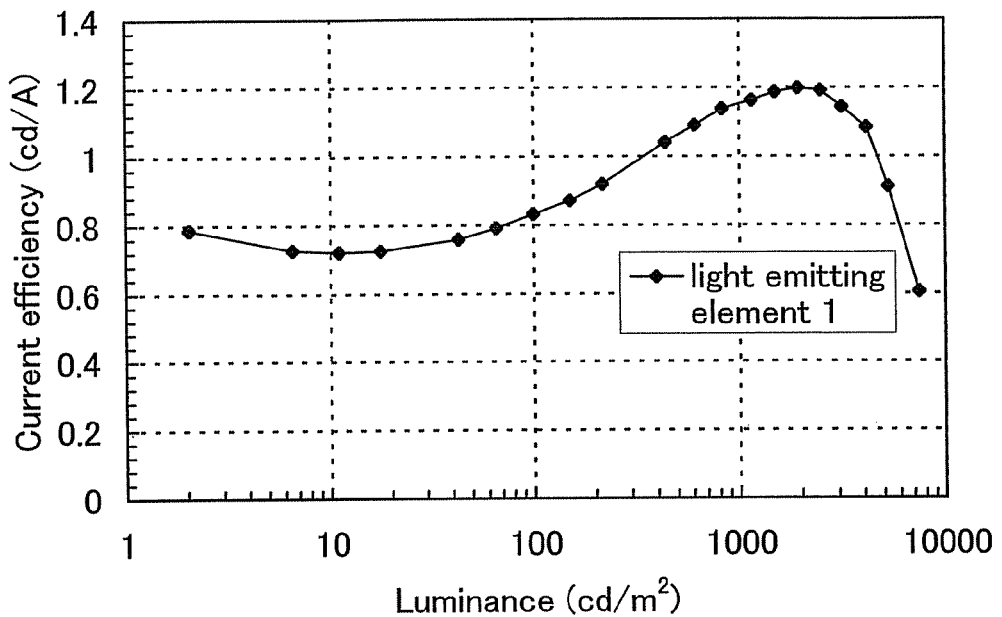
FIG. 32 is a graph showing luminance-current efficiency characteristics of a light-emitting element manufactured in Embodiment 5.
Figure 33:
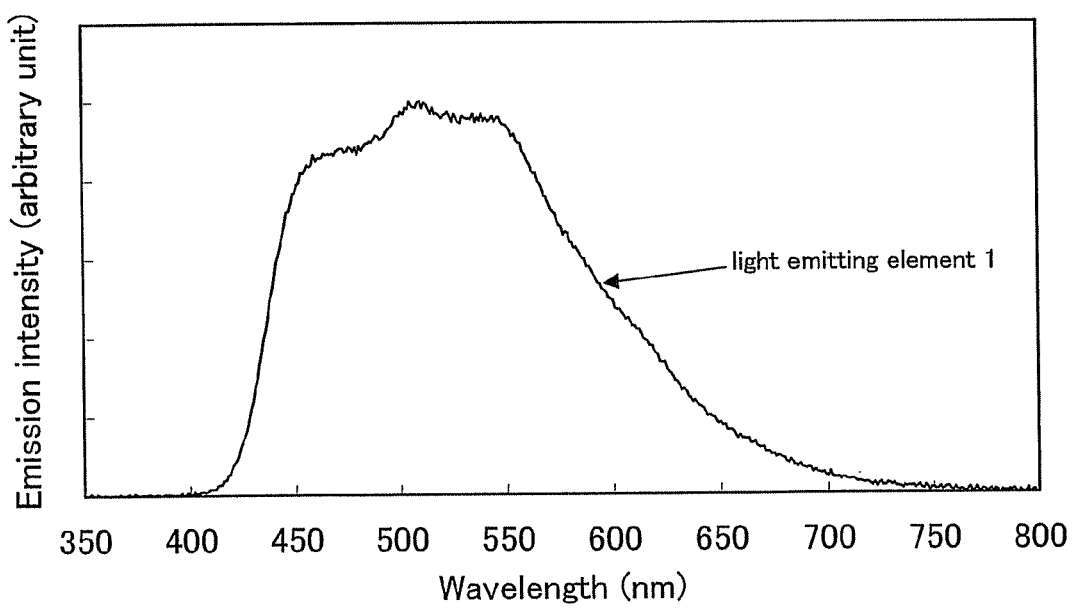
FIG. 33 is a graph showing an emission spectrum of a light-emitting element manufactured in Embodiment 5.

FIG. 30 shows current density-luminance characteristics of the light-emitting element 1, FIG. 31 shows voltage-luminance characteristics thereof, and FIG. 32 shows luminance-current efficiency characteristics thereof. Also, FIG. 33 shows the emission spectrum which was obtained at a current of 1 mA.

A CIE chromaticity coordinate of the light-emitting element 1 at luminance of 1100 cd/m² was (x=0.26, y=0.34), and light emission was bluish white. Current efficiency at luminance of 1100 cd/m² was 1.2 cd/A, and at that time, the voltage was 7.2 V, the current density was 98.6 mA/cm², and power efficiency was 0.51 lm/W. In addition, as shown in FIG. 9, a half bandwidth of an emission spectrum when a current of 1 mA was fed was about 165 nm, and a broad emission spectrum was exhibited.

Accordingly, by using the quinoxaline derivative of the present invention, a light-emitting element with a wide half bandwidth that exhibits a broad emission spectrum can be obtained. In addition, by manufacturing a light-emitting element that emits white light using the quinoxaline derivative of the present invention, a white light-emitting element with an excellent color rendering property can be obtained. Further, since white light emission with an excellent color rendering property can be obtained by using the quinoxaline derivative of the present invention, the quinoxaline derivative of the present invention can be favorably used for a lighting system.

Embodiment 6

In this embodiment, a light-emitting element of the present invention is described with reference to FIG. 9. A manufacturing method of the light-emitting element of this embodiment is described below.

(Light-Emitting Element 2)

First, indium tin oxide containing silicon oxide (ITSO) was deposited over a glass substrate 2101 by a sputtering method, so that a first electrode 2102 was formed. It is to be noted that the thickness thereof was 110 nm and an electrode area was 2 nm×2 nm.

Next, the substrate over which the first electrode was formed was fixed to a substrate holder provided in a vacuum evaporation apparatus in such a way that a surface of the substrate having the first electrode faced downward. The pressure was reduced to be about $10^{-4}$ Pa and then, 4,4'-bis [N-(1-napthyl)-N-phenylamino]biphenyl (abbreviation: NPB) and molybdenum oxide(VI) were co-evaporated on the first electrode 2102, thereby forming a layer 2103 containing a composite material of an organic compound and an inorganic compound. The film thickness of the layer 2103 was 50 nm, and the weight ratio between NPB and molybdenum oxide(VI) was set 4:1 (=NPB:molybdenum oxide). It is to be noted that the co-evaporation method is an evaporation method in which evaporation is performed at one time from plural evaporation sources in one process chamber.

Subsequently, a hole-transporting layer 2104 was formed having a thickness of 10 nm over the layer 2103 containing a composite material using 4,4'-bis[N-(1-napthyl)-N-phenylamino]biphenyl (abbreviation: NPB) by an evaporation method using resistance heating.

Further, a light-emitting layer 2105 having a thickness of 30 nm was formed over the hole-transporting layer 2104 by evaporating 2,3-bis[4-(9-phenyl-10-anthryl)phenyl]quinoxaline (abbreviation: PAPQ), which is the quinoxaline derivative of the present invention represented by Structural Formula (118).

After that, an electron-transporting layer 2106 was formed having a thickness of 10 nm using tris(8-quinolinolato)aluminum (abbreviation: Alq) over the light-emitting layer 2105 by an evaporation method using resistance heating.

Moreover, an electron-injecting layer 2107 was formed having a thickness of 20 nm by co-evaporating tris(8-quinolinolato)aluminum (abbreviation: Alq) and lithium over the electron-transporting layer 2106. Here, the weight ratio between Alq and lithium was adjusted so as to be 1:0.01 (=Alq:lithium).

Then, a second electrode 2108 was formed of aluminum having a thickness of 200 nm over the electron-injecting layer 2107 by an evaporation method using resistance heating. Thus, a light-emitting element 2 was manufactured.

Figure 34:
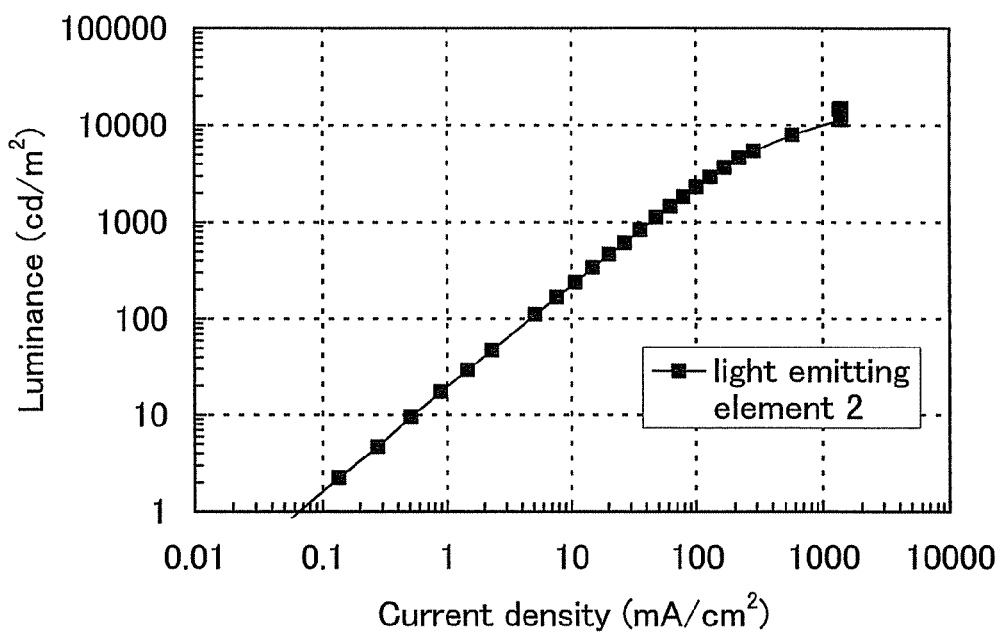
FIG. 34 is a graph showing current density-luminance characteristics of a light-emitting element manufactured in Embodiment 6.
Figure 35:
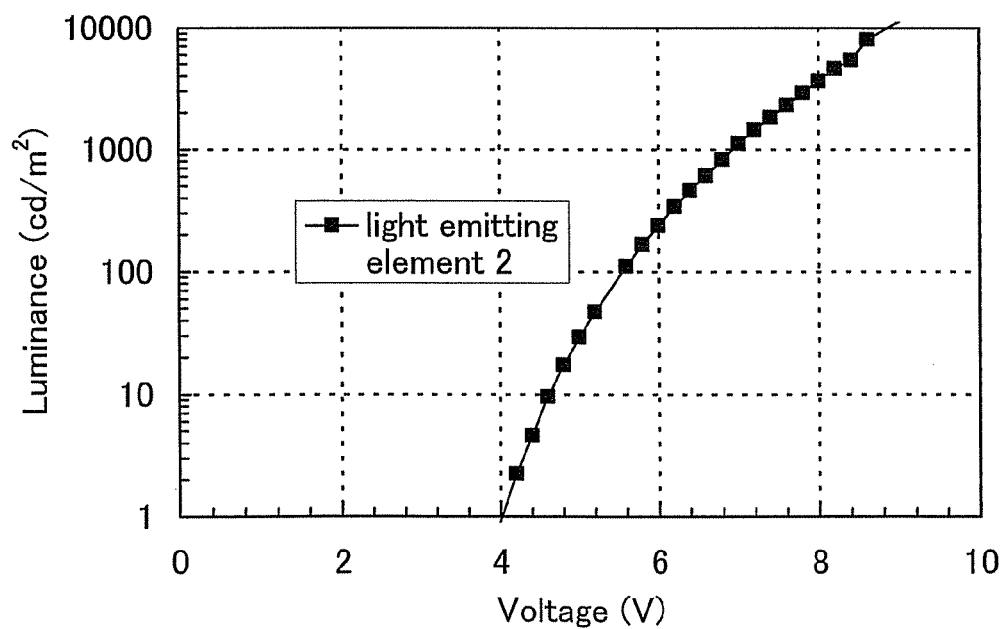
FIG. 35 is a graph showing voltage-luminance characteristics of a light-emitting element manufactured in Embodiment 6.
Figure 36:
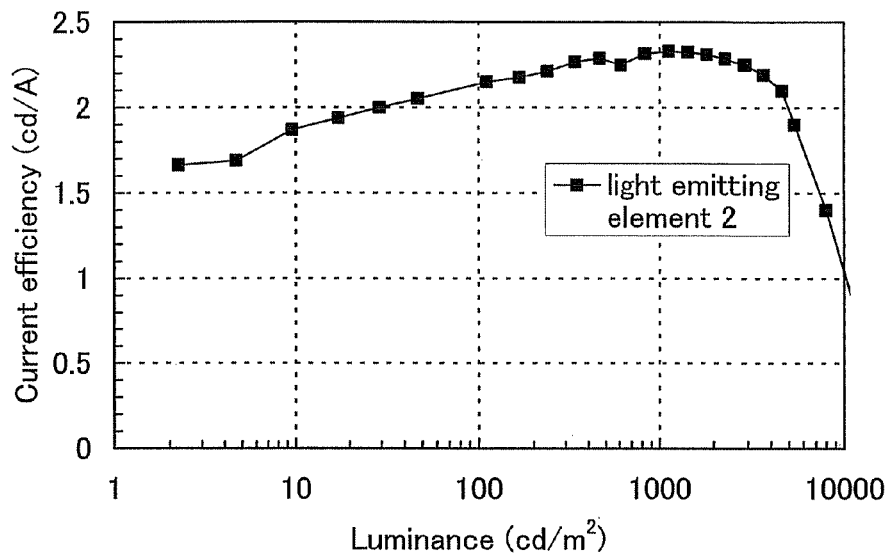
FIG. 36 is a graph showing luminance-current efficiency characteristics of a light-emitting element manufactured in Embodiment 6.
Figure 37:
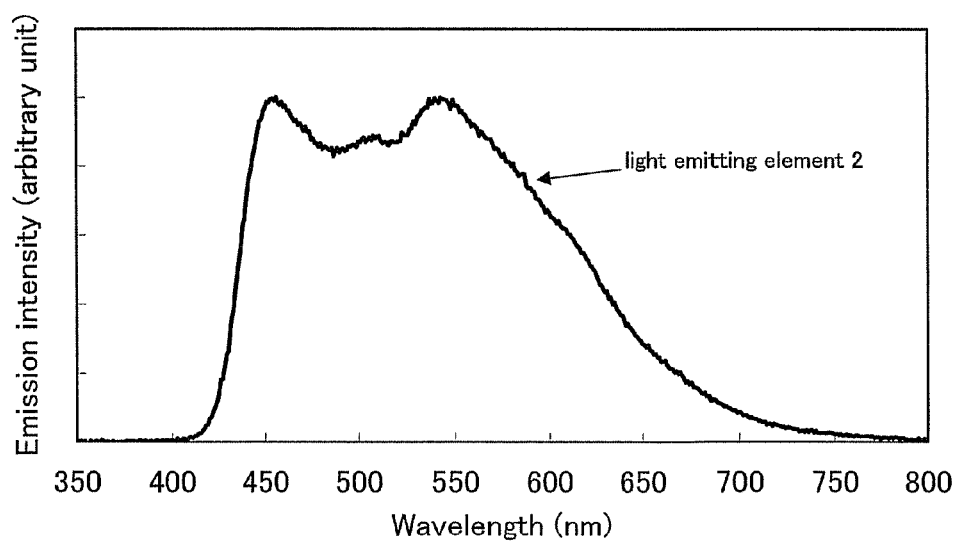
FIG. 37 is a graph showing an emission spectrum of a light-emitting element manufactured in Embodiment 6.

FIG. 34 shows current density-luminance characteristics of the light-emitting element 2, FIG. 35 shows voltage-luminance characteristics thereof and FIG. 36 shows luminance-current efficiency characteristics thereof. In addition, FIG. 37 shows the emission spectrum which was obtained at a current of 1 mA.

A CIE chromaticity coordinate of the light-emitting element 2 at luminance of 1100 cd/m² was (x=0.27, y=0.33), and light emission was bluish white. Current efficiency at luminance of 1100 cd/m² was 2.3 cd/A, and at that time, the voltage was 7.0 V, the current density was 48.2 mA/cm², and power efficiency was 1.0 lm/W. In addition, as shown in FIG. 37, a half bandwidth of an emission spectrum when a current of 1 mA was fed was about 190 nm, and a broad emission spectrum was exhibited.

Accordingly, by using the quinoxaline derivative of the present invention, a light-emitting element with a wide half bandwidth that exhibits a broad emission spectrum can be obtained. In addition, by manufacturing a light-emitting element that emits white light using the quinoxaline derivative of the present invention, a white light-emitting element with an excellent color rendering property can be obtained. Further, since white light emission with an excellent color rendering property can be obtained by using the quinoxaline derivative of the present invention, the quinoxaline derivative of the present invention can be favorably used for a lighting system.

This application is based on Japanese Patent Application serial no. 2006-275716 filed in Japan Patent Office on Oct. 10 in 2006, the entire contents of which are hereby incorporated by reference.

The invention claimed is:

1. A compound represented by Formula (7)

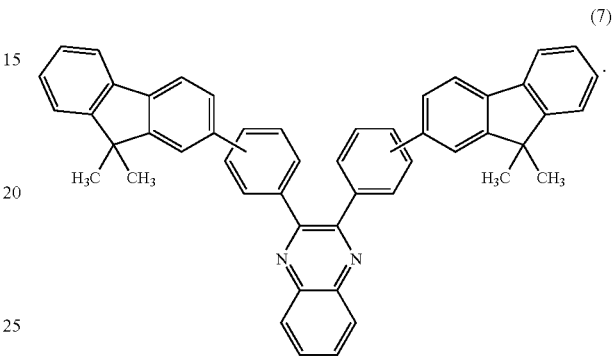

(7)

2. A compound represented by Structural Formula (126)

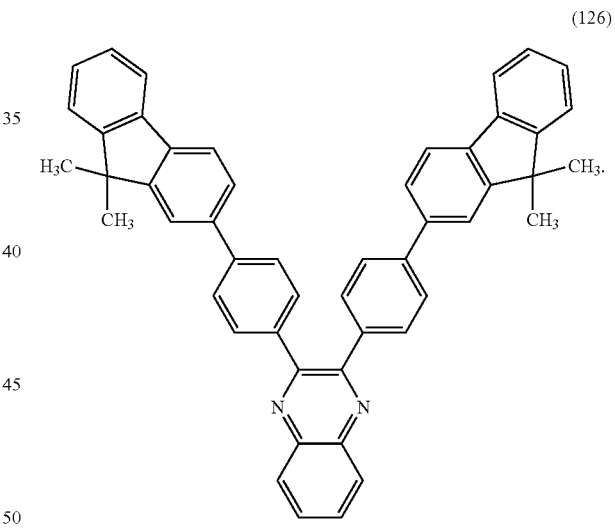

(126)

3. A compound represented by Formula (9)

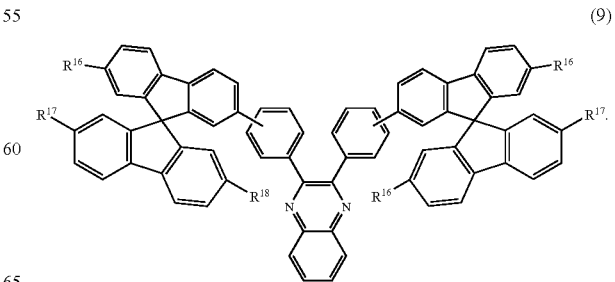

(9)

wherein $R^{16}$ to $R^{18}$ are the same or different from each other, and each represent any of a hydrogen atom or an alkyl group with 1 to 4 carbon atoms.
4. A compound represented by Formula (10)
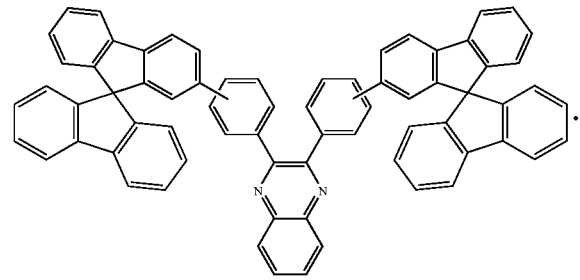
(10)
5. A compound represented by Structural Formula (144)
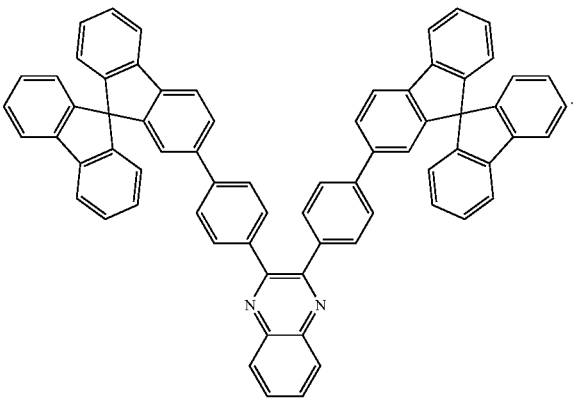
(144)
* * * * *